US012076200B2

United States Patent
Saphier et al.

(10) Patent No.: US 12,076,200 B2
(45) Date of Patent: Sep. 3, 2024

(54) DIGITAL 3D MODELS OF DENTAL ARCHES WITH ACCURATE ARCH WIDTH

(71) Applicant: Align Technology, Inc., San Jose, CA (US)

(72) Inventors: Ofer Saphier, Rechovot (IL); Avi Kopelman, Palo Alto, CA (US)

(73) Assignee: Align Technology, Inc., San Jose, CA (US)

( * ) Notice: Subject to any disclaimer, the term of this patent is extended or adjusted under 35 U.S.C. 154(b) by 914 days.

(21) Appl. No.: 17/095,659

(22) Filed: Nov. 11, 2020

(65) Prior Publication Data
US 2021/0137653 A1    May 13, 2021

Related U.S. Application Data

(60) Provisional application No. 62/934,438, filed on Nov. 12, 2019.

(51) Int. Cl.
*A61C 13/00* (2006.01)
*G06T 7/50* (2017.01)
(Continued)

(52) U.S. Cl.
CPC ............ *A61C 13/0004* (2013.01); *G06T 7/50* (2017.01); *G06T 7/55* (2017.01); *G06T 19/20* (2013.01);
(Continued)

(58) Field of Classification Search
CPC ........... G06T 7/55; G06T 7/521; G06T 7/536; G06T 7/50; G06T 7/586; G06T 7/62; G06T 19/00; G06T 19/20; G06T 2219/00; G06T 2219/028; G06T 2219/2004; G06T 2219/2008; G06T 2207/20041;
(Continued)

(56) References Cited

U.S. PATENT DOCUMENTS 6,099,314 A    8/2000  Kopelman et al.
6,334,772 B1   1/2002  Taub et al.
(Continued)

FOREIGN PATENT DOCUMENTS

WO    WO-2019021285 A1 *  1/2019  ........... A61B 5/0088

OTHER PUBLICATIONS

Pomerleau, Francois et al. "Comparing ICP Variants on Real-World Data Sets"; Autonomous Robots, Apr. 2013, pp. 133-148, vol. 34 No. 3.

*Primary Examiner* — Edward F Urban
*Assistant Examiner* — Duy Tran
(74) *Attorney, Agent, or Firm* — Lowenstein Sandler LLP

(57) ABSTRACT

A method of generating a virtual 3D model of a dental arch is provided. The method includes receiving intraoral scans of a dental arch, determining a first depth of a first intraoral 3D surface in a first intraoral scan, and determining a second depth of a second intraoral 3D surface in the first intraoral scan, and wherein there is a fixed distance between the first intraoral 3D surface and the second intraoral 3D surface in the first intraoral scan. The method further includes stitching together the intraoral scans and generating a virtual 3D model of the dental arch from the intraoral scans, wherein the fixed distance between the first intraoral 3D surface and the second intraoral 3D surface is included in the virtual 3D model.

24 Claims, 29 Drawing Sheets

(51) Int. Cl.
*G06T 7/55* (2017.01)
*G06T 19/20* (2011.01)

(52) U.S. Cl.
CPC .............. *G06T 2219/028* (2013.01); *G06T 2219/2004* (2013.01); *G06T 2219/2008* (2013.01)

(58) Field of Classification Search
CPC . G06T 2200/08; G06T 2200/04; A61C 13/00; A61C 13/0004; A61C 5/70; A61C 8/00; A61C 13/1013; A61C 9/002
See application file for complete search history.

(56) References Cited

U.S. PATENT DOCUMENTS

| | | |
|---|---|---|
| 6,334,853 B1 | 1/2002 | Kopelman et al. |
| 6,463,344 B1 | 10/2002 | Pavlovskaia et al. |
| 6,542,249 B1 | 4/2003 | Kofman et al. |
| 6,633,789 B1 | 10/2003 | Nikolskiy et al. |
| 6,664,986 B1 | 12/2003 | Kopelman et al. |
| 6,697,164 B1 | 2/2004 | Babayoff et al. |
| 6,845,175 B2 | 1/2005 | Kopelman et al. |
| 6,979,196 B2 | 12/2005 | Nikolskiy et al. |
| 7,030,383 B2 | 4/2006 | Babayoff et al. |
| 7,202,466 B2 | 4/2007 | Babayoff et al. |
| 7,255,558 B2 | 8/2007 | Babayoff et al. |
| 7,286,954 B2 | 10/2007 | Kopelman et al. |
| 7,319,529 B2 | 1/2008 | Babayoff |
| 7,373,286 B2 | 5/2008 | Nikolskiy et al. |
| 7,507,088 B2 | 3/2009 | Taub et al. |
| 7,545,372 B2 | 6/2009 | Kopelman et al. |
| 7,698,068 B2 | 4/2010 | Babayoff |
| 7,916,911 B2 | 3/2011 | Kaza et al. |
| 8,108,189 B2 | 1/2012 | Chelnokov et al. |
| 8,244,028 B2 | 8/2012 | Kuo et al. |
| 8,587,582 B2 | 11/2013 | Matov et al. |
| 8,948,482 B2 | 2/2015 | Levin |
| D742,518 S | 11/2015 | Barak et al. |
| 9,192,305 B2 | 11/2015 | Levin |
| 9,261,356 B2 | 2/2016 | Lampert et al. |
| 9,261,358 B2 | 2/2016 | Atiya et al. |
| 9,299,192 B2 | 3/2016 | Kopelman |
| D760,901 S | 7/2016 | Barak et al. |
| 9,393,087 B2 | 7/2016 | Moalem |
| 9,408,679 B2 | 8/2016 | Kopelman |
| 9,431,887 B2 | 8/2016 | Boltanski |
| 9,439,568 B2 | 9/2016 | Atiya et al. |
| 9,451,873 B1 | 9/2016 | Kopelman et al. |
| D768,861 S | 10/2016 | Barak et al. |
| D771,817 S | 11/2016 | Barak et al. |
| 9,491,863 B2 | 11/2016 | Boltanski |
| D774,193 S | 12/2016 | Makmel et al. |
| 9,510,757 B2 | 12/2016 | Kopelman et al. |
| 9,660,418 B2 | 5/2017 | Atiya et al. |
| 9,668,829 B2 | 6/2017 | Kopelman |
| 9,675,430 B2 | 6/2017 | Verker et al. |
| 9,693,839 B2 | 7/2017 | Atiya et al. |
| 9,717,402 B2 | 8/2017 | Lampert et al. |
| 9,724,177 B2 | 8/2017 | Levin |
| 9,844,426 B2 | 12/2017 | Atiya et al. |
| 10,039,475 B2 | 8/2018 | Sorimoto et al. |
| 10,076,389 B2 | 9/2018 | Wu et al. |
| 10,098,714 B2 | 10/2018 | Kuo |
| 10,108,269 B2 | 10/2018 | Sabina et al. |
| 10,111,581 B2 | 10/2018 | Makmel |
| 10,111,714 B2 | 10/2018 | Kopelman et al. |
| 10,123,706 B2 | 11/2018 | Elbaz et al. |
| 10,136,972 B2 | 11/2018 | Sabina et al. |
| 10,380,212 B2 | 8/2019 | Elbaz et al. |
| 10,390,913 B2 | 8/2019 | Sabina et al. |
| 10,453,269 B2 | 10/2019 | Furst |
| 10,456,043 B2 | 10/2019 | Atiya et al. |
| 10,499,793 B2 | 12/2019 | Ozerov et al. |
| 10,504,386 B2 | 12/2019 | Levin et al. |
| 10,507,087 B2 | 12/2019 | Elbaz et al. |
| 10,517,482 B2 | 12/2019 | Sato et al. |
| 10,695,150 B2 | 6/2020 | Kopelman et al. |
| 10,708,574 B2 | 7/2020 | Furst et al. |
| 10,772,506 B2 | 9/2020 | Atiya et al. |
| 10,813,727 B2 | 10/2020 | Sabina et al. |
| 10,888,399 B2 | 1/2021 | Kopelman et al. |
| 10,952,816 B2 | 3/2021 | Kopelman |
| 10,980,613 B2 | 4/2021 | Shanjani et al. |
| 2012/0062701 A1* | 3/2012 | Dillon .................. A61B 5/0062 348/45 |
| 2013/0273492 A1 | 10/2013 | Suttin, Sr. et al. |
| 2014/0022356 A1* | 1/2014 | Fisker .................. A61B 5/1076 348/47 |
| 2014/0146142 A1* | 5/2014 | Duret .................... A61C 19/04 348/46 |
| 2015/0320320 A1* | 11/2015 | Kopelman ............. A61B 5/486 433/215 |
| 2015/0379780 A1* | 12/2015 | Jin ......................... A61B 6/463 345/419 |
| 2018/0028292 A1 | 2/2018 | Pesach et al. |
| 2019/0029784 A1 | 1/2019 | Moalem et al. |
| 2019/0231492 A1 | 8/2019 | Sabina et al. |
| 2019/0388193 A1 | 12/2019 | Saphier et al. |
| 2019/0388194 A1 | 12/2019 | Atiya et al. |
| 2020/0281701 A1 | 9/2020 | Kopelman et al. |
| 2020/0281702 A1 | 9/2020 | Kopelman et al. |
| 2020/0315434 A1 | 10/2020 | Kopelman et al. |
| 2020/0349698 A1 | 11/2020 | Minchenkov et al. |
| 2020/0349705 A1 | 11/2020 | Minchenkov et al. |
| 2020/0404243 A1 | 12/2020 | Saphier et al. |
| 2021/0030503 A1 | 2/2021 | Shalev et al. |
| 2021/0059796 A1 | 3/2021 | Weiss et al. |
| 2021/0068773 A1 | 3/2021 | Moshe et al. |
| 2021/0121049 A1 | 4/2021 | Rudnitsky et al. |
| 2021/0128281 A1 | 5/2021 | Peleg |

* cited by examiner

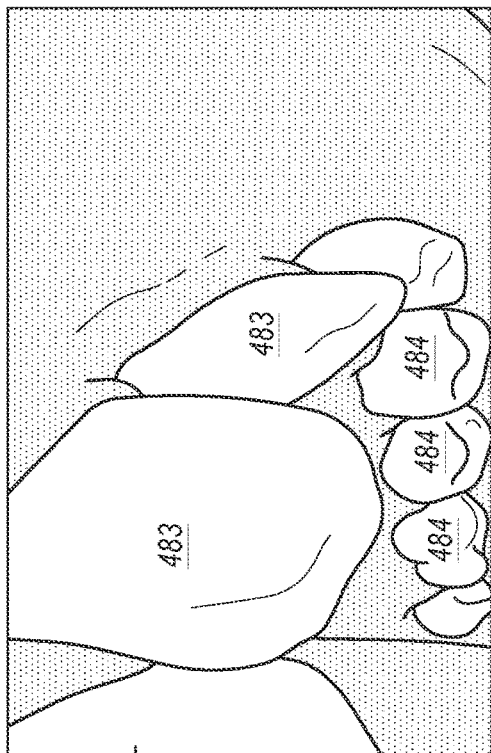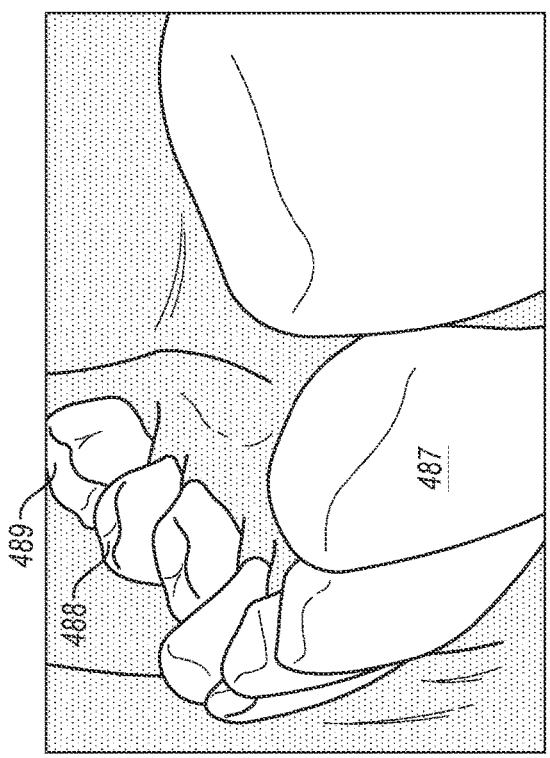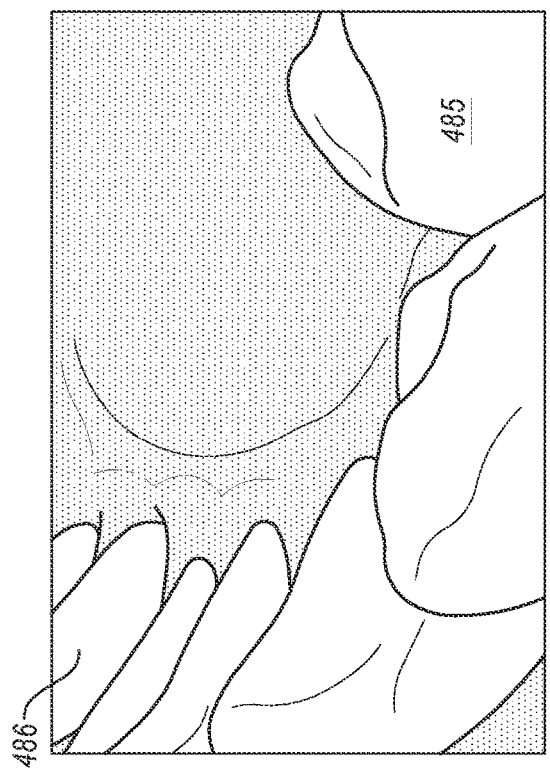
FIG. 4D
FIG. 4E
FIG. 4F
FIG. 4G

DIGITAL 3D MODELS OF DENTAL ARCHES WITH ACCURATE ARCH WIDTH

RELATED APPLICATIONS

This patent application claims the benefit under 35 U.S.C. § 119(e) of U.S. Provisional Application No. 62/934,438, filed Nov. 12, 2019, which is herein incorporated by reference.

TECHNICAL FIELD

Embodiments of the present disclosure relate to the field of intraoral scanning and, in particular, to a system and method for improving the results of intraoral scanning in oral cavities, such as the results of intraoral scanning of oral cavities that lack one or more teeth.

BACKGROUND

In prosthodontic procedures designed to implant a dental prosthesis in the oral cavity, the dental site at which the prosthesis is to be implanted in many cases should be measured accurately and studied carefully, so that a prosthesis such as a crown, denture or bridge, for example, can be properly designed and dimensioned to fit in place. A good fit enables mechanical stresses to be properly transmitted between the prosthesis and the jaw, and to prevent infection of the gums via the interface between the prosthesis and the dental site, for example:

Some procedures also call for prosthetics to be fabricated to replace one or more missing teeth, such as a partial or full denture, in which case the surface contours of the areas where the teeth are missing need to be reproduced accurately so that the resulting prosthetic fits over the edentulous region with even pressure on the soft tissues.

In some practices, the dental site is prepared by a dental practitioner, and a positive physical model of the dental site is constructed using known methods. Alternatively, the dental site may be scanned to provide 3D data of the dental site. In either case, the virtual or real model of the dental site is sent to the dental lab, which manufactures the prosthesis based on the model. However, if the model is deficient or undefined in certain areas, or if a preparation was not optimally configured for receiving the prosthesis or is inaccurate, the design of the prosthesis may be less than optimal.

In orthodontic procedures it can be important to provide a model of one or both jaws. Where such orthodontic procedures are designed virtually, a virtual model of the dental arches is also beneficial. Such a virtual model may be obtained by scanning the oral cavity directly, or by producing a physical model of the dentition, and then scanning the model with a suitable scanner.

Thus, in both prosthodontic and orthodontic procedures, obtaining a three-dimensional (3D) model of a dental arch in the oral cavity is an initial procedure that is performed. When the 3D model is a virtual model, the more complete and accurate the scans of the dental arch are, the higher the quality of the virtual model, and thus the greater the ability to design an optimal prosthesis or orthodontic treatment appliance(s).

Scanning of the dental arch is complicated by regions in which a patient is missing teeth, referred to as edentulous regions. For example, in cases where two or more adjacent teeth are missing, there may be a large span of soft tissue that needs to be scanned. Such regions can be difficult to scan because these edentulous regions lack features on which stitching between scans would be successfully applied.

A particular inaccuracy that is common for virtual 3D models generated from scans of a dental arch or mold of a dental arch is an inaccuracy in the width of the dental arch or jaw, referred to as the intermolar width. Virtual 3D models are generated by stitching together many smaller images of portions of the dental arch, and each registration of one image to another image introduces a small amount of error. These small errors accumulate such that the accuracy of the distance between the rightmost molar and the leftmost molar (the intermolar width) generally has about a 200-400 micron error. While the 200-400 micron error is acceptable for some dental procedures (e.g., in the case of a single crown), this level of error can cause failure in other dental procedures. For example, an all-on-four procedure that places a full set of prosthetic teeth onto four dental implants attached to a patient's jaw is a global structure that requires high accuracy for the intermolar width. However, the at-on-four procedure is generally performed on an edentulous dental arch, which reduces the accuracy of the virtual 3D model of the dental arch due to having no features for stitching or low quality features for stitching. Thus, obtaining accurate 3D models of dental arches that are used for the all-on-four procedure is particularly challenging.

Some intraoral scanners are used in conjunction with a powder that is applied to a dental region. The powder may include particles that can be distinguished from other powder particles, with the goal of providing measurable points in the dental site that provide features for stitching (also referred to herein as registration). For such systems, these particles may be used to aid image registration when they operate as intended. However, the powder often does not connect well to soft tissue, and in particular to wet soft tissue. Additionally, the powder may become wet and/or wash away during scanning, decreasing an accuracy of later image registration. Additionally, many patients do not like having the powder applied to their teeth and in their mouth. Having to powder the teeth can have drawbacks such as:
1. All areas have to be powdered and the thickness of the powder layer is not homogeneous, which compromises accuracy (e.g., since the surface is not scanned directly);
2. If the scanner head touches the powder, it sticks to the optics and introduces noise to the scan;
3. The powder can be costly;
4. Some people are allergic to the powder; and
5. Color scanning of the teeth is not possible as it is all painted in white.

SUMMARY

In a first aspect of the disclosure, a method includes receiving, by a processing device, a plurality of intraoral scans of a dental arch. The method further includes determining, by the processing device, that at least one intraoral scan of the plurality of intraoral scans comprises a buccal view of a first three-dimensional (3D) surface and a lingual view of at least a feature of a second 3D surface that is not connected to the first 3D surface in the at least one intraoral scan, wherein there is a distance between the first 3D surface and at least the feature of the second 3D surface in the at least one intraoral scan. The method further includes stitching together the plurality of intraoral scans and generating a virtual 3D model of the dental arch from the plurality of intraoral scans, wherein a distance between the first 3D surface and the second 3D surface in the virtual 3D model is based on the distance between first 3D surface and the feature of the second 3D surface in the at least one intraoral scan.

In another aspect of the disclosure, a method includes receiving, by a processing device, a plurality of intraoral scans of a dental arch. The method further includes determining, by the processing device, that at least one intraoral scan of the plurality of intraoral scans comprises a depiction of a first three-dimensional (3D) surface and a depiction of at least a feature of a second 3D surface that is separated from the first 3D surface by at least one intervening 3D surface not shown in the at least one intraoral scan, wherein there is a distance between the first 3D surface and the feature of the second 3D surface in the at least one intraoral scan. The method further includes stitching together the plurality of intraoral scans and generating a virtual 3D model of the dental arch from the plurality of intraoral scans, wherein a distance between the first 3D surface and the second 3D surface in the virtual 3D model is based on the distance between first 3D surface and the feature of the second 3D surface in the at least one intraoral scan.

In another aspect of the disclosure, a method of scanning an edentulous dental arch of a patient includes receiving an indication of a dental prosthetic to be manufactured for the patient, wherein the dental prosthetic is to attach to at least a first dental implant and a second dental implant on the edentulous dental arch. The method further includes receiving a plurality of intraoral scans of the edentulous dental arch and determining whether any intraoral scan of the plurality of intraoral scans depicts both a first scan body associated with the first dental implant and a second scan body associated with the second dental implant. The method further includes, responsive to determining that none of the plurality of intraoral scans depicts both the first scan body and the second scan body, outputting an instruction to position a probe of an intraoral scanner to generate at least one intraoral scan depicting both the first scan body and the second scan body. The method further includes receiving the at least one intraoral scan depicting the first scan body and the second scan body and generating a virtual three-dimensional (3D) model of the edentulous dental arch using the plurality of intraoral scans and the at least one intraoral scan.

BRIEF DESCRIPTION OF THE DRAWINGS

The present disclosure is illustrated by way of example, and not by way of limitation, in the figures of the accompanying drawings.

FIGS. 4D-J illustrate some example intraoral scans showing nearby teeth and far teeth in a single scan, which can be used to improve accuracy of surface registration, in accordance with embodiments of the present disclosure.

DETAILED DESCRIPTION

Figure 1A:
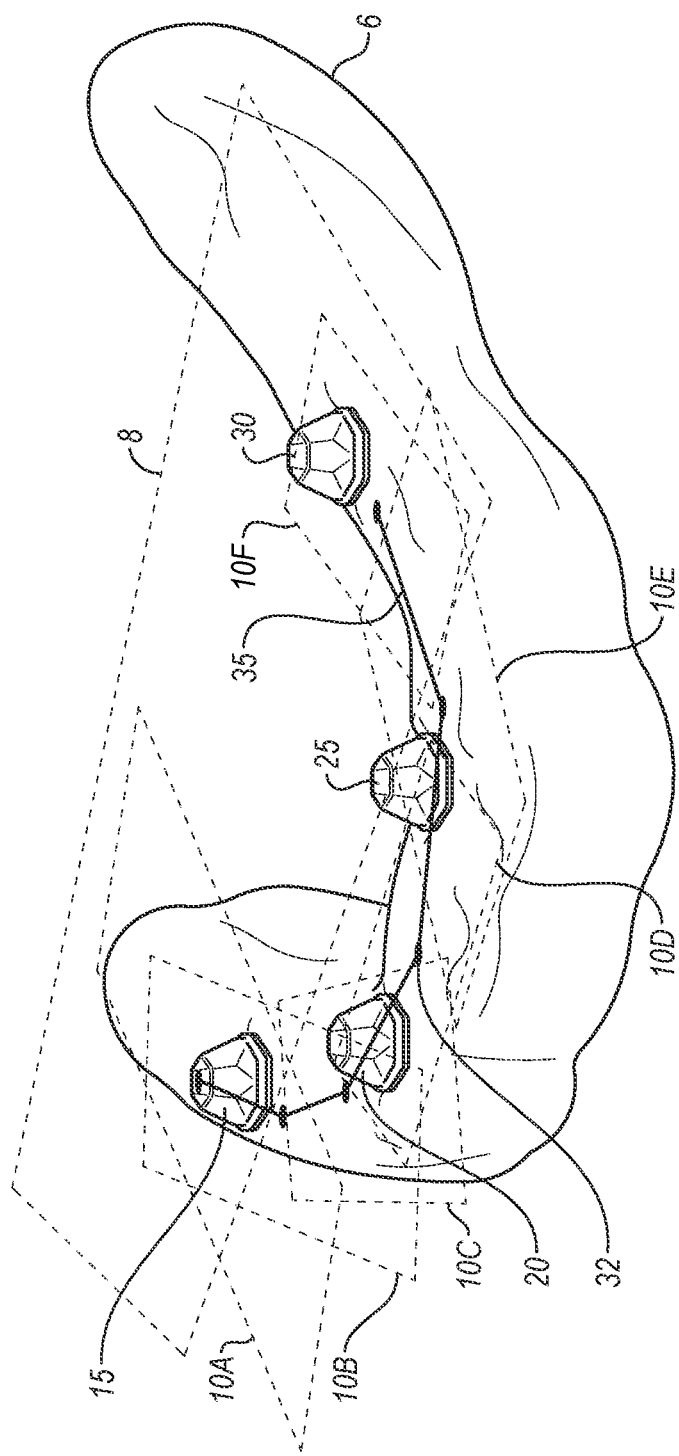
FIG. 1A illustrates a set of scans of an edentulous dental arch with four scan bodies, in accordance with embodiments of the present disclosure.

Described herein is a method and apparatus for improving the quality of intraoral scans of dental arches, including the quality of intraoral scans taken of dental arches for patients missing some or all of their teeth. In particular, embodiments enable virtual 3D models of dental arches to be generated that have less than a 200 micron error for a width of the dental arch (e.g., the intermolar width). In some embodiments, the error for the intermolar width may be less than 100 microns, or may be as low as 20 microns or less, and thus may be significantly less than the error in intermolar width of 3D models for dental arches that are produced using conventional intraoral scanners. For example, the error for intermolar width of 3D models of dental arches is conventionally about a 200-400 microns, while the error for intermolar width of 3D models of dental arches in embodiments may be below 200 microns, below 180 microns, below 150 microns, below 120 microns, below 100 microns, below 80 microns, below 50 microns, or below 20 microns in embodiments.

Embodiments provide improved techniques for generating 3D modes of dental arches that take advantage of large fields of view (FOV) and/or large ranges of depths of focus. One or more scans may be generated that include a first 3D surface on a first quadrant of a dental arch and at least a feature of a second 3D surface on a second quadrant of the dental arch. These scans may be used along with other conventional scans to generate a 3D model of a dental arch that is highly accurate (e.g., with an error of as low as 20 microns in some embodiments).

In one embodiment, a processing device receives intraoral scans from an intraoral scanning session of a patient. The intraoral scans may be or include discrete images (e.g., point-and-shoot images) or frames from an intraoral video (e.g., a continuous scan). Some of the intraoral scans may include representations of first 3D surfaces on a near half of a dental arch (or quadrant of a jaw) and representations of far 3D surfaces on a far half of the dental arch (or quadrant of the jaw). The 3D surfaces on the near half of the dental arch may have a depth (distance from a probe of an intraoral scanner) of about 0-5 mm or 0-10 mm in some embodiments. The 3D surfaces on the far half of the dental arch may have a depth of about 40-90 mm or about 30-80 mm in some embodiments for molar to molar distances. Accordingly, a single intraoral scan may have a large depth (e.g., up to 40 mm, 50 mm, 60 mm, 70 mm, 80 mm or 90 mm), and may include representations of both 3D surfaces on the left half and the right half of a dental arch. This intraoral scan may be used to vastly improve the accuracy of a virtual 3D model of the dental arch by mitigating or eliminating the accumulation of errors that would generally occur in stitching together scans of molars (or molar regions if the molars are missing) in the left half ultimately to the scans of the molars (or molar regions if the molars are missing) in the right half. For canine to canine separation, the 3D surfaces on the far half of the dental arch may have a depth of about 30 mm or less. For anterior to molar separation or canine to molar separation, the far half of the dental arch may have a depth of about 30 mm or less. These diagonal views may also improve longitudinal error (e.g., error of the length of the jaw), which can improve orthodontic treatment.

In embodiments, an intraoral scanner has a field of view (FOV) with a depth of focus that is much higher than the depths of focus of conventional intraoral scanners. For example, embodiments of the present disclosure may be enabled by an intraoral scanner having a large depth of focus that may detect 3D surfaces up to 30 mm, 40 mm, 50 mm, 60 mm, 70 mm, 80 mm or 90 mm from a probe of the intraoral scanner. For example, in some particular applications of the present disclosure, an apparatus is provided for intraoral scanning, the apparatus including an elongate handheld wand with a probe at the distal end. During a scan, the probe may be configured to enter the intraoral cavity of a subject. One or more light projectors (e.g., miniature structured light projectors) as well as one or more cameras (e.g., miniature cameras) may be coupled to a rigid structure disposed within a distal end of the probe. Each of the light projectors transmits light using a light source, such as a laser diode. One or more structured light projector may be configured to project a pattern of light defined by a plurality of projector rays when the light source is activated. Each camera may be configured to capture a plurality of images that depict at least a portion of the projected pattern of light on an intraoral surface. In some applications, the light projectors may have a field of illumination of at least 45 degrees. Optionally, the field of illumination may be less than 120 degrees. For structured light projectors, each of the structured light projectors may further include a pattern generating optical element. The pattern generating optical element may utilize diffraction and/or refraction to generate a light pattern. In some applications, the light pattern may be a distribution of discrete unconnected spots of light. Optionally, the light pattern maintains the distribution of discrete unconnected spots at all planes located up to a threshold distance (e.g., 30 mm, 40 mm, 60 mm, etc.) from the pattern generating optical element, when the light source (e.g., laser diode) is activated to transmit light through the pattern generating optical element. Each of the cameras includes a camera sensor and objective optics including one or more lenses.

In some applications, in order to improve image capture of an intraoral scene under structured light illumination, without using contrast enhancement means such as coating the teeth with an opaque powder, a distribution of discrete unconnected spots of light (as opposed to lines, for example) may provide an improved balance between increasing pattern contrast while maintaining a useful amount of information. In some applications, the unconnected spots of light have a uniform (e.g., unchanging) pattern. Generally speaking, a denser structured light pattern may provide more sampling of the surface, higher resolution, and enable better stitching of the respective surfaces obtained from multiple scan frames. However, too dense a structured light pattern may lead to a more complex correspondence problem due to there being a larger number of spots for which to solve the correspondence problem. Additionally, a denser structured light pattern may have lower pattern contrast resulting from more light in the system, which may be caused by a combination of (a) stray light that reflects off the somewhat glossy surface of the teeth and may be picked up by the cameras, and (b) percolation, i.e., some of the light entering the teeth, reflecting along multiple paths within the teeth, and then leaving the teeth in many different directions. As described further hereinbelow, methods and systems are provided for solving the correspondence problem presented by the distribution of discrete unconnected spots of light. In some applications, the discrete unconnected spots of light from each projector may be non-coded.

In some embodiments, one or more of the light projectors are not structured light projectors. For example, one or more of the light projectors may be non-structured light projectors, which may project coherent and/or non-coherent light, such as white light or near-infrared (NIRI) light. It should be understood that embodiments described herein with reference to structured light and structured light projectors also apply to combinations of structured light and structured light projectors with non-structured light and non-structured light projectors.

In some applications, the field of view of each of the cameras may be at least 45 degrees, e.g., at least 80 degrees, e.g., 85 degrees. Optionally, the field of view of each of the cameras may be less than 120 degrees, e.g., less than 90 degrees. The fields of view of the various cameras may together form a field of view of the intraoral scanner. In any case, the field of view of the various cameras may be identical or non-identical. Similarly, the focal length of the various cameras may be identical or non-identical. The term "field of view" of each of the cameras, as used herein, refers to the diagonal field of view of each of the cameras. Further, each camera may be configured to focus at an object focal plane that is located up to a threshold distance from the respective camera sensor (e.g., up to a distance of 10 mm, 20 mm, 30 mm, 40 mm, 50 mm, 60 mm, 70 mm, 80 mm, etc. from the respective camera sensor). As distances increase, the accuracy of the position of the detected surfaces decreases. In one embodiment, beyond the threshold distance the accuracy is below an accuracy threshold. Similarly, in some applications, the field of illumination of each of the light projectors (e.g., structured light projectors and/or non-structured light projectors) may be at least 45 degrees and optionally less than 120 degrees. A large field of view (FOV) of the intraoral scanner achieved by combining the respective fields of view of all the cameras may improve accuracy (as compared to traditional scanners that typically have a FOV of 10-20 mm in the x-axis and y-axis and a depth of capture of about 0-15 or 0.025 mm) due to reduced amount of image stitching errors, especially in edentulous regions, where the gum surface is smooth and there may be fewer clear high resolution 3-D features. Having a larger FOV for the intraoral scanner enables large smooth features, such as the overall curve of the tooth, to appear in each image frame, which improves the accuracy of stitching respective surfaces obtained from multiple such image frames.

In some applications, the total combined FOV of the various cameras (e.g., of the intraoral scanner) is between about 20 mm and about 50 mm along the longitudinal axis of the elongate handheld wand, and about 20-60 mm (or 20-40 mm) in the z-axis, where the z-axis may correspond to depth. In further applications, the field of view may be about 20 mm, about 25 mm, about 30 mm, about 35 mm, or about 40 mm along the longitudinal axis and/or at least 20 mm, at least 25 mm, at least 30 mm, at least 35 mm, at least 40 mm, at least 45 mm, at least 50 mm, at least 55 mm, at least 60 mm, at least 65 mm, at least 70 mm, at least 75 mm, or at least 80 mm in the z-axis. In some embodiments, the combined field of view may change with depth (e.g., with scanning distance). For example, at a scanning distance of about 4 mm the field of view may be about 20 mm along the longitudinal axis, and at a scanning distance of about 20-50 mm the field of view may be about 30 mm or less along the longitudinal axis. If most of the motion of the intraoral scanner is done relative to the long axis (e.g., longitudinal axis) of the scanner, then overlap between scans can be substantial. In some applications, the field of view of the combined cameras is not continuous. For example, the intraoral scanner may have a first field of view separated from a second field of view by a fixed separation. The fixed separation may be, for example, along the longitudinal axis of the elongate handheld wand.

In some embodiments, the large FOV of the intraoral scanner increases an accuracy of the detected depth of 3D surfaces. For example, the accuracy of a depth measurement of a detected 3D surface may be based on the longitudinal distance between two cameras or between a light projector and a camera, which may represent a triangulation bae line distance. In embodiments, cameras and/or light projectors may be spaced apart in a configuration that provides for increased accuracy of depth measurements for 3D surfaces that, for example, have a depth of up to 30 mm, up to 40 mm, up to 50 mm, up to 60 mm, and so on.

In some applications, a method is provided for generating a digital three-dimensional (3D) model of an intraoral surface. The 3D model may be a point cloud, from which an image of the three-dimensional intraoral surface may be constructed. The resultant image of the 3D model, while generally displayed on a two-dimensional screen, contains data relating to the three-dimensional structure of the scanned 3D surface, and thus may typically be manipulated so as to show the scanned 3D surface from different views and perspectives. Additionally, a physical three-dimensional model of the scanned 3D surface may be made using the data from the three-dimensional model. As discussed above, the 3D model may be a 3D model of a dental arch, and the 3D model of the dental arch may have an arch width (e.g., an intermolar width) that is highly accurate (e.g., with an error of about 20 microns or less in some embodiments).

Turning now to the figures, FIG. 1A illustrates a set of scans 8 and 10A-F of an edentulous dental arch 6 with four scan bodies 15, 20, 25, 30, in accordance with embodiments of the present disclosure. Each of the scan bodies 15-30 may be attached to a separate dental implant in an embodiment. Each scan body 15-30 may be 3D structure with a known shape or geometry. Many scans 8, 10A-F may be generated of the dental arch 6. In the illustrated example, six occlusal scans 10 are shown, and one buccal scan 8 is shown. However, generally to fully scan a dental arch many more scans would be generated, including, for example, buccal scans, lingual scans, and occlusal scans. The scans 8, 10A-F are stitched together to generate a virtual 3D model of the dental arch 6. The centers of scans 10A-F are represented with dots 32, and lines 35 between such dots represent links between scans that have been registered together. Each registration of one scan to another scan includes some level of error. Traditionally, many such links are required to span from one quadrant of the dental arch (e.g., from scan body 15) to another quadrant of the dental arch (e.g., to scan body 30). Though each individual error associated with a link between two scans is small, an accumulated error between distant scans that are connected by many links may be clinically significant. For example, the relative distance between scan body 15 and scan body 30 may have an error of 200-300 microns. Accordingly, the determined arch width of the dental arch may have an error of about 200-300 microns. To reduce the error for the distance between distant scans (e.g., scans on different quadrants of a dental arch), and to reduce the error of the calculated arch width, one or more scans 8 may be generated that include a first surface of the first scan body 15 and at least a feature of a second surface of the scan body 30. Such scans are enabled in embodiments as described herein. The inclusion of such a scan 8 vastly increases the accuracy of the distance between scan body 15 and scan body 30, and additionally vastly increases the accuracy of the computed arch width of the dental arch 6. For example, absent scan 8, the number of links to connect scan 10A to scan 10F is five in the illustrated simplified example. However, by adding scan 8, the number of links to connect scan 10A to scan 10F is two (one link from scan 10A to scan 8 and one link from scan 8 to scan 10F). Similarly, the number of links to connect scan 10A to scan 10E is reduced from four to three in the illustrated example when scan 8 is included. Additionally, by having two scan bodies shown in scan 8, a more accurate estimate of the distance between these two scan bodies may be determined.

Figure 1B:
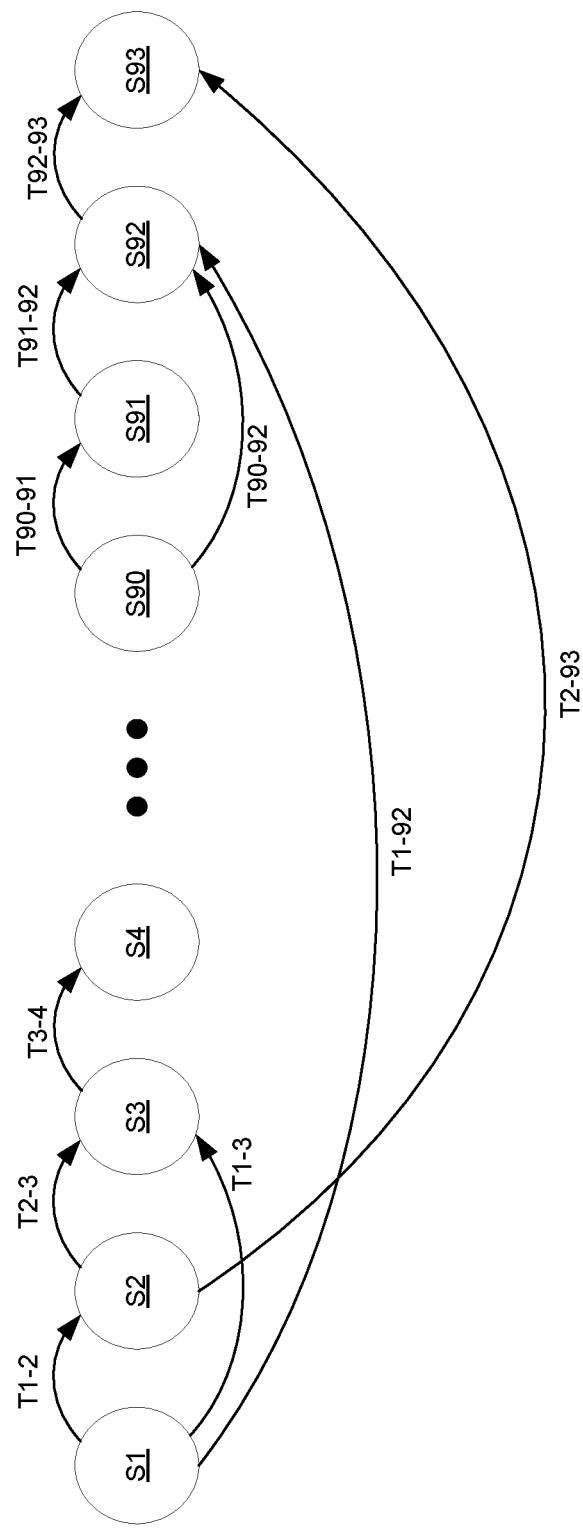
FIG. 1B illustrates a sequence of transformations for registering together intraoral scans of a dental arch, in accordance with embodiments of the present disclosure.

FIG. 1B illustrates a sequence of transformations T1-2, T2-3, T3-4, through T90-91, T91-92, T92-93 for registering together intraoral scans S1, S2, S3, S4, through S90, S91, S92, S93 of a dental arch, in accordance with embodiments of the present disclosure. As shown, there are many scans S1-S93 (e.g., many hundreds of scans), many of which at least partially overlap with multiple other scans. Transformations include transformations between adjacent in time scans (e.g., T1-2, T2-3, T3-4, etc.) as well as transformations between scans that are not adjacent in time but which at least partially overlap (e.g., T1-3, T90-92). There may be six degrees of freedom between any pair of scans, and a transformation T1-2 to T92-93 may be computed between each pair of overlapping scans in each of the six degrees of freedom (e.g., translations in three axes and rotations about three axes). The transformations T1-2 to T92-93 provide information on how a scan is positioned and oriented relative to another overlapping scan. Additionally, sets of transformations may provide information on how any scan is positioned and oriented to any other scan. To know, for example, how scan S1 is positioned relative to scan S4, the system traverses the set of transformations between S1 and S4 (e.g., T1-2, T2-3 and T3-4). The chain of transformations is generally much longer, more complex and more dense than the simplified chain of transformations that is shown. Additionally, generally there are dense connections, meaning that the connections are not only between immediately preceding and following scans in time for a given scan, but to any scan that had geometric overlap with the given scan (e.g., including transformations T1-3 and T90-92). As mentioned above, each transformation between a pair of scans introduces a small amount of error. Accordingly, the accumulated error between S1 and S93 can be relatively large. However, in embodiments a scan may include a representation of both parts of the jaw at once. Such scans are represented by lines T1-92 and T2-93. Such scans that include data for both features on the near side of the jaw and features on the far side of the jaw dramatically reduce the cumulative error that would otherwise occur between, for example, S1 and S93.

In some embodiments, a first set of intraoral scans is generated of one portion of a dental arch (e.g., a left side of a dental arch) and a second set of intraoral scans is generated of another portion of the dental arch (e.g., a right side of the dental arch). However, there may be insufficient scans that have been captured that enable the system to accurately register or stitch together the first set of intraoral scans with the second set of intraoral scans. Such instances can be avoided in embodiments based on one or more intraoral scans that include both representations of teeth and/or other objects (or portions thereof) in the first portion of the dental arch and representations of teeth and/or objects (or portions thereof) in the second portion of the dental arch, as described in detail herein. A first 3D surface of the first portion of the dental arch may be generated from the first set of intraoral scans, and a second 3D surface of the second portion of the dental arch may be generated from the second set of intraoral scans. Even if there are not sufficient scans to generate a 3D surface of an intervening region between the first 3D surface and the second 3D surface, the first set of intraoral scans (and/or the first 3D surface) may be registered with the second set of intraoral scans (and/or the second 3D surface) in a common reference frame using the one or more intraoral scans that depict both surfaces on the first portion of the dental arch and surfaces on the second portion of the dental arch. This may enable a user to scan a first region of a dental arch, then scan a second region of the dental arch that has no overlap with the first region of the dental arch, and generate 3D surfaces of the first and second regions of the dental arch without dropping intraoral scans due to an inability to register them with one another. In embodiments, an intraoral scan depicting two non-adjacent or otherwise disconnected regions of a dental arch can be used to register together intraoral scans that are otherwise unconnected, resulting in two non-connected 3D surfaces (e.g., surfaces of non-adjacent teeth and/or teeth on opposing sides of a dental arch) with a known position and orientation relative to one another.

Figure 1C:
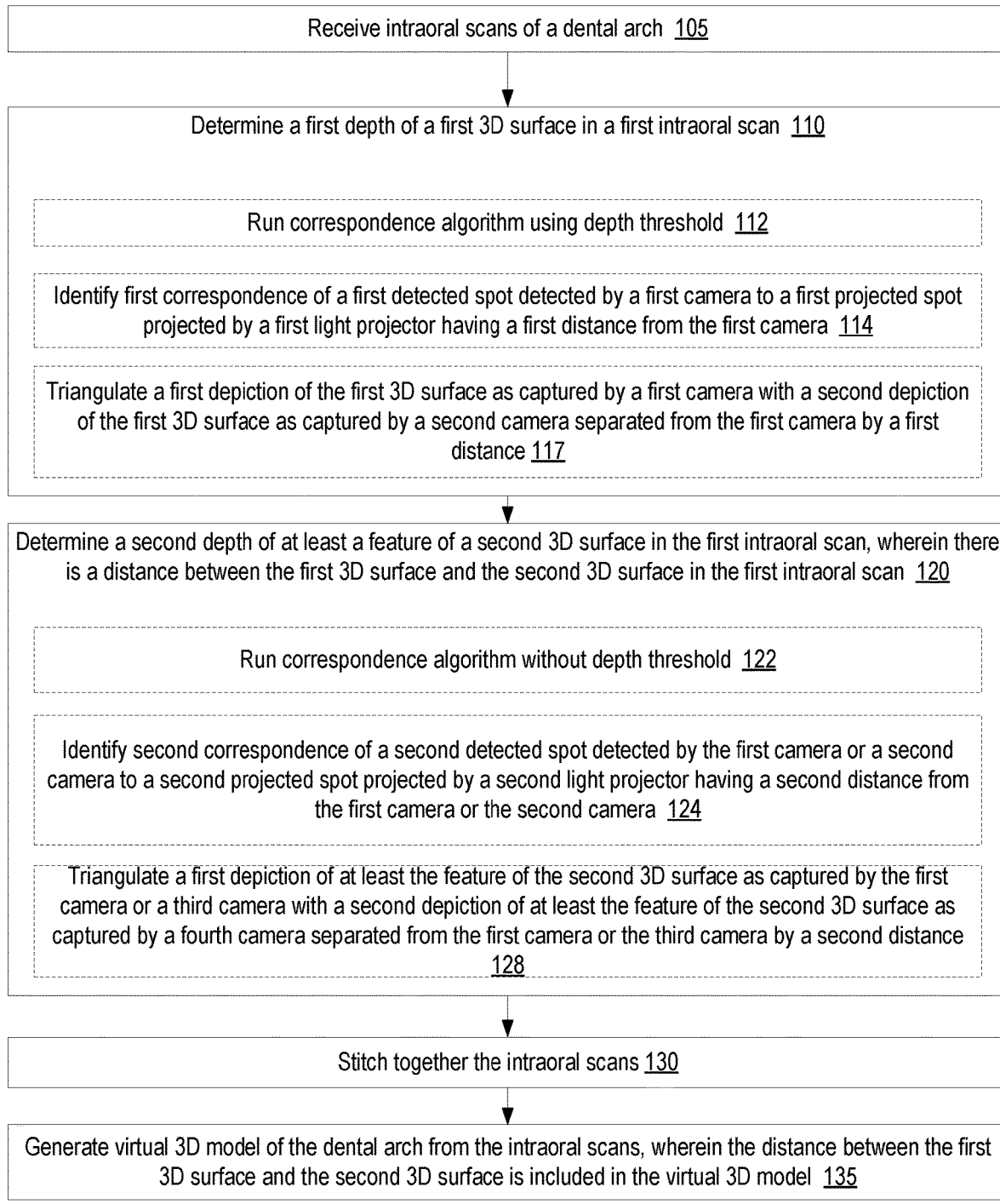
FIG. 1C illustrates a flow diagram for a method of generating a virtual 3D model of a dental arch, in accordance with embodiments of the present disclosure.

FIG. 1C illustrates a flow diagram for a method 101 of generating a virtual 3D model of a dental arch, in accordance with embodiments of the present disclosure. Method 101 may be performed by processing logic that comprises hardware (e.g., circuitry, dedicated logic, programmable logic, microcode, etc.), software (such as instructions run on a processing device), or a combination thereof. In one embodiment, processing logic is computing device 305 of FIG. 3. In some embodiments, some aspects of the method 101 may be performed by an intraoral scanner (e.g., scanner 350 of FIG. 3), while other aspects of method 101 are performed by a computing device that may be operatively coupled to an intraoral scanner (e.g., computing device 305 of FIG. 3). The computing device may be a local computing device that is connected to the intraoral scanner via a wired connection or via a wireless connection. Alternatively, the computing device may be a remote computing device that connects via a network (e.g., the Internet and/or an intranet) to the intraoral scanner or to a local computing device that is in turn connected to the intraoral scanner.

At block 105 of method 101, processing logic receives a plurality of intraoral scans of a dental arch. Each intraoral scan may include image data generated by multiple cameras of an intraoral scanner. In an example, two or more cameras of an intraoral scanner may each generate an intraoral image, and the multiple intraoral images may be combined based on the known positions and orientations of the respective two or more cameras to form an intraoral scan. In one embodiment, each intraoral scan may include captured spots that were projected onto a region of the dental arch by one or more structured light projectors. For example, one or more structured light projectors may be driven to project a distribution of discrete unconnected spots of light on an intraoral surface, and the cameras may be driven to capture images of the projection. The image captured by each camera may include at least one of the spots. Together the images generated by the various cameras at a particular time may form an intraoral scan. In some embodiments, non-structured light (e.g., non-coherent or white light and/or near-infrared light) is also used to illuminate the dental arch.

Each camera may include a camera sensor that has an array of pixels, for each of which there exists a corresponding ray in 3-D space originating from the pixel whose direction is towards an object being imaged; each point along a particular one of these rays, when imaged on the sensor, will fall on its corresponding respective pixel on the sensor. As used throughout this application, the term used for this is a "camera ray." Similarly, for each projected spot from each projector there exists a corresponding projector ray. Each projector ray corresponds to a respective path of pixels on at least one of the camera sensors, i.e., if a camera sees a spot projected by a specific projector ray, that spot will necessarily be detected by a pixel on the specific path of pixels that corresponds to that specific projector ray. Values for (a) the camera ray corresponding to each pixel on the camera sensor of each of the cameras, and (b) the projector ray corresponding to each of the projected spots of light from each of the projectors, may be stored as calibration data, as described hereinbelow.

A dental practitioner may have performed intraoral scanning of the dental arch to generate the plurality of intraoral scans of the dental arch. This may include performing intraoral scanning of a partial or full mandibular or maxillary arch, or a partial or full scan of both arches. Performing the intraoral scanning may include projecting a pattern of discrete unconnected spots onto an intraoral surface of a patient using one or more light projectors disposed in a probe at a distal end of an intraoral scanner, wherein the pattern of discrete unconnected spots is non-coded. Performing the intraoral scanning may further include capturing a plurality of scans or images of the projected pattern of unconnected spots using two or more cameras disposed in the probe.

At block 110, processing logic determines a first depth of a first intraoral 3D surface in a first intraoral scan of the plurality of intraoral scans. The first depth may be determined using a correspondence algorithm and stored calibration values. The stored calibration values may associate camera rays corresponding to pixels on a camera sensor of each of a plurality of cameras to a plurality of projector rays.

Processing logic may run the correspondence algorithm using the stored calibration values in order to identify a three-dimensional location for each projected spot on a surface of a scanned 3D surface (e.g., the first intraoral 3D surface). For a given projector ray, the processor "looks" at the corresponding camera sensor path on one of the cameras. Each detected spot along that camera sensor path will have a camera ray that intersects the given projector ray. That intersection defines a three-dimensional point in space. The processor then searches among the camera sensor paths that correspond to that given projector ray on the other cameras and identifies how many other cameras, on their respective camera sensor paths corresponding to the given projector ray, also detected a spot whose camera ray intersects with that three-dimensional point in space. As used herein throughout the present application, if two or more cameras detect spots whose respective camera rays intersect a given projector ray at the same three-dimensional point in space, the cameras are considered to "agree" on the spot being located at that three-dimensional point. Accordingly, the processor may identify three-dimensional locations of the projected pattern of light based on agreements of the two or more cameras on there being the projected pattern of light by projector rays at certain intersections. The process is repeated for the additional spots along a camera sensor path, and the spot for which the highest number of cameras "agree" is identified as the spot that is being projected onto the surface from the given projector ray. A three-dimensional position on the surface is thus computed for that spot, including the depth for that spot. Accordingly, a depth of a first intraoral 3D surface may be determined (which may include depths of multiple different points on the surface of the first intraoral 3D surface). In one embodiment, the first depth of the first intraoral 3D surface is about 0-5 mm.

Once a position on the surface is determined for a specific spot, the projector ray that projected that spot, as well as all camera rays corresponding to that spot, may be removed from consideration and the correspondence algorithm may be run again for a next projector ray. This may be repeated until depths are determined for many or all spots. Ultimately, the identified three-dimensional locations may be used to generate a digital three-dimensional model of the intraoral surface.

At block 120, processing logic determines a second depth of a second intraoral 3D surface in the first intraoral scan. The second depth may be determined using the correspondence algorithm and the stored calibration values. In one embodiment, the second depth of the second intraoral 3D surface is about 40-90 mm. Alternatively, the second depth may be about 10 mm or more, about 20 mm or more, about 30 mm or more, or some other depth value. For example, the first intraoral 3D surface may be a first tooth or a first scan body on the first half of the dental arch, which may have a depth of about 0-30 mm, or 5-30 mm, or 10-35 mm, or 10-20 mm, etc. from the cameras of the intraoral scanner. The second intraoral 3D surface may be a second tooth or a second scan body on the second half of the dental arch, which may have a depth of about 40-90 mm, or 35-80 mm, or 40-60 mm, or 31-80 mm, etc. In one embodiment, the distance between the first 3D surface and the second 3D surface is greater than 30 mm. For a child's jaw, the first intraoral 3D surface (e.g., of a first tooth or first scan body) on the first half of the dental arch may have a depth of about 0-20 mm, and the second intraoral 3D surface (e.g., of a second tooth or second scan body) on the second half of the dental arch may have a depth of about 21-40 mm. The first intraoral scan may include a buccal view of the first intraoral 3D surface, and may include a lingual view of the second intraoral 3D surface, for example. Since the first intraoral 3D surface and the second intraoral 3D surface are captured by a single intraoral scan, a determined distance between the first intraoral 3D surface and the second intraoral 3D surface may be determined and fixed. This fixed distance may then be used to increase an accuracy of an intermolar width in a 3D model generated from the intraoral scans.

In one embodiment, at block 112 the correspondence algorithm is run using a depth threshold. The depth threshold may be, for example, 5 mm, 10 mm, 15 mm, 20 mm, 25 mm, 30 mm, or another value. In embodiments, the correspondence algorithm may be run multiple times, each time with different depth thresholds. The correspondence algorithm may discard or filter out from consideration possible depth values that are greater than the depth threshold for any of the points. Generally, most or all depth values will be less than the depth threshold. By failing to consider depth values of greater than the depth threshold for points, the computation of depths for spots may be considerably reduced, which may speed up operation of the correspondence algorithm.

For some intraoral scans, such as those that capture points or 3D surfaces on a near half or haft of a dental arch as well as additional points or 3D surfaces on a far half or half of the dental arch, there may be points for which the depth value is greater than the threshold. Accordingly, at block 122, the correspondence algorithm may be rerun without the depth threshold. Running the correspondence algorithm with the depth threshold may have enabled the depths of the spots on the first intraoral 3D surface to be detected, but may have excluded the detection of depths of spots on the second intraoral 3D surface. Accordingly, by rerunning the correspondence algorithm without use of the depth threshold, those spots that depict the second intraoral 3D surface may be reconsidered and their depths that are greater than the depth threshold may be determined. In some embodiments, after running the correspondence algorithm with the depth threshold at block 112, the depths of all spots (or a threshold number of spots) is determined, and the operations of block 120 and 122 are not performed. Alternatively, in some embodiments a determination is made at the end of block 110 or 112 that there are remaining spots with undetermined depths, arid the operations of blocks 120 and/or 122 may be performed.

In one embodiment, at block 114 processing logic determines a first correspondence of a first detected spot detected by a first camera to a first projected spot projected by a first light projector having a first distance from the first camera. The first correspondence may be determined based on running the correspondence algorithm at block 112, for example. In one embodiment, at block 124 processing logic further determines a second correspondence of a second detected spot detected by the first camera or a second camera to a second projected spot projected by a second light projector having a second distance from the first camera or the second camera. The second distance between the first camera or second camera and the second light projector may be greater than the first distance between the first camera and the first light projector. In an example, since the first intraoral 3D surface is closer than the second intraoral 3D surface to the cameras of the intraoral scanner, the first intraoral 3D surface may be within the FOV of a different pair of cameras and light projectors than the second intraoral 3D surface, This is described in greater detail and shown with reference to FIG. 5B.

In some embodiments, the first depth of the first intraoral 3D surface and the second depth of the second intraoral 3D surface is determined without the use of structured light. For example, non-structured or white light may be used to illuminate an oral cavity during intraoral scanning. Multiple cameras may capture images of the same intraoral 3D surfaces for an intraoral scan, and stereo imaging techniques may be used to determine the depths of those intraoral 3D surfaces. In such an embodiment, at block 117 processing logic may triangulate a first depiction of the first intraoral 3D surface as captured by a first camera with a second depiction of the first intraoral 3D surface as captured by a second camera. The second camera may be separated from the first camera by a first distance. The triangulation may be performed to determine the first depth of the first intraoral 3D surface. At block 128, processing logic may additionally triangulate a first depiction of the second intraoral 3D surface as captured by the first camera or a third camera with a second depiction of the second intraoral 3D surface as captured by a fourth camera separated from the first camera or the third camera by a second distance. The second distance may be greater than the first distance. In an example, since the first intraoral 3D surface is closer than the second intraoral 3D surface to the cameras of the intraoral scanner, the first intraoral 3D surface may be within the FOV of a different pair of cameras than the second intraoral 3D surface.

Operations 110-120 may be performed for each of the remaining intraoral scans of the plurality of received intraoral scans.

At block 130, processing logic stitches together the plurality of intraoral scans. This may include registering the first intraoral scan to one or more additional intraoral scans using overlapping data between the various intraoral scans. In one embodiment, performing scan registration includes capturing 3D data of various points of a surface in multiple intraoral scans, and registering the intraoral scans by computing transformations between the intraoral scans. The intraoral scans may then be integrated into a common reference frame by applying appropriate transformations to points of each registered intraoral scan.

In one embodiment, surface registration is performed for adjacent or overlapping intraoral scans (e.g., successive frames of an intraoral video). Surface registration algorithms are carried out to register two or more intraoral scans that have overlapping scan data, which essentially involves determination of the transformations which align one scan with the other. Each registration between scans may be accurate to within 10-15 microns in embodiments in an embodiment. Surface registration may be performed using, for example, an iterative closest point (ICP) algorithm, and may involve identifying multiple points in multiple scans (e.g., point clouds), surface fitting to the points of each scan, and using local searches around points to match points of the overlapping scans. Some examples of ICP algorithms that may be used are described in Francois Pomerleau, et al., "Comparing ICP Variants on Real-World Data Sets", 2013, which is incorporated by reference herein. Other techniques that may be used for registration include those based on determining point-to-point correspondences using other features and minimization of point-to-surface distances, for example. in one embodiment, scan registration (and stitching) is performed as described in U.S. Pat. No. 6,542,249, issued Apr. 1, 2003, entitled "Three-dimensional Measurement Method and Apparatus," which is incorporated by reference herein. Other scan registration techniques may also be used.

Surface registration may include both stitching pairs of intraoral scans sequentially, as well as performing a global optimization that minimizes all pairs of positions together and/or minimizes all points from all scans one to another. Accordingly, if a scan to scan registration (e.g., using ICP) searches in 6 degrees of freedom (3 translation and 3 rotation) that optimizes the distance of all points from one scan to another, then a global optimization of 11 scans will search in (11−1)×6=60 degrees of freedom for all scans relative to all other scans, while minimizing some distance between all scans. In some cases, this global optimization should give weights to different errors (e.g., edges of scans and/or far points may be given lower weight for better robustness).

A special condition may arise when features (e.g., lines or points) that are less than a surface are to be registered to a surface. Assume that in one scan a feature point of a surface (e.g., a corner of a scan body) is captured, and in another scan the surface that includes the feature point is captured. In the ICP, points from one surface to another are minimized, but the point correspondence step of the ICP can change in each iteration. In a variant algorithm, a fixed correspondence may be found between the feature point (e.g., of a feature of a surface) and the surface points (e.g., of a surface), and try to minimize it together with all the surface minimization. As the feature may be a single point or a few points, and may be overwhelmed by the majority of surface points, the error of this feature point will receive a high weight in the global error. In embodiments, a single scan may capture a first surface (e.g., a buccal surface of a near tooth or scan body) and may additionally capture a second surface (e.g., a lingual surface of a far tooth or scan body) or a feature (e.g., one or more points and/or lines) of the second surface. This information may be used to perform registration of the first surface with surfaces of other scans and to perform registration of the second surface (or feature of the second surface) with surfaces of other scans.

At block 135, processing logic generates a virtual 3D model of the dental arch from the intraoral scans. This may include integrating data from all intraoral scans into a single 3D model by applying the appropriate determined transformations to each of the scans. Each transformation may include rotations about one to three axes and translations within one to three planes, for example.

The fixed distance between the first intraoral 3D surface and the second intraoral 3D surface as determined from the first intraoral scan may be included in the virtual 3D model, which may vastly increase an accuracy of the intraoral width for the 3D model of the dental arch as opposed to 3D models of dental arches generated using traditional intraoral scans that do not include image data for 3D surfaces on both a near and far half of a dental arch (quadrant of a jaw) in a single scan.

For some applications, there is at least one uniform light projector (also referred to as a non-coherent light projector) that projects non-coherent light. The uniform light projector transmits white light onto an object being scanned in an embodiment. At least one camera captures two-dimensional color images of the object using illumination from the uniform light projector. Processing logic may run a surface reconstruction algorithm that combines at least one image captured using illumination from structured light projectors with one or more images captured using illumination from a uniform light projector in order to generate a digital three-dimensional image of the intraoral three-dimensional surface. Using a combination of structured light and uniform illumination enhances the overall capture of the intraoral scanner and may help reduce the number of options that processing logic needs to consider when running the correspondence algorithm. In one embodiment, stereo vision techniques, deep learning techniques (e.g., using convolutional neural networks) and/or simultaneous localization and mapping (SLAM) techniques may be used with the scan data from the structured light and the scan data from the non-coherent light to improve an accuracy of a determined 3D surface and/or to reduce a number of options that processing logic needs to consider when running the correspondence algorithm.

For some applications, there is at least one near-infrared light projector that projects near-infrared and/or infrared light onto an object while the object is being scanned. At least one camera captures images of the object using illumination from near-infrared light projector. Processing logic may run a surface reconstruction algorithm that combines at least one image captured using illumination from structured light projectors with one or more images captured using illumination from a near-infrared light projector in order to generate a digital three-dimensional image of the intraoral three-dimensional surface. Using a combination of structured light and near-infrared illumination enhances the overall capture of the intraoral scanner and may help reduce the number of options that processing logic needs to consider when running the correspondence algorithm. In one embodiment, stereo vision techniques, deep learning techniques (e.g., using convolutional neural networks) and/or simultaneous localization and mapping (SLAM) techniques may be used with the scan data from the structured light and the scan data from the near-infrared light to improve an accuracy of a determined 3D surface and/or to reduce a number of options that processing logic needs to consider when running the correspondence algorithm.

In some embodiments, structured light from structured light projectors, non-coherent light from one or more non-coherent light projectors and near-infrared light from one or more near-infrared light projectors is used together.

In embodiments, the dental arch that is scanned may include one or more regions that contain primarily or only soft tissue (e.g., edentulous regions). Conventionally, such an edentulous region may prevent or complicate a successful intraoral scanning operation of the patient because the soft tissue may lack distinctive features (e.g., geometrical features) having a definition that is suitable for performing surface registration (i.e., the tissue contours may be too smooth to allow individual snapshots to be accurately registered to each other). For example, soft tissue may not permit a surface shape measurement that is usable for accurate surface registration or stitching of scans. The edentulous region may be part of a dental site that forms the focus of a particular dental procedure for the patient. For example, a particular procedure may be planned for the dental site, and in some cases an accurate depiction of full mandibular or maxillary arches (including accurate intermolar widths) may be desirable to successfully perform the particular procedure. However, traditionally accurate determination of intermolar widths (e.g., with less than 100 micron of error) has been hard to achieve. Embodiments enable the generation of accurate 3D models of dental arches (with intermolar widths having an error as low as 20 micron), even in cases of edentulous dental arches. Such accurate models may be used for full denture treatment and fully-edentulous implant treatments (including dentures that are supported by multiple implants).

The 3D models of dental arches with improved accuracy that are provided in embodiments may be useful both for prosthodontic (restorative) and orthodontic procedures. By way of non-limiting example, dental procedures may be broadly divided into prosthodontic (restorative) and orthodontic procedures, and then further subdivided into specific forms of these procedures. The term prosthodontic procedure refers, inter alia, to any procedure involving the oral cavity and directed to the design, manufacture or installation of a dental prosthesis at a dental site within the oral cavity, or a real or virtual model thereof, or directed to the design and preparation of the dental site to receive such a prosthesis. A prosthesis may include any restoration such as crowns, veneers, inlays, onlays, and bridges, for example, and any other artificial partial or complete denture. The term orthodontic procedure refers, inter alia, to any procedure involving the oral cavity and directed to the design, manufacture or installation of orthodontic elements at a dental site within the oral cavity, or a real or virtual model thereof, or directed to the design and preparation of the dental site to receive such orthodontic elements. These elements may be appliances including but not limited to brackets and wires, retainers, clear aligners, or functional appliances. One particular procedure for which embodiments of the present disclosure may be particularly useful is an all-on-four procedure. In an at-on-four procedure, a replacement of at teeth is supported on four dental implants. The at-on-four procedure is a prosthodontics procedure for total rehabilitation of an edentulous patient or for patients with badly broken down teeth, decayed teeth, or compromised teeth due to gum disease. An accurate 3D model of a dental arch is particularly important for the at-on-four procedure, but is also particularly difficult to obtain due to lack of distinctive features on the patient's dental arch. Embodiments provided herein enable an accurate 3D model to be generated from an intraoral scanning session that produces intraoral scans of a dental arch that includes four scan bodies, where the 3D model may have an intermolar width with an accuracy of +/−50 μm (or +/−30 μm, +/−20 μm, or +/−10 μm), for example. This enables the all-on-four procedure to be performed with increased accuracy and with reduced failure rates.

Some orthodontic treatments cat for a change in the jaw width (i.e., the intermolar width). Often in conventional intraoral scanning systems, the change in jaw width that is planned may be less than the error associated with intermolar width for a virtual 3D model of a scanned dental arch. In such instances, it is difficult to determine whether the intermolar width is tracking the treatment plan (e.g., whether a planned amount of palatal expansion has been achieved). However, in embodiments the accuracy for the intermolar width is very high, with errors as low as 20 microns.

Accordingly, changes in intermolar width can be tracked over time during orthodontic treatment. In an example, an adult jaw may have a length of about 100 mm and a width of about 50-60 mm. A treatment plan may indicate that the jaw width (intermolar width) should be increased by 100 microns. In a system that has an intermolar width error of over 100 microns, it can be challenging to determine whether the palatal expansion of 100 microns has been successful after treatment. However, in embodiments described herein the amount of palatal expansion can be determined and compared to the planned amount of palatal expansion set forth in the treatment plan.

Figure 1D:
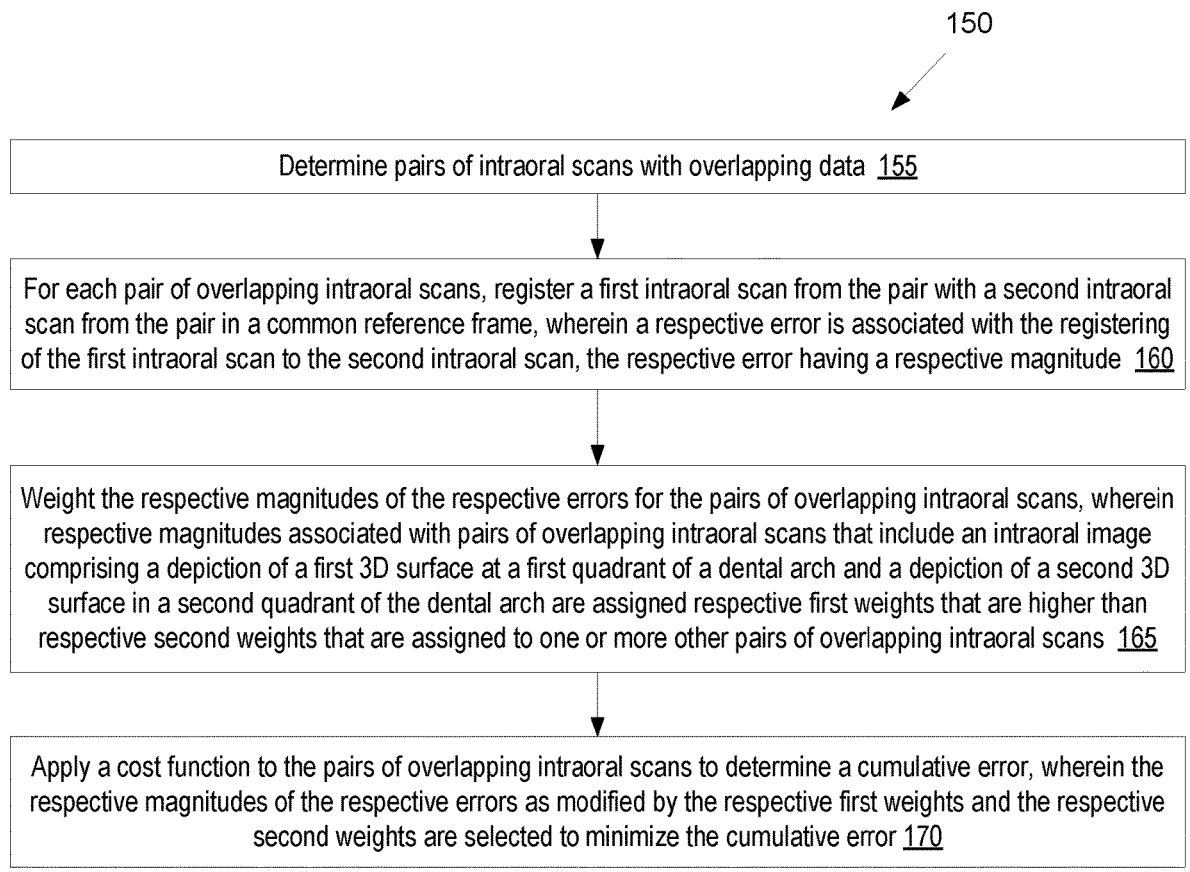
FIG. 1D illustrates a flow diagram for a method of generating a virtual 3D model of a dental arch, in accordance with embodiments of the present disclosure.

FIG. 1D illustrates a flow diagram for a method 150 of generating a virtual 3D model of a dental arch, in accordance with embodiments of the present disclosure. Method 150 may be performed, for example, at blocks 130 and/or 135 of method 101. Method 150 may be performed by processing logic that comprises hardware (e.g., circuitry, dedicated logic, programmable logic, microcode, etc.), software (such as instructions run on a processing device), or a combination thereof. In one embodiment, processing logic is computing device 305 of FIG. 3.

At block 155 of method 150, processing logic determines intraoral scans with overlapping data (e.g., a pair of intraoral scans each depicting a particular intraoral 3D surface). At block 160, for each pair of overlapping intraoral scans, processing logic registers a first intraoral scan from the pair with a second intraoral scan from the pair in a common reference frame. A respective error may be associated with the registering of the first intraoral scan to the second intraoral scan, the respective error having a respective magnitude.

Each registration between a pair of intraoral scans may have some level of inaccuracy, which may be on the order of about 10-15 microns in some embodiments. These registration errors generally add up as a 3D model of a dental arch is generated such that a cumulative error of a width of the 3D model of the dental arch (e.g., intermolar width) has an error on the order or 200-400 microns. A cost function may be applied to the combination of pairs of overlapping intraoral scans to determine the cumulative error. The cost function may be configured to optimize each individual registration to minimize the cumulative error. Generally, the same weight is applied to each registration.

At block 165, processing logic weights the respective magnitudes of the respective errors for the pairs of overlapping intraoral scans. The respective magnitudes associated with pairs of overlapping scans that includes in intraoral image comprising a depiction of a first intraoral 3D surface in a first half of a dental arch and a depiction of a second intraoral 3D surface in a second half of the dental arch may be assigned respective first weights that are higher than respective second weights that are assigned to one or more other pairs of overlapping intraoral scans (e.g., that don't depict both the first and second 3D surface).

At block 170, processing logic applies a cost function to the pairs of overlapping images to assign specific errors to specific registrations between pairs of scans, and to determine the cumulative error. The cost function may use the weighted magnitudes in selecting specific errors to use for each individual registration. In embodiments, the respective magnitudes of the respective errors as modified by the respective first weights and the respective second weights are selected to minimize the cumulative error.

Figure 2A:
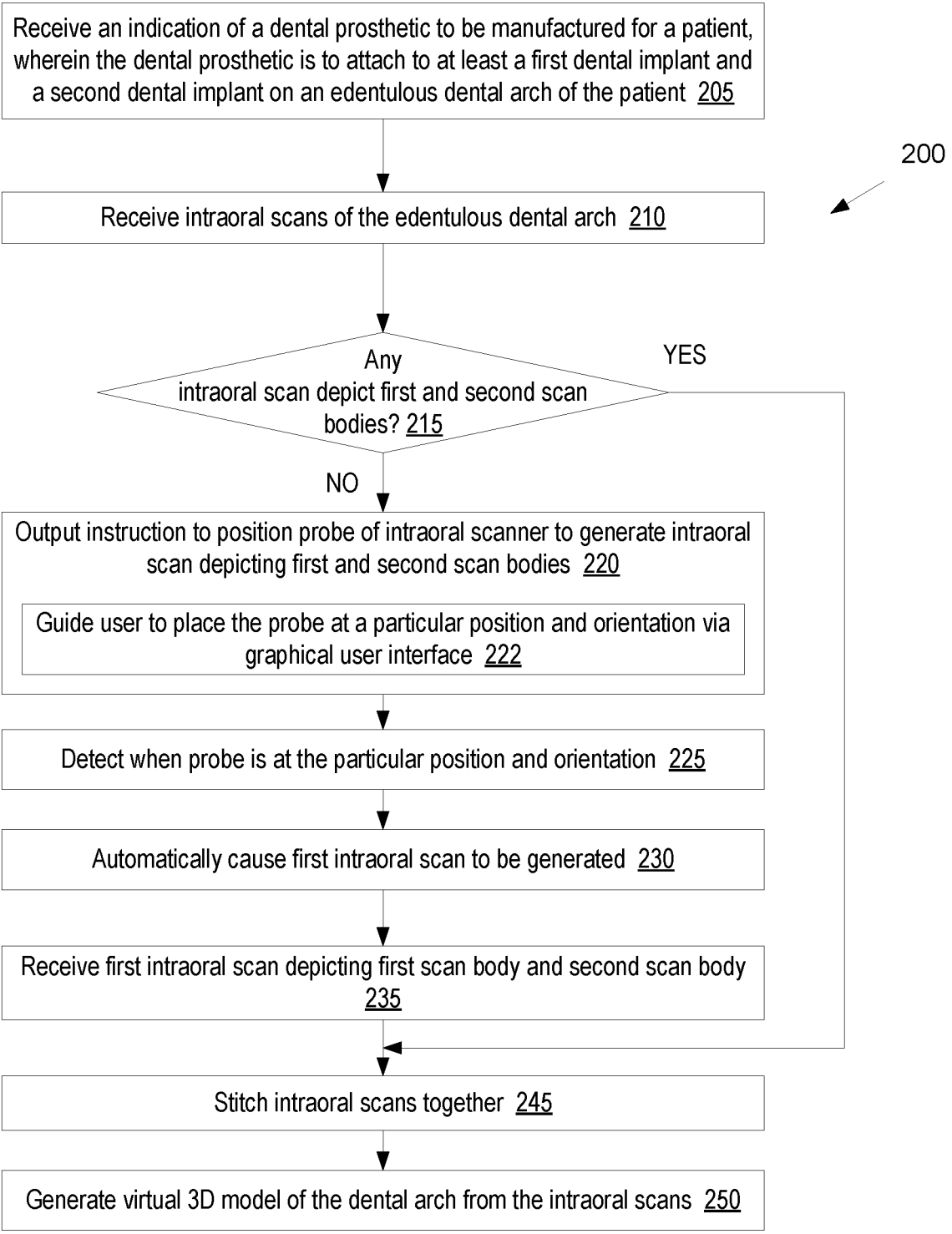
FIG. 2A illustrates a flow diagram for a method of generating a virtual 3D model of a dental arch, in accordance with embodiments of the present disclosure.

FIG. 2A illustrates a flow diagram for a method 200 of generating a virtual 3D model of a dental arch, in accordance with embodiments of the present disclosure. Method 200 may be performed by processing logic that comprises hardware (e.g., circuitry, dedicated logic, programmable logic, microcode, etc.), software (such as instructions run on a processing device), or a combination thereof. In one embodiment, processing logic is computing device 305 of FIG. 3. In some embodiments, some aspects of the method 200 may be performed by an intraoral scanner (e.g., scanner 350 of FIG. 3), while other aspects of method 200 are performed by a computing device operatively coupled to an intraoral scanner (e.g., computing device 305 of FIG. 3).

At block 205 of method 200, processing logic may receive an indication of a dental prosthetic to be manufactured for a patient (and/or of a particular orthodontic or prosthodontic procedure to be performed). The dental prosthetic may be configured to attach to at least a first dental implant and a second dental implant, which may be on an edentulous dental arch of the patient. In one embodiment, the procedure is an all-on-four procedure, and the dental prosthetic will be attached to four dental implants on the dental arch. Absent an identification of the particular procedure, a standard scanning procedure may be performed, which may not take into account or emphasize particular intraoral scans, such as those that depict two scan bodies, each of which may be attached to a dental implant. Identification of the particular procedure to be performed may cause an alternate scanning procedure to be performed, and cause method 200 to proceed.

Processing logic may identify spatial relationships that are suitable for scanning the dental site so that complete and accurate image data may be obtained for the procedure in question. Processing logic may establish an optimal manner for scanning the dental arch. This may include determining specific intraoral scans that should be generated, where each specific intraoral scan should include depictions of multiple specific scan bodies. Further, processing logic may compute an optimal placement for the intraoral scanner to generate the specific intraoral scans. Processing logic may then identify to a dental practitioner one or more locations (e.g., the optimal placement) and/or orientations at which the intraoral scanner is to be placed to generate these intraoral scans. Processing logic may take into consideration a field of view (including depth of focus) of an intraoral scanner to be used when recommending locations at which intraoral scans should be generated to ensure that scan registration will be successful.

A scanning protocol may be identified or determined by relating the type of scanner, resolution thereof, capture area at an optimal spacing between the scanner head and the dental surface to the target area, etc. The scanning protocol may include, for example, a series of scanning stations spatially associated with the dental surfaces of the target area.

At block 210, processing logic receives intraoral scans of the edentulous dental arch. In one embodiment, processing logic analyzes each of the received intraoral scans to determine if any of the intraoral scans include depictions of two or more scan bodies. In one embodiment, if an intraoral scan that includes a depiction of two or more scan bodies is received, processing logic generates a notification for a user. This may include an audible indication (e.g., a ping), a haptic indication, a visual indication (e.g., a message on a screen), and so on. In one embodiment, a scanning procedure to be performed includes a set of scans that each include representations of a particular pair of scan bodies. A graphical user interface (GUI) may show each of these specified scans. As each such specified intraoral scan is received, the GUI may be updated to show that that particular scan has been received.

At block 215, processing logic determines whether any of the intraoral scans depicts a first scan body and a second scan body. Processing logic may have identified a particular scanning station (with a particular position and orientation of the intraoral scanner), and the generation of an intraoral scan at that particular scanning station may generate an intraoral scan depicting the first and second scan bodies. If no intraoral scan depicting the first and second scan bodies is identified, the method continues to block 220. If such an intraoral scan depicting the first and second scan bodies is identified, the method proceeds to block 245.

At block 220, processing logic outputs an instruction to position a probe of the intraoral scanner to generate an intraoral scan depicting the first and second scan bodies. This may include at block 222 guiding a user to place the probe at a particular station (e.g., at a particular position and orientation). The user may be guided via a graphical user interface, for example.

At block 225, processing logic may detect when the probe is at the particular position and orientation. At block 230, processing logic may automatically cause a first intraoral scan to be generated when the probe is at the particular position and orientation. At block 235, processing logic receives a first intraoral scan depicting the first scan body and the second scan body. In some embodiments, the first scan body and second scan body are each on the same half of a dental arch (quadrant of a jaw). In some embodiments, the first scan body and the second scan body are on opposite halves of the dental arch (quadrants of the jaw).

In embodiments, processing logic may determine multiple different stations from which intraoral scans should be generated. Each station may provide an intraoral scan with a depiction of a different combination of two scan bodies. For example, for an all-on-four procedure, a first station may provide an intraoral scan with a depiction of a first and second scan body, a second station may provide an intraoral scan with a depiction of the second scan body and a third scan body, and a third station may provide an intraoral scan with a depiction of the third scan body and a fourth scan body. A fourth station may provide an intraoral scan with a depiction of the second scan body and the fourth scan body. A fifth station may provide an intraoral scan with a depiction of the first scan body with the third scan body. A sixth station may provide an intraoral scan with a depiction of the first scan body and the fourth scan body. Processing logic may repeat the operations of blocks 215-235 for each of the stations (e.g., for each of the target scans that depict specific pairs of scan bodies).

At block 245, processing logic stitches together the intraoral scans. At block 250, processing logic generates a virtual 3D model of the dental arch from the intraoral scans. Thus, method 200 detects when two or more scan bodies are represented in a single intraoral scan, and uses such intraoral scans that include representations of two or more scan bodies to determine correct positions and spacing between the scan bodies.

Figure 2B:
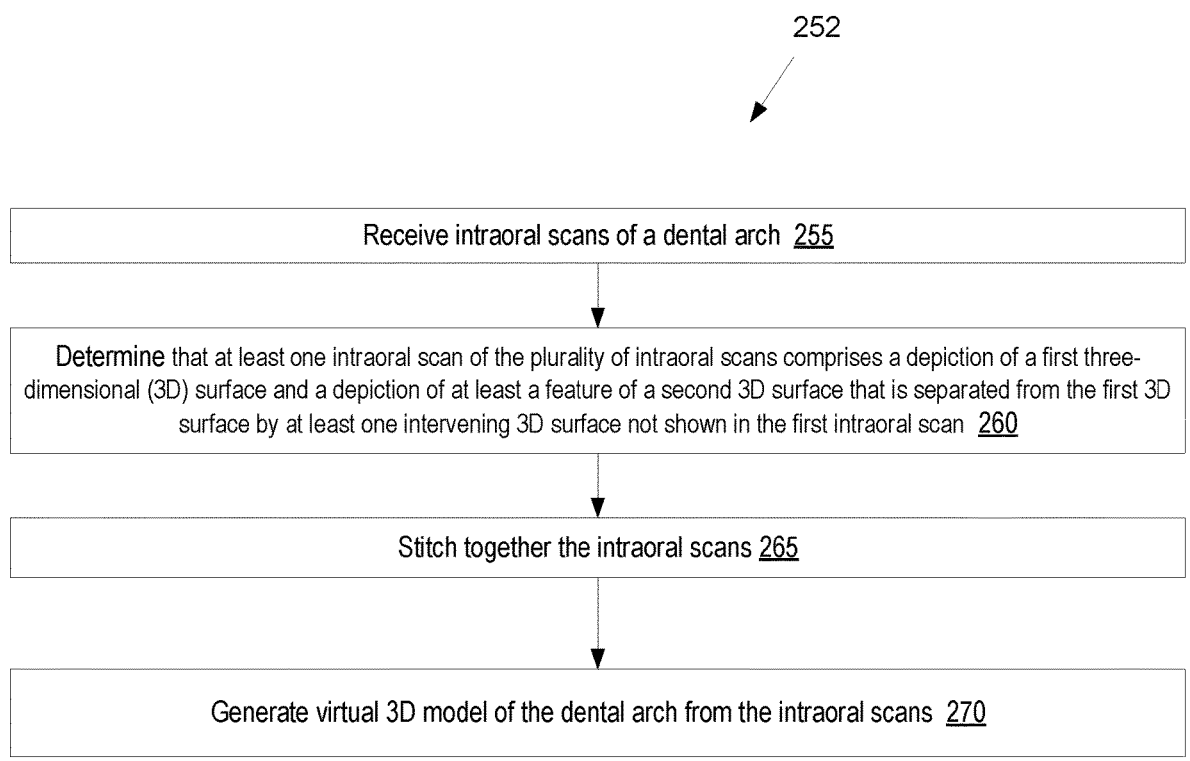
FIG. 2B illustrates a flow diagram for a method of generating a virtual 3D model of a dental arch, in accordance with embodiments of the present disclosure.

FIG. 2B illustrates a flow diagram for a method 252 of generating a virtual 3D model of a dental arch, in accordance with embodiments of the present disclosure. Method 252 may be performed by processing logic that comprises hardware (e.g., circuitry, dedicated logic, programmable logic, microcode, etc.), software (such as instructions run on a processing device), or a combination thereof. In one embodiment, processing logic is computing device 305 of FIG. 3. In some embodiments, some aspects of the method 252 may be performed by an intraoral scanner (e.g., scanner 350 of FIG. 3), while other aspects of method 252 are performed by a computing device operatively coupled to an intraoral scanner (e.g., computing device 305 of FIG. 3).

At block 255 of method 252, processing logic receives a plurality of intraoral scans of a dental arch. Each intraoral scan may include image data generated by multiple cameras of an intraoral scanner. In an example, two or more cameras of an intraoral scanner may each generate an intraoral image, and the multiple intraoral images may be combined based on the known positions and orientations of the respective two or more cameras to form an intraoral scan. A dental practitioner may have performed intraoral scanning of the dental arch to generate the plurality of intraoral scans of the dental arch. This may include performing intraoral scanning of a partial or full mandibular or maxillary arch, or a partial or full scan of both arches.

At block 260, processing logic determines that at least one intraoral scan of the plurality of intraoral scans comprises a depiction of a first three-dimensional (3D) surface and a depiction of at least a feature of a second 3D surface that is separated from the first 3D surface by at least one intervening 3D surface not shown in the at least one intraoral scan. There may be a distance between the first 3D surface and the feature of the second 3D surface in the at least one intraoral scan. In one embodiment, the at least one intraoral scan includes a buccal view of the first 3D surface and a lingual view of at least a feature of the second 3D surface that is not connected to the first 3D surface in the at least one intraoral scan. Though the first and second 3D surfaces are not connected in the at least one intraoral scan, it should be noted that the first and second 3D surfaces may be physically connected on a patient's jaw. However, that physical connection may not be shown in the intraoral scan. For example, the first 3D surface may be on a near quadrant of the dental arch, and the second 3D surface may be on a far quadrant of the dental arch, but a portion of the dental arch connecting the first 3D surface and the second 3D surface may not be shown. In one embodiment, the dental arch is an edentulous dental arch comprising a plurality of scan bodies, the first 3D surface represents at least a portion of a first scan body of the plurality of scan bodies, the at least one intervening 3D surface represents a second scan body of the plurality of scan bodies, and the second 3D surface represents at least a portion of a third scan body of the plurality of scan bodies.

In one embodiment, the intraoral scanner that generates the intraoral scans may be as described in greater detail below. In one embodiment, the intraoral scanner has multiple cameras with different focal depth ranges or settings. In one embodiment, the first intraoral scan is a buccal scan, and the first 3D surface and second 3D surface are at different depths in the buccal scan (e.g., as described with reference to FIG. 1B). For example, the largest depth of the first 3D surface may be less than the smallest depth of the second 3D surface. In one embodiment, the plurality of intraoral scans are generated by an intraoral scanner having a depth of focus that is greater than 30 mm, wherein the first 3D surface has a depth of less than 30 mm, and wherein the second 3D surface has a depth of greater than 30 mm.

The accuracy of detected points and surfaces may decrease with increased depth in embodiments. Accordingly, the accuracy of the determined depth and/or position of the second 3D surface may be lower than the accuracy of the determined depth and/or position of the first 3D surface. In some embodiments, the second 3D surface is a scan body with a known 3D geometry. Accordingly, the second 3D surface (or detected features of the second 3D surface) may be compared to the known geometry of the scan body to determine that the 3D surface is the scan body. The known geometry of the scan body may then be used to improve an accuracy of the depth and/or position of the second 3D surface.

Alternatively, the first intraoral scan may be an occlusal scan, and the first 3D surface and second 3D surface may have similar depths (e.g., may have depths of less than 30 mm) but different x,y positions. In one embodiment, the intraoral scanner that generates the intraoral scans may be as described in greater detail below. Alternatively, the intraoral scanner may not have a large range of depth of focus, and may instead have a large FOV in the x, y axes. Such an intraoral scanner may use, for example, one or more cameras, light projectors, fish eye cameras, etc. to generate scans. The FOV of the intraoral scanner may be one large FOV (e.g., including overlapping FOVs of multiple cameras) or may be two or more disconnected FOVs (e.g., including FOVs that are not overlapping from two or more cameras that are separated laterally). In an example, the first intraoral scan may have a length of 30 microns, and the first 3D surface may be at one extreme of the length and the second 3D surface may be at a second extreme of the length (e.g., at opposite ends of the 3D scan). In one embodiment, the plurality of intraoral scans are generated by an intraoral scanner having a lateral field of view of greater than 30 mm, wherein the first 3D surface is at a first side of the field of view, and wherein the second 3D surface is at a second side of the field of view.

At block 265, processing logic stitches together the plurality of intraoral scans. This may include registering the at least one intraoral scan to one or more additional intraoral scans using overlapping data between the various intraoral scans.

At block 270, processing logic generates a virtual 3D model of the dental arch from the intraoral scans. This may include integrating data from all intraoral scans into a single 3D model by applying the appropriate determined transformations to each of the scans. Each transformation may include rotations about one to three axes and translations within one to three planes, for example.

The distance between the first intraoral 3D surface and the second intraoral 3D surface as determined from the at least one intraoral scan may be included in the virtual 3D model, which may vastly increase an accuracy of the intraoral width for the 3D model of the dental arch as opposed to 3D models of dental arches generated using traditional intraoral scans that do not include image data for 3D surfaces on both a near and far half of a dental arch (quadrant of a jaw) in a single scan. As a result of stitching together the plurality of intraoral scans exclusive of the at least one intraoral scan, there may be a first number of links between pairs of intraoral scans that connect the first 3D surface on a first quadrant of the dental arch to the second 3D surface on a second quadrant of the dental arch. As a result of stitching together the plurality of intraoral scans inclusive of the at least one intraoral scan, there are a second number of links between pairs of intraoral scans that connect the first 3D surface on the first quadrant of the dental arch to the second 3D surface on the second quadrant of the dental arch. The second number of links is lower than the first number of links and causes an increased accuracy in the virtual 3D model.

Figure 3:
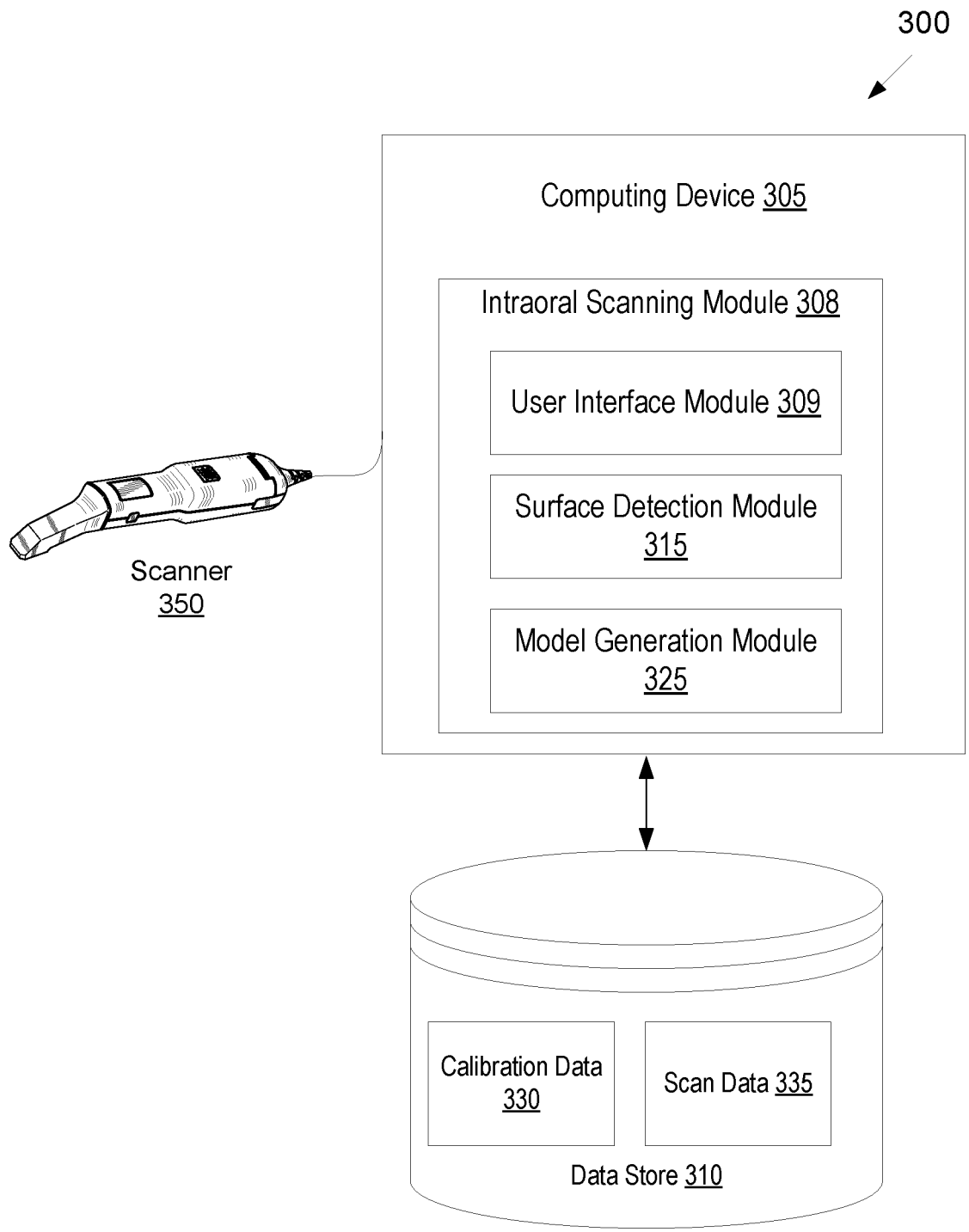
FIG. 3 illustrates one embodiment of a system for performing intraoral scanning and generating a virtual 3D model of a dental arch.

FIG. 3 illustrates one embodiment of a system 300 for performing intraoral scanning and/or generating a virtual 3D model of a dental arch. In one embodiment, system 300 carries out one or more operations of above described methods 101, 150 and/or 200. System 300 includes a computing device 305 that may be coupled to an intraoral scanner 350 (also referred to simply as a scanner 350) and/or a data store 310.

Computing device 305 may include a processing device, memory, secondary storage, one or more input devices (e.g., such as a keyboard, mouse, tablet, and so on), one or more output devices (e.g., a display, a printer, etc.), and/or other hardware components. Computing device 305 may be connected to a data store 310 either directly or via a network. The network may be a local area network (LAN), a public wide area network (WAN) (e.g., the Internet), a private WAN (e.g., an intranet), or a combination thereof. The computing device and the memory device may be integrated into the scanner in some embodiments to improve performance and mobility.

Data store 310 may be an internal data store, or an external data store that is connected to computing device 305 directly or via a network. Examples of network data stores include a storage area network (SAN), a network attached storage (NAS), and a storage service provided by a cloud computing service provider. Data store 310 may include a file system, a database, or other data storage arrangement.

In some embodiments, a scanner 350 for obtaining three-dimensional (3D) data of a dental site in a patient's oral cavity is also operatively connected to the computing device 305. Scanner 350 may include a probe (e.g., a hand held probe) for optically capturing three dimensional structures.

In some embodiments, the scanner 350 includes an elongate handheld wand including a probe at a distal end of the handheld wand; a rigid structure disposed within a distal end of the probe; one or more structured light projectors coupled to the rigid structure (and optionally one or more non-structured light projectors coupled to the rigid structure, such as non-coherent light projectors and/or near-infrared light projectors); and one or more cameras coupled to the rigid structure. In some applications, each light projector may have a field of illumination of 45-120 degrees. Optionally, the one or more light projectors may utilize a laser diode light source. Further, the structure light projector(s) may include a beam shaping optical element. Further still, the structured light projector(s) may include a pattern generating optical element.

The pattern generating optical element may be configured to generate a distribution of discrete unconnected spots of light. The distribution of discrete unconnected spots of light may be generated at all planes located between specific distances (e.g., 1-30 mm, 1-50 mm, 1-80 mm, etc.) from the pattern generating optical element when the light source (e.g., laser diode) is activated to transmit light through the pattern generating optical element. In some applications, the pattern generating optical element utilizes diffraction and/or refraction to generate the distribution. Optionally, the pattern generating optical element has a light throughput efficiency of at least 90%.

For some applications, the light projectors and the cameras are positioned such that each light projector faces an object outside of the wand placed in its field of illumination. Optionally, each camera may face an object outside of the wand placed in its field of view. Further, in some applications, at least 20% of the discrete unconnected spots of light are in the field of view of at least one of the cameras.

The scanner 350 may be used to perform intraoral scanning of a patient's oral cavity. A result of the intraoral scanning may be a sequence of intraoral scans that have been discretely generated (e.g., by pressing on a "generate scan"

button of the scanner for each intraoral scan). Alternatively, a result of the intraoral scanning may be one or more videos of the patient's oral cavity. An operator may start recording the video with the scanner 350 at a first position in the oral cavity, move the scanner 350 within the oral cavity to a second position while the video is being taken, and then stop recording the video. In some embodiments, recording may start automatically as the scanner identifies that it has been positioned at a particular station (e.g., at a particular position and orientation in a patient's oral cavity). In either case, the scanner 350 may transmit the discrete intraoral scans or intraoral video (referred to collectively as scan data 335) to the computing device 305. Note that in some embodiments the computing device may be integrated into the scanner 350. Computing device 305 may store the scan data 335 in data store 310. Alternatively, scanner 350 may be connected to another system that stores the scan data in data store 310. In such an embodiment, scanner 350 may not be connected to computing device 305.

Scanner 350 may drive each one of one or more light projectors to project a distribution of discrete unconnected spots of light on an intraoral three-dimensional surface. Scanner 350 may further drive each one of one or more cameras to capture an image, the image including at least one of the spots. Each one of the one or more cameras may include a camera sensor including an array of pixels. The images captured together at a particular time may together form an intraoral scan. The intraoral scans may be transmitted to computing device 305 and/or stored in data store 310 as scan data 335.

Computing device 305 may include an intraoral scanning module 308 for facilitating intraoral scanning and generating 3D models of dental arches from intraoral scans. Intraoral scanning module 308 may include an surface detection module 315 and a model generation module 325 in some embodiments. Surface detection module 315 may analyze received image data 335 to identify objects in the intraoral scans of the image data 335. Surface detection module may execute a correspondence algorithm on intraoral scans to determine the depths of spots or points in the intraoral scans. The surface detection module 315 may access stored calibration data 330 indicating (a) a camera ray corresponding to each pixel on the camera sensor of each one of the one or more cameras, and (b) a projector ray corresponding to each of the projected spots of light from each one of the one or more projectors, where each projector ray corresponds to a respective path of pixels on at least one of the camera sensors. Using the calibration data 330 and the correspondence algorithm, surface detection module 315 may, (1) for each projector ray i, identify for each detected spot j on a camera sensor path corresponding to ray i, how many other cameras, on their respective camera sensor paths corresponding to ray i, detected respective spots k corresponding to respective camera rays that intersect ray i and the camera ray corresponding to detected spot j. Ray i is identified as the specific projector ray that produced a detected spot j for which the highest number of other cameras detected respective spots k. Surface detection module 315 may further (2) compute a respective three-dimensional position on an intraoral three-dimensional surface at the intersection of projector ray i and the respective camera rays corresponding to the detected spot j and the respective detected spots k. For some applications, running the correspondence algorithm further includes, following operation (1), using the processor to remove from consideration projector ray i, and the respective camera rays corresponding to the detected spot j and the respective detected spots k, and running the correspondence algorithm again for a next projector ray i.

Model generation module 325 may perform surface registration between intraoral scans (e.g., may stitch together the intraoral scans as discussed above). Model generation module 325 may then generate a virtual 3D model of a dental arch from the registered intraoral scans, as discussed above.

In some embodiments, intraoral scanning module 308 includes a user interface module 309 that provides a user interface that may display the generated virtual 3D model. Additionally, user interface module 305 may direct a user to position a probe of the scanner 350 at a particular position and orientation (e.g., a particular station) for generation of a specific intraoral scan.

In some embodiments, at least one intraoral scan included in scan data 335 includes features and/or 3D surfaces on a first side or half of a dental arch and additionally includes features and/or 3D surfaces on a second side or half of the dental arch. In order to generate such an intraoral scan, the probe of the scanner 350 may be positioned at a lingual side of the near half of the dental arch. The probe of the scanner 350 may be oriented so that a longitudinal axis of the probe is approximately parallel to a plane of the dental arch, and so that the buccal side of the near half of the dental arch and the lingual side of the far half of the dental arch are in the FOV of the scanner 350.

Figure 4A:
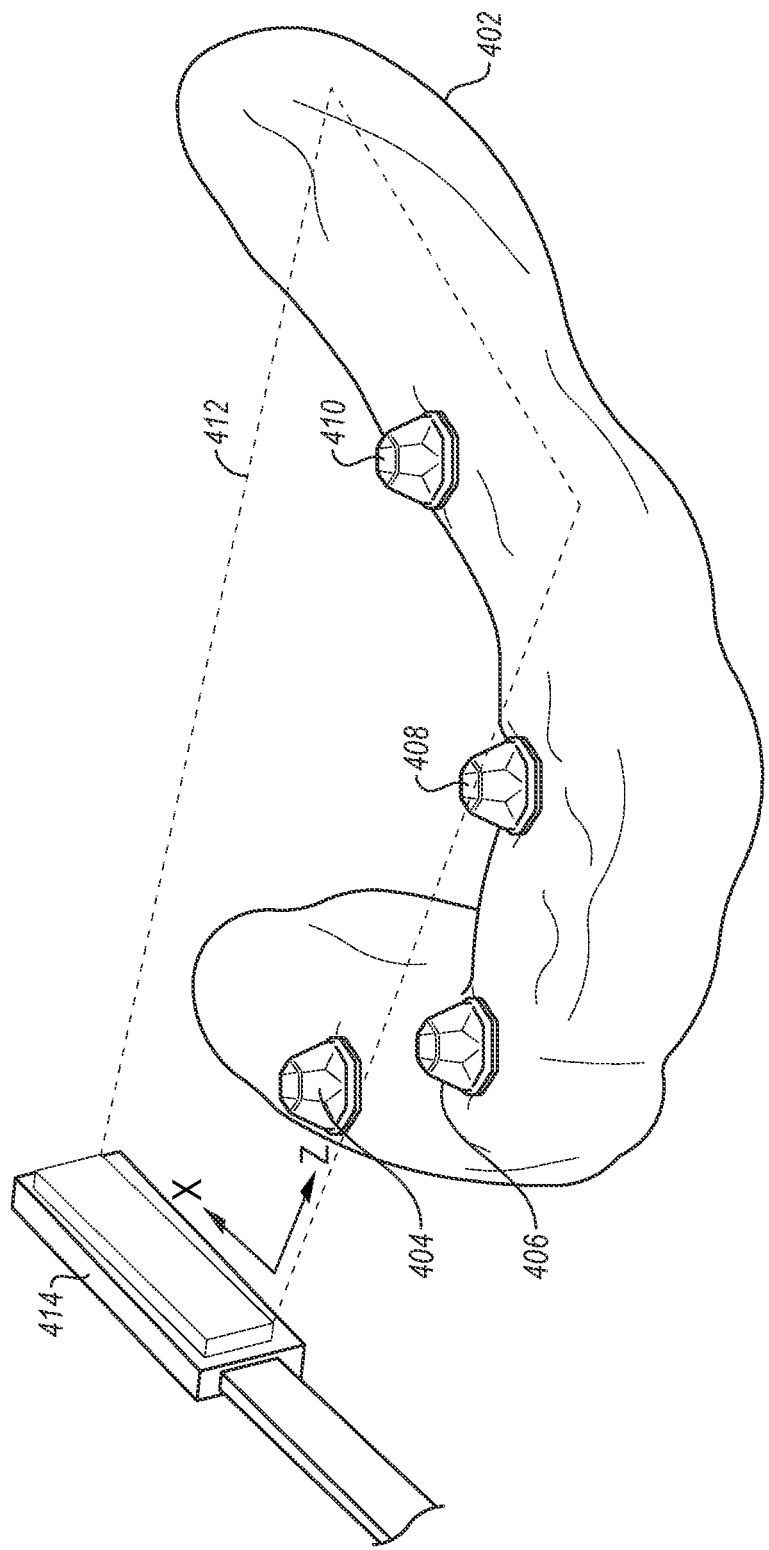
FIG. 4A illustrates an example scan of an edentulous dental arch, in accordance with embodiments of the present disclosure.

FIG. 4A illustrates a single intraoral scan 412 of an edentulous dental arch 402 with a first scan body 404, a second scan body 406, a third scan body 408 and a fourth scan body 410. A probe 414 of an intraoral scanner (e.g., scanner 350) is positioned at the buccal side of the near half of the dental arch 402 and oriented so that a longitudinal axis (x-axis) of the probe is approximately parallel to a plane of the dental arch and the z-axis (depth) of the probe is approximately parallel to the plane of the dental arch. Accordingly, the buccal side of first scan body 404 and the lingual side of the fourth scan body 410 are in the FOV of the probe 414. As shown, the probe 414 may have a FOV that generates an intraoral scan 412 that includes the first scan body 404 and the fourth scan body 410. The x-axis corresponds to the longitudinal axis of the probe 414, and the z-axis corresponds to the depth measured as a distance from the probe 414. The z-axis and x-axis of the intraoral scan 412 are shown, but a y-axis (going into the page) is not shown.

Figure 4B:
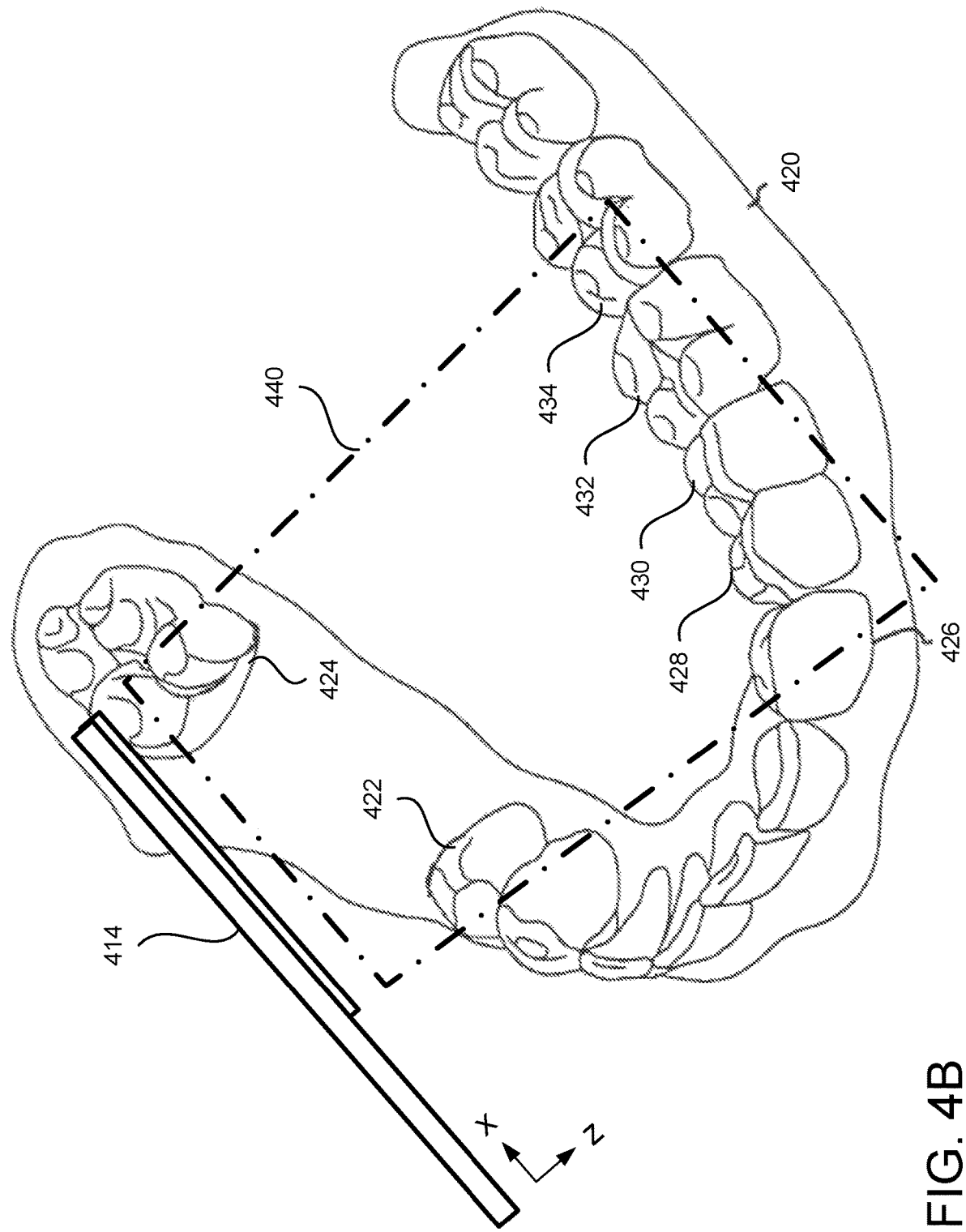
FIG. 4B illustrates an example scan of a dental arch having an edentulous region, in accordance with embodiments of the present disclosure.

FIG. 4B illustrates a single intraoral scan 440 of a dental arch 420 with an edentulous region. The dental arch 420 includes multiple teeth, including tooth 422, tooth 424, tooth 426, tooth 428, tooth 430, tooth 432 and tooth 434. A probe 414 of an intraoral scanner (e.g., scanner 350) is positioned at the buccal side of the near half of the dental arch 420 and oriented so that a longitudinal axis of the probe is approximately parallel to a plane of the dental arch (e.g., x-z plane), and so that the buccal side of teeth 422, 424 and the lingual side of teeth 426-434 are in the FOV of the probe 414. As shown, the probe 414 may have a FOV that generates an intraoral scan 440 that includes near teeth 422, 424 and far teeth 426-434. The x-axis corresponds to the longitudinal axis of the probe 414, and the z-axis corresponds to the depth measured as a distance from the probe 414.

Figure 4C:
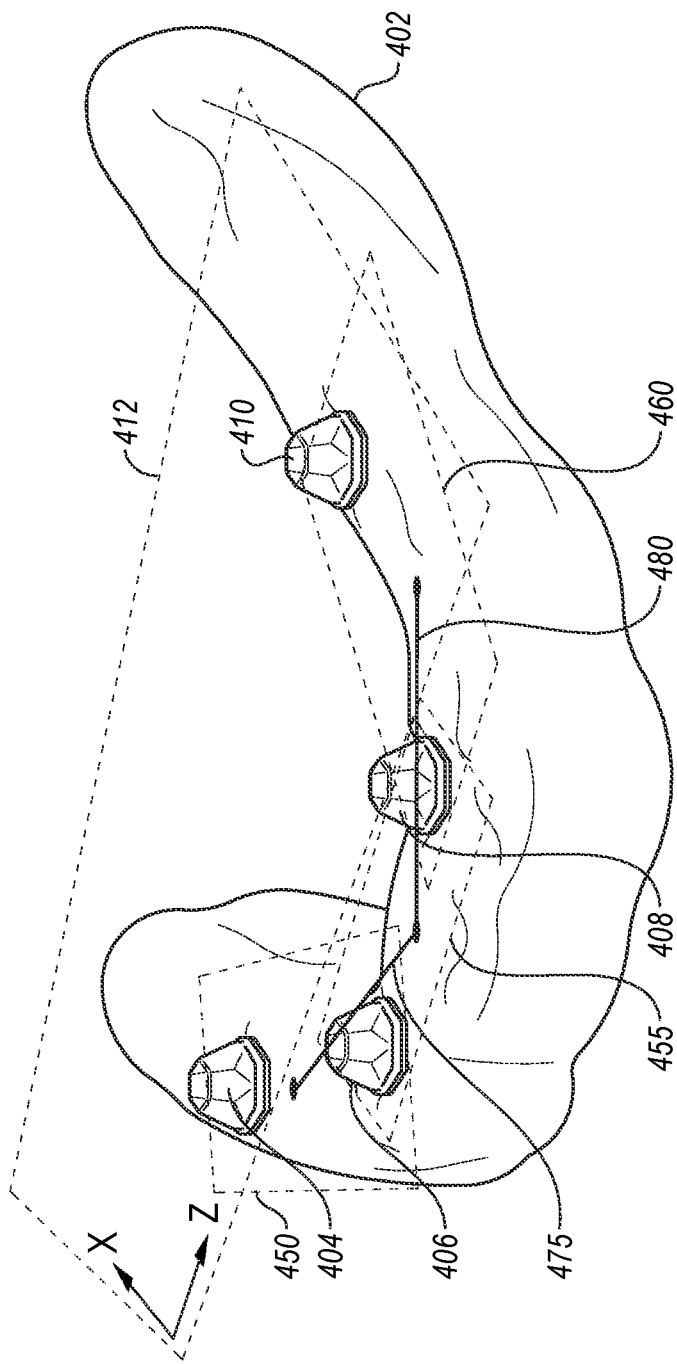
FIG. 4C illustrates multiple example scans of an edentulous dental arch, in accordance with embodiments of the present disclosure.

FIG. 4C illustrates multiple intraoral scans of edentulous dental arch 402 of FIG. 4A. Each of the intraoral scans may have been generated by an intraoral scanner having a particular distance from the dental surface being imaged (e.g., from the dental arch). At the particular distance, the intraoral scans have a particular scan area and scan depth.

The shape and size of the scan area will generally depend on the scanner, and is herein represented by a rectangle. Each scan may have its own reference coordinate system and origin. Each intraoral scan may be generated by a scanner at a particular position (e.g., scanning station). The location and orientation of specific scanning stations may be selected such that specific target scans (e.g., such as intraoral scan 412, and intraoral scans 450, 455, 460) are generated.

Intraoral scan 412 may have been generated while a probe (not shown) of an intraoral scanner (e.g., scanner 350) was positioned at the buccal side of the near half of the dental arch 402 and oriented so that a longitudinal axis (x-axis) of the probe is approximately parallel to a plane of the dental arch and the z-axis (depth) of the probe is approximately parallel to the plane of the dental arch, referred to as a buccal scan. Accordingly, the buccal side of first scan body 432 and the lingual side of the fourth scan body 438 are in the FOV of the probe. The z-axis and x-axis of the intraoral scan 412 are shown, but a y-axis (going into the page) is not shown. Other intraoral scans (not shown) may also have been generated with the x-axis and z-axis of the probe generally parallel to the plane of the dental arch.

Numerous intraoral scans, including intraoral scans 450, 455 and 460, may also be taken with the longitudinal axis of the probe approximately normal to the plane of the dental arch and the z-axis optionally approximately normal to the plane of the dental arch, referred to as an occlusal scan. Accordingly, for intraoral scans 450, 455, 460 the x-axis and the y-axis of the FOV of the scan are shown, but the z-axis of the scan is not shown. For each of intraoral scan 412 and intraoral scans 450, 455, 460, at least two scan bodies are represented. For example, first scan body 404 and second scan body 406 are included in intraoral scan 450, second scan body 406 and third scan body 408 are included in intraoral scan 455, third scan body and fourth scan body 410 are included in intraoral scan 460, and first scan body 404 and fourth scan body 410 are included in intraoral scan 412. These intraoral scans may be stitched together to generate a very accurate virtual 3D model of the dental arch 402 in embodiments.

In some embodiments, intraoral scans that depict two scan bodies may have a higher importance than other intraoral scans for the purpose of building an accurate 3D model of the dental arch. This higher importance can be realized naturally in some algorithms because they include a large number of unique surfaces that are usable to perform accurate scan registration. In other embodiments, such intraoral scans may be detected, and these scans (or links/transformations that include these scans) may be given a higher weight than other intraoral scans during optimization of a computed 3D model of the dental arch.

Surface registration may be performed between each pair of overlapping scans, such as between intraoral scan 450 and intraoral scan 455, and between intraoral scan 455 and intraoral scan 460. For each surface registration operation, a 3D transformation may be computed between a pair of intraoral scans. The 3D transformation can be shown visually as a link between two scans. For example, link 475 between intraoral scan 450 and intraoral scan 455 represents a first transformation, and link 480 between intraoral scan 455 and intraoral scan 460 represents a second transformation. Transformations may also be computed, for example, between intraoral scan 412 and intraoral scan 450 and between intraoral scan 412 and intraoral scan 460, but are not shown for the sake of clarity. When a full jaw is scanned, many such transformations and links may be computed, which may create a chain of links that indirectly connects one side of the dental arch to another side of the dental arch. Each link/transformation may have some small error associated with it, which may accumulate to a large error from side to side, causing a large error in intermolar width. However, use of intraoral scan 412 that depicts both sides of the dental arch can drastically reduce the error in the intermolar width caused by accumulated errors from the combined links/transformations. Any error in the intermolar width that is included in the intraoral scan 412 may be based on an inaccuracy in a depth measurement of the far side of the jaw (e.g., of fourth scan body 410), and is far smaller than the accumulated inaccuracy caused by multiple links across the jaw. The distance between the first scan body 404 (or other feature on the near side of the jaw) and the fourth scan body (or other feature on the far side of the jaw) may be fixed from intraoral scan 412, and may directly provide the intermolar width or may be used to calculate the intermolar width accurately. Each scan may be considered a rigid body, and the distance between 3D surfaces within a scan may be fixed during surface registration and/or generation of a 3D model. When the 3D model is built, processing logic may search for relative positions that would most agree with the distances that were originally determined or found during surface registration. This means optimizing the difference between the stitched scan's original transformations and the final relative positions of the scans determined for the 3D model. In some embodiments, processing logic may detect that some scans include data from both sides or halves of the dental arch, and may give priority to these scans (e.g., may provide a larger weight to these scans or links including these scans during an optimization process).

Any inaccuracy in the depth measurement of the fourth scan body (or other 3D surface with a large depth) may be mitigated by using an intraoral scanner with a large base line between cameras (or between a camera and a light projector), as described below with reference to FIG. 5B.

As discussed herein above, an intraoral scanner set forth in embodiments of the present disclosure is usable to generate intraoral scans that include both scan data of nearby objects (e.g., objects such as teeth or portions of teeth in a nearby quadrant of a dental arch) and scan data of far objects (e.g., objects such as teeth or portions of teeth in a far quadrant of the dental arch). Such scans that include both depictions of nearby objects on a dental arch and depictions of far objects on the dental arch are usable to greatly increase the accuracy of surface registration that is performed to stitch together scans of the dental arch. For example, a scan may include surfaces of a buccal side of a near molar and a lingual side of a far molar, a buccal side of a near molar and a lingual side of a far premolar, a buccal side of a near molar and a lingual side of a far incisor, a buccal side of a near premolar and a lingual side of a far molar, a buccal side of a near premolar and a lingual side of a far premolar, a buccal side of a near premolar and a lingual side of a far incisor, a buccal side of a near incisor and a lingual side of a far molar, a buccal side of a near incisor and a lingual side of a far premolar, and/or a buccal side of a near incisor and a lingual side of a far incisor.

FIGS. 4D-J illustrate some example intraoral scans showing nearby teeth and far teeth in a single scan, which can be used to improve accuracy of surface registration, in accordance with embodiments of the present disclosure. The example intraoral scans were generated using an intraoral scanner as described in embodiments herein. In some of the example intraoral scans, lingual views of one or more teeth, buccal views of one or more teeth and/or occlusal views of one or more teeth are shown.

FIG. 4D illustrates a scan of a buccal side of near teeth 481 (e.g., buccal premolar) that also shows the lingual side of far teeth 482 (e.g., incisor to molar) on the opposite side of the jaw. The occlusal side of one or more of the far teeth 482 is also shown.

FIG. 4E illustrates a scan of a buccal side of near teeth 483 (e.g., buccal incisor) that also shows the lingual side of far teeth 484 (e.g., lingual premolar and molar) on the opposite side of the jaw. The occlusal side of one or more of the far teeth 484 is also shown.

FIG. 4F illustrates a scan of an occlusal view of an incisor 485 (e.g., buccal incisor) on a first side of a dental arch that also shows a number of other teeth on an opposite side of the dental arch, such as the far incisor 486. The occlusal side of one or more of the teeth is also shown.

FIG. 4G illustrates a scan of a buccal view of an incisor 487 that also shows a lingual view of a molar 489 and premolar 488. The occlusal side of one or more of the incisor 487 molar 489 and premolar 488 is also shown.

Figure 4I:
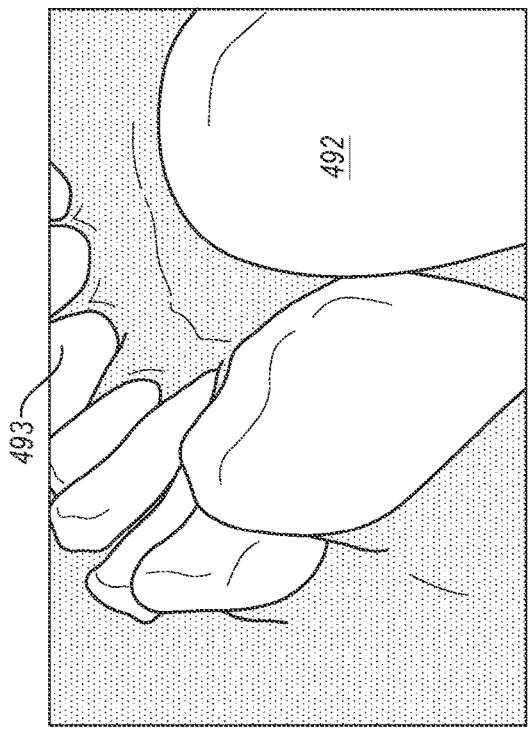
Figure 4J:
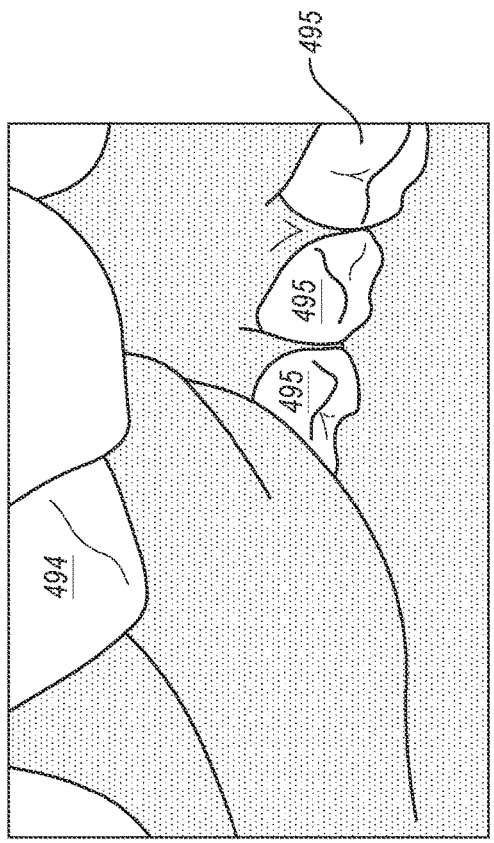
Figure 4H:
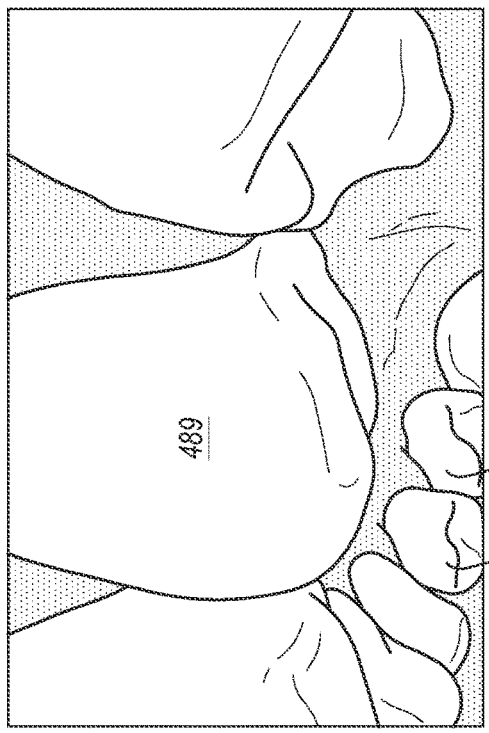

FIG. 4H illustrates a scan of a buccal view and/or occlusal view of a premolar 489 that also shows a lingual view and/or occlusal view of an incisor 490 and premolar 491 on an opposite side of the jaw.

FIG. 4I illustrates a scan showing all of the teeth on a dental arch between and including a near incisor 492 and a far incisor 493.

FIG. 4J illustrates a scan showing the buccal side of near teeth 494 and the lingual side of far teeth 495, which are part of the same dental arch as the near teeth.

Figure 5A:
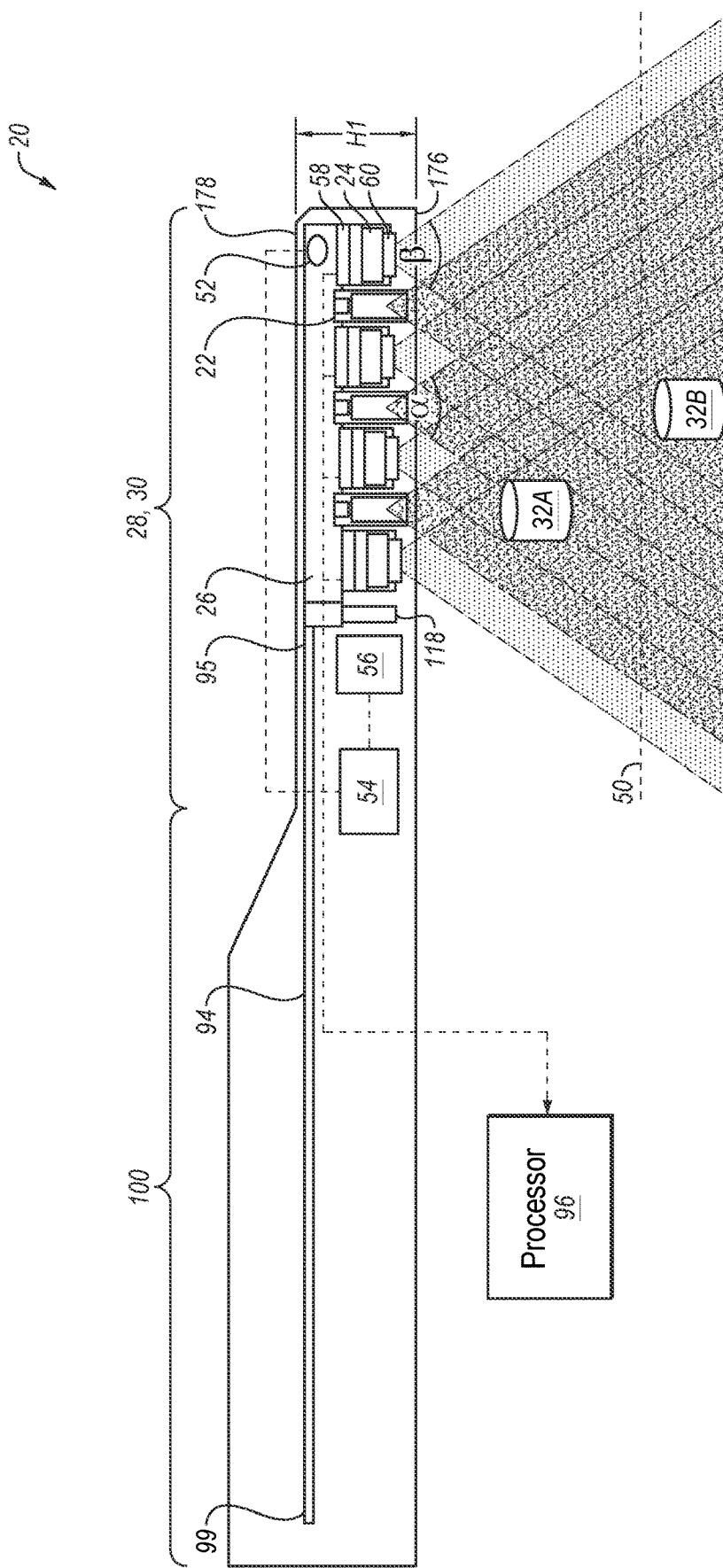
FIG. 5A is a schematic illustration of a handheld wand with a plurality of structured light projectors and cameras disposed within a probe at a distal end of the handheld wand, in accordance with embodiments of the present disclosure.

Reference is now made to FIG. 5A, which is a schematic illustration of an elongate handheld wand 20 for intraoral scanning, in accordance with some applications of the present disclosure. A plurality of light projectors 22 (e.g., including structured light projectors and/or unstructured light projectors) and a plurality of cameras 24 are coupled to a rigid structure 26 disposed within a probe 28 at a distal end 30 of the handheld wand. In some applications, during an intraoral scan, probe 28 enters the oral cavity of a subject.

For some applications, light projectors 22 are positioned within probe 28 such that one or more light projector 22 faces a 3D surface 32A and/or a 3D surface 32B outside of handheld wand 20 that is placed in its field of illumination, as opposed to positioning the light projectors in a proximal end of the handheld wand and illuminating the 3D surface by reflection of light off a mirror and subsequently onto the 3D surface. Similarly, for some applications, cameras 24 are positioned within probe 28 such that each camera 24 faces a 3D surface 32A, 32B outside of handheld wand 20 that is placed in its field of view, as opposed to positioning the cameras in a proximal end of the handheld wand and viewing the 3D surface by reflection of light off a mirror and into the camera. This positioning of the projectors and the cameras within probe 28 enables the scanner to have an overall large field of view while maintaining a low profile probe.

In some applications, a height H1 of probe 28 is less than 15 mm, height H1 of probe 28 being measured from a lower surface 176 (sensing surface), through which reflected light from 3D surface 32A, 32B being scanned enters probe 28, to an upper surface 178 opposite lower surface 176. In some applications, the height H1 is between 10-15 mm.

In some applications, cameras 24 each have a large field of view $\beta$ (beta) of at least 45 degrees, e.g., at least 70 degrees, e.g., at least 80 degrees, e.g., 85 degrees. In some applications, the field of view may be less than 120 degrees, e.g., less than 100 degrees, e.g., less than 90 degrees. In experiments performed by the inventors, field of view $\beta$ (beta) for each camera being between 80 and 90 degrees was found to be particularly useful because it provided a good balance among pixel size, field of view and camera overlap, optical quality, and cost. Cameras 24 may include a camera sensor 58 and objective optics 60 including one or more lenses. To enable close focus imaging cameras 24 may focus at an object focal plane 50 that is located between 1 mm and 30 mm, e.g., between 4 mm and 24 mm, e.g., between 5 mm and 11 mm, e.g., 9 mm-10 mm, from the lens that is farthest from the camera sensor. Cameras 24 may also detect 3D surfaces located at greater distances from the camera sensor, such as 3D surfaces at 40 mm, 50 mm, 60 mm, 70 mm, 80 mm, 90 mm, and so on from the camera sensor.

As described hereinabove, a large field of view achieved by combining the respective fields of view of all the cameras may improve accuracy due to reduced amount of image stitching errors, especially in edentulous regions, where the gum surface is smooth and there may be fewer clear high resolution 3-D features. Having a larger field of view enables large smooth features, such as the overall curve of the tooth, to appear in each image frame, which improves the accuracy of stitching respective surfaces obtained from multiple such image frames.

Similarly, light projectors 22 may each have a large field of illumination $\alpha$ (alpha) of at least 45 degrees, e.g., at least 70 degrees. In some applications, field of illumination a (alpha) may be less than 120 degrees, e.g., than 100 degrees.

For some applications, in order to improve image capture, each camera 24 has a plurality of discrete preset focus positions, in each focus position the camera focusing at a respective object focal plane 50. Each of cameras 24 may include an autofocus actuator that selects a focus position from the discrete preset focus positions in order to improve a given image capture. Additionally or alternatively, each camera 24 includes an optical aperture phase mask that extends a depth of focus of the camera, such that images formed by each camera are maintained focused over all 3D surface distances located between 1 mm and 30 mm, e.g., between 4 mm and 24 mm, e.g., between 5 mm and 11 mm, e.g., 9 mm-10 mm, from the lens that is farthest from the camera sensor. In further embodiments, images formed by one or more cameras may additionally be maintained focused over greater 3D surface distances, such as distances up to 40 mm, up to 50 mm, up to 60 mm, up to 70 mm, up to 80 mm, or up to 90 mm.

In some applications, light projectors 22 and cameras 24 are coupled to rigid structure 26 in a closely packed and/or alternating fashion, such that (a) a substantial part of each camera's field of view overlaps the field of view of neighboring cameras, and (b) a substantial part of each camera's field of view overlaps the field of illumination of neighboring projectors. Optionally, at least 20%, e.g., at least 50%, e.g., at least 75% of the projected pattern of light are in the field of view of at least one of the cameras at an object focal plane 50 that is located at least 4 mm from the lens that is farthest from the camera sensor. Due to different possible configurations of the projectors and cameras, some of the projected pattern may never be seen in the field of view of any of the cameras, and some of the projected pattern may be blocked from view by 3D surface 32A, 32B as the scanner is moved around during a scan.

Rigid structure 26 may be a non-flexible structure to which light projectors 22 and cameras 24 are coupled so as to provide structural stability to the optics within probe 28. Coupling all the projectors and all the cameras to a common rigid structure helps maintain geometric integrity of the optics of each light projector 22 and each camera 24 under varying ambient conditions, e.g., under mechanical stress as may be induced by the subject's mouth. Additionally, rigid structure 26 helps maintain stable structural integrity and positioning of light projectors 22 and cameras 24 with respect to each other. As further described hereinbelow, controlling the temperature of rigid structure 26 may help enable maintaining geometrical integrity of the optics through a large range of ambient temperatures as probe 28 enters and exits a subject's oral cavity or as the subject breathes during a scan.

As shown, 3D surface 32A and 3D surface 32B are in a FOV of the probe 28, with 3D surface 32A being relatively close to the probe 28 and 3D surface 32B being relatively far from the probe 28.

Figure 5B:
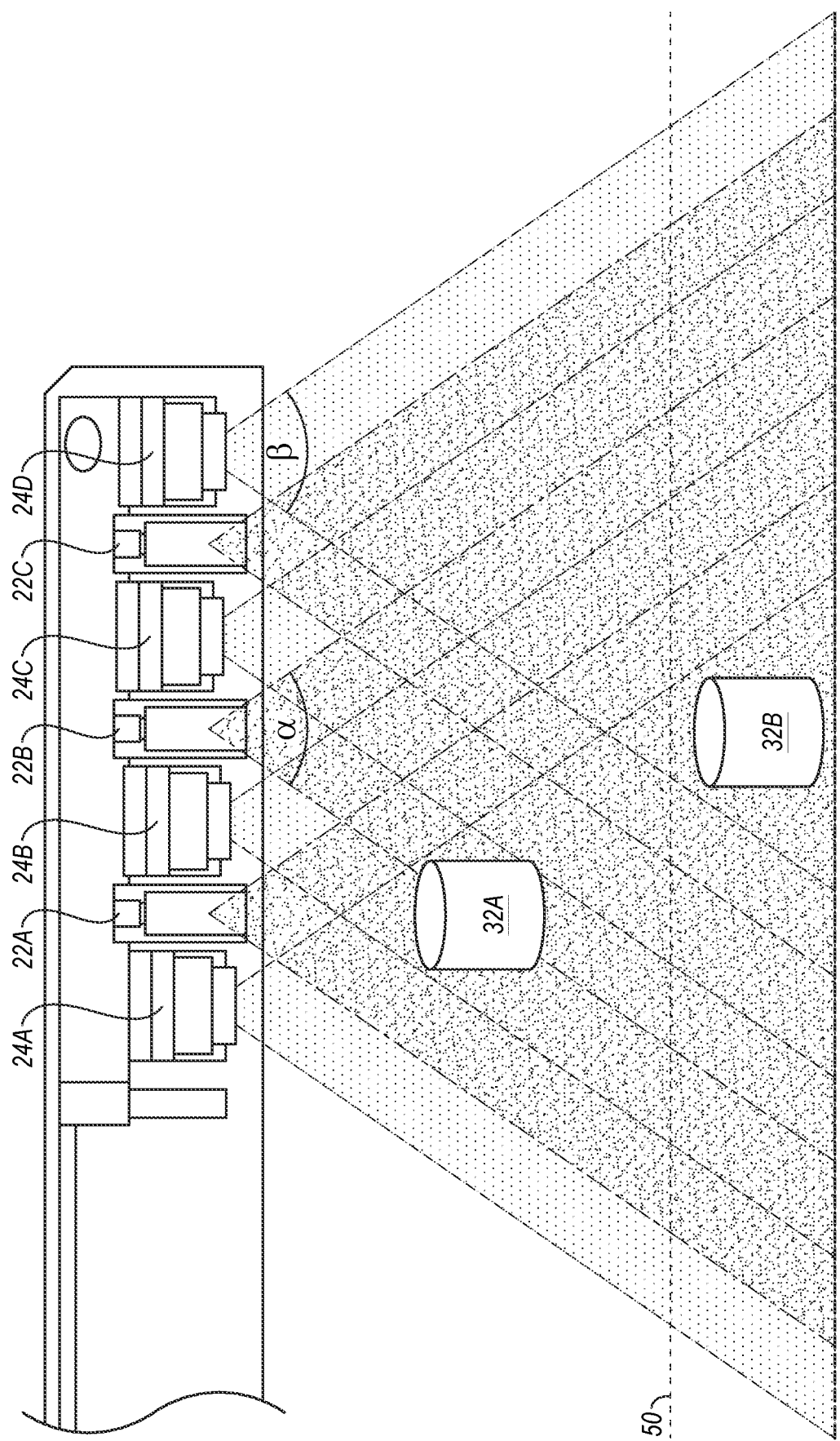
FIG. 5B is a schematic illustration of a zoomed in view of a portion of the probe and 3D surfaces of FIG. 5A.

Referring to FIG. 5B, a zoomed in view of a portion of the probe 28 and 3D surfaces 32A, 32B of FIG. 5A is shown. As shown in the illustrated example, probe 28 includes a first light projector 22A, a second light projector 22B and a third light projector 22C. Additionally, probe 28 includes a first camera 24A, a second camera 24B, a third camera 24C, and a fourth camera 24D. 3D surface 32A is in the FOV of the first camera 24A and the first light projector 22A. However, 3D surface 32A is not in the FOV of the fourth camera 24D. 3D surface 32B, which is further away from probe 28 than 3D surface 32, is in the FOV of first light projector 22A and fourth camera 24D. A first distance (referred to as a base line) between first light projector 22A and first camera 24A is lower than a second distance (base line) between fourth camera 24D and first light projector 22A. Accordingly, correspondence data for first light projector 22A and forth camera 24D may be used to determine a depth of 3D surface 32B more accurately than correspondence data for first light projector 22A and first camera 24A.

Similarly, 3D surface 32A is in the FOV of first camera 24A and second camera 24B, but is not in the FOV of fourth camera 24D. Thus, image data from the first camera 24A and second camera 24B may be used to determine a depth of 3D surface 32. 3D surface 32B is in the FOV of first camera 24A and fourth camera 24D. Thus, image data from first camera 24A and fourth camera 24D may be used to determine a depth of 3D surface 32B. Since a distance (base line) between first camera 24A and fourth camera 24D is larger than the distance between first camera 24A and second camera 24B, the image data from first camera 24A and fourth camera 24D may be used to determine the depth of 3D surface 32B with increased accuracy.

Whether a pair of cameras or a pair of a camera and a light projector are used, the accuracy of the triangulation used to determine the depth of 3D surfaces 32A and 32B may be roughly estimated by the following equation:

$$z_{err} = \frac{p_{err} \cdot z^2}{f \cdot b}$$

Where $z_{err}$ is the error in the depth, $p_{err}$ is the basic image processing error (generally a sub-pixel error), z is the depth, f is the focal length of the lens, and b is the base line (the distance between two cameras when using stereo imaging or the distance between the camera and the light projector when using structured light). In embodiments, the probe of the intraoral scanner is configured such that the maximum baseline between two cameras or between a camera and a light projector is large and provides a high level of accuracy for triangulation.

Figure 6:
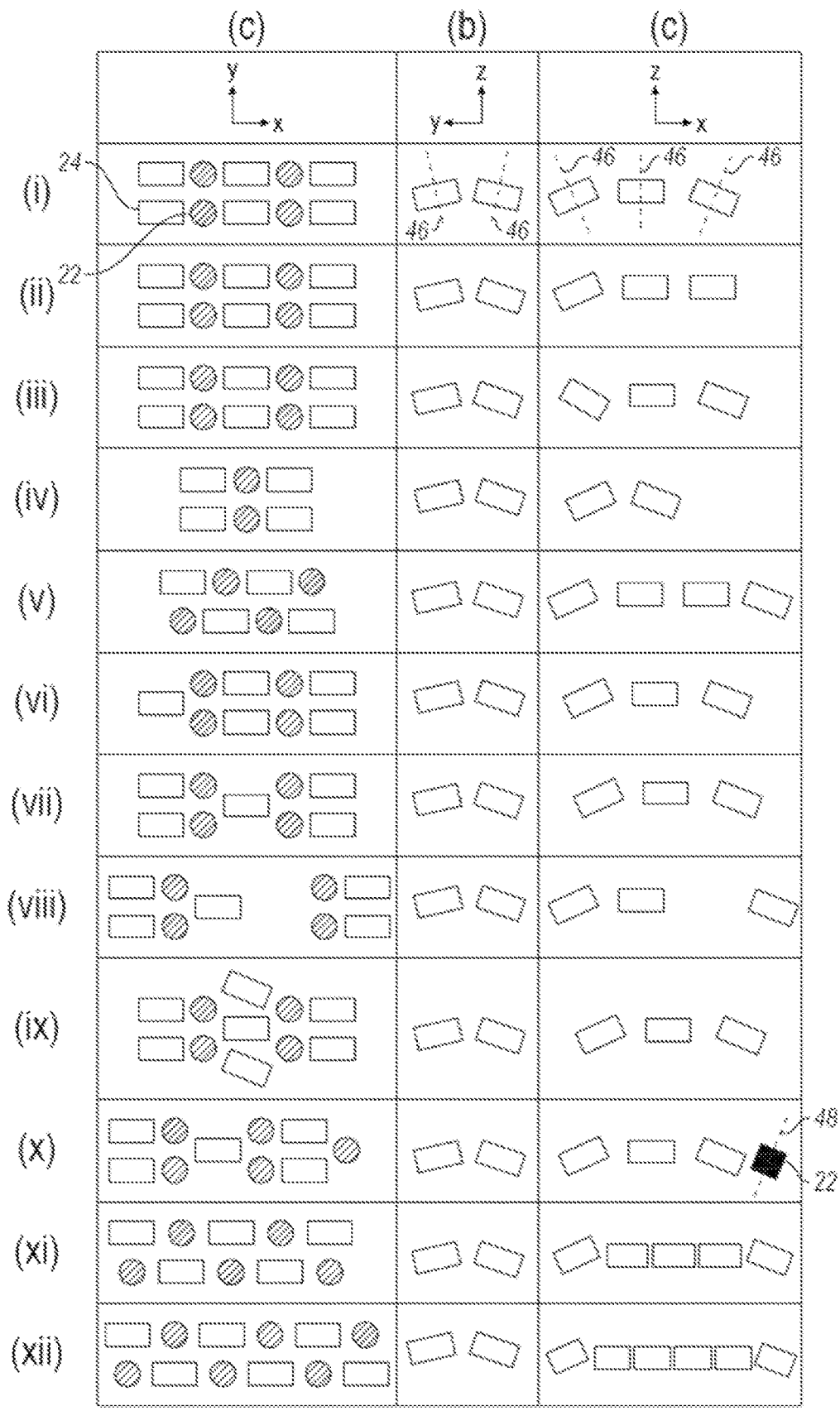
FIG. 6 is a chart depicting a plurality of different configurations for the position of the structured light projectors and the cameras in the probe of FIG. 5A, in accordance with embodiments of the present disclosure.

Reference is now made to FIG. 6, which is a chart depicting a plurality of different configurations for the position of light projectors 22 and cameras 24 in probe 28, in accordance with some applications of the present disclosure. Light projectors 22 are represented in FIG. 6 by circles and cameras 24 are represented in FIG. 6 by rectangles. It is noted that rectangles are used to represent the cameras, since typically, each camera sensor 58 and the field of view β (beta) of each camera 24 have aspect ratios of 1:2. Column (a) of FIG. 6 shows a bird's eye view of the various configurations of light projectors 22 and cameras 24. The x-axis as labeled in the first row of column (a) corresponds to a central longitudinal axis of probe 28. Column (b) shows a side view of cameras 24 from the various configurations as viewed from a line of sight that is coaxial with the central longitudinal axis of probe 28. Column (b) of FIG. 6 shows cameras 24 positioned so as to have optical axes 46 at an angle of 90 degrees or less, e.g., 35 degrees or less, with respect to each other. Column (c) shows a side view of cameras 24 of the various configurations as viewed from a line of sight that is perpendicular to the central longitudinal axis of probe 28.

Typically, the distal-most (toward the positive x-direction in FIG. 6) and proximal-most (toward the negative x-direction in FIG. 6) cameras 24 are positioned such that their optical axes 46 are slightly turned inwards, e.g., at an angle of 90 degrees or less, e.g., 35 degrees or less, with respect to the next closest camera 24. The camera(s) 24 that are more centrally positioned, i.e., not the distal-most camera 24 nor proximal-most camera 24, are positioned so as to face directly out of the probe, their optical axes 46 being substantially perpendicular to the central longitudinal axis of probe 28. It is noted that in row (xi) a projector 22 is positioned in the distal-most position of probe 28, and as such the optical axis 48 of that projector 22 points inwards, allowing a larger number of spots 33 projected from that particular projector 22 to be seen by more cameras 24.

Typically, the number of light projectors 22 in probe 28 may range from two, e.g., as shown in row (iv) of FIG. 6, to six, e.g., as shown in row (xii). Typically, the number of cameras 24 in probe 28 may range from four, e.g., as shown in rows (iv) and (v), to seven, e.g., as shown in row (ix). It is noted that the various configurations shown in FIG. 6 are by way of example and not limitation, and that the scope of the present disclosure includes additional configurations not shown. For example, the scope of the present disclosure includes more than five projectors 22 positioned in probe 28 and more than seven cameras positioned in probe 28.

In an example application, an apparatus for intraoral scanning (e.g., an intraoral scanner) includes an elongate handheld wand comprising a probe at a distal end of the elongate handheld wand, at least two light projectors disposed within the probe, and at least four cameras disposed within the probe. Each light projector may include at least one light source configured to generate light when activated, and a pattern generating optical element that is configured to generate a pattern of light when the light is transmitted through the pattern generating optical element. Each of the at least four cameras may include a camera sensor and one or more lenses, wherein each of the at least four cameras is configured to capture a plurality of images that depict at least a portion of the projected pattern of light on an intraoral surface. A majority of the at least two light projectors and the at least four cameras may be arranged in at least two rows that are each approximately parallel to a longitudinal axis of the probe, the at least two rows comprising at least a first row and a second row.

In a further application, a distal-most camera along the longitudinal axis and a proximal-most camera along the longitudinal axis of the at least four cameras are positioned such that their optical axes are at an angle of 90 degrees or less with respect to each other from a line of sight that is perpendicular to the longitudinal axis. Cameras in the first row and cameras in the second row may be positioned such that optical axes of the cameras in the first row are at an angle of 90 degrees or less with respect to optical axes of the cameras in the second row from a line of sight that is coaxial with the longitudinal axis of the probe. A remainder of the at least four cameras other than the distal-most camera and the proximal-most camera have optical axes that are substantially parallel to the longitudinal axis of the probe. Each of the at least two rows may include an alternating sequence of light projectors and cameras.

In a further application, the at least four cameras comprise at least five cameras, the at least two light projectors comprise at least five light projectors, a proximal-most component in the first row is a light projector, and a proximal-most component in the second row is a camera.

In a further application, the distal-most camera along the longitudinal axis and the proximal-most camera along the longitudinal axis are positioned such that their optical axes are at an angle of 35 degrees or less with respect to each other from the line of sight that is perpendicular to the longitudinal axis. The cameras in the first row and the cameras in the second row may be positioned such that the optical axes of the cameras in the first row are at an angle of 35 degrees or less with respect to the optical axes of the cameras in the second row from the line of sight that is coaxial with the longitudinal axis of the probe.

In a further application, the at least four cameras may have a combined field of view of about 25-45 mm or about 20-50 mm along the longitudinal axis and a field of view of about 20-40 mm or about 15-80 mm along a z-axis corresponding to distance from the probe. Other FOVs discussed herein may also be provided.

Figure 7:
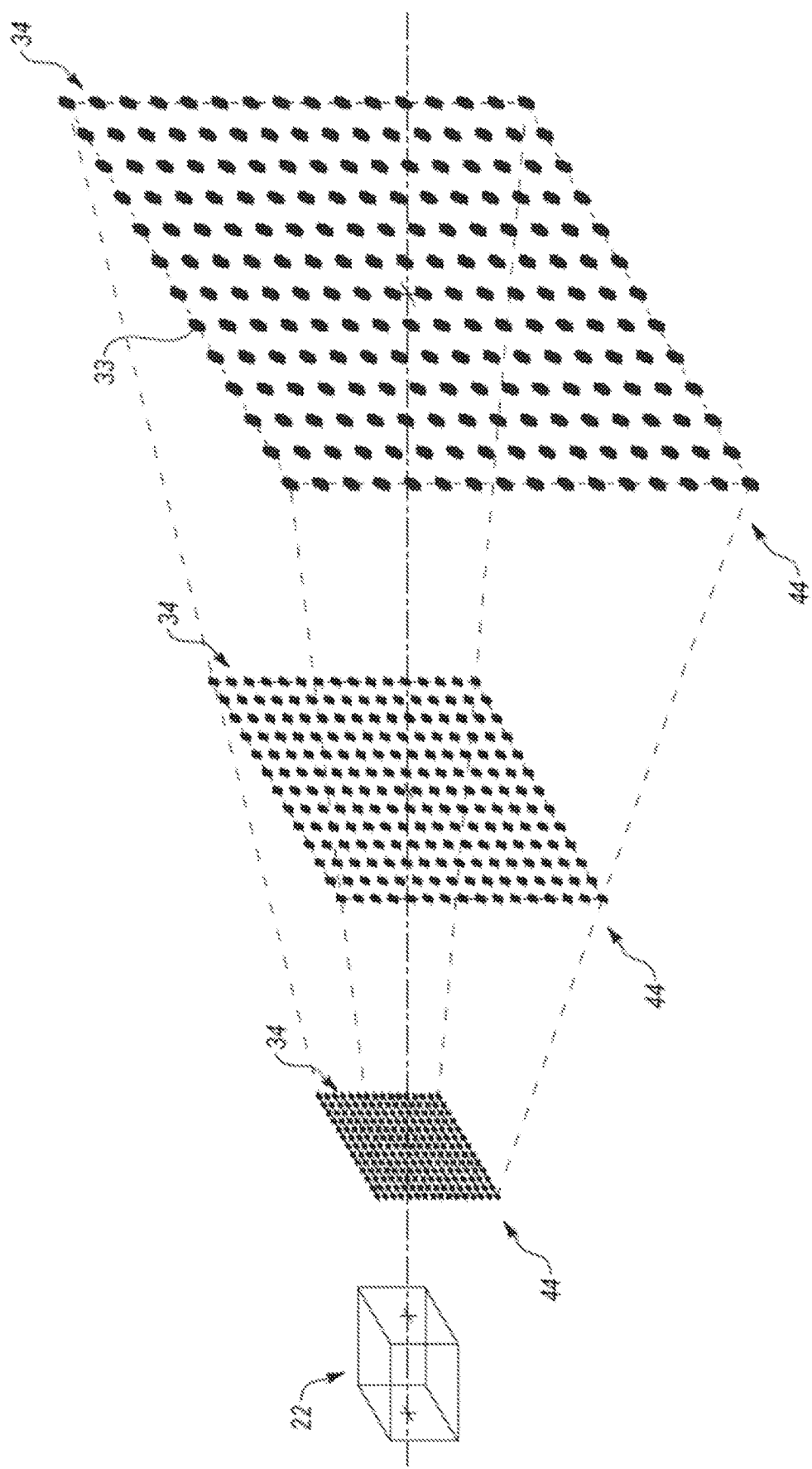
FIG. 7 is a schematic illustration of a structured light projector projecting a distribution of discrete unconnected spots of light onto a plurality of object focal planes, in accordance with embodiments of the present disclosure.

Reference is now made to FIG. 7, which is a schematic illustration of a structured light projector 22 projecting a distribution of discrete unconnected spots of light onto a plurality of object focal planes, in accordance with some applications of the present disclosure. 3D surface 32A, 32B being scanned may be one or more teeth or other intraoral object/tissue inside a subject's mouth. The somewhat translucent and glossy properties of teeth may affect the contrast of the structured light pattern being projected. For example, (a) some of the light hitting the teeth may scatter to other regions within the intraoral scene, causing an amount of stray light, and (b) some of the light may penetrate the tooth and subsequently come out of the tooth at any other point. Thus, in order to improve image capture of an intraoral scene under structured light illumination, without using contrast enhancement means such as coating the teeth with an opaque powder, a sparse distribution 34 of discrete unconnected spots of light may provide an improved balance between reducing the amount of projected light while maintaining a useful amount of information. The sparseness of distribution 34 may be characterized by a ratio of: (a) illuminated area on an orthogonal plane 44 in field of illumination a (alpha), i.e., the sum of the area of all projected spots 33 on the orthogonal plane 44 in field of illumination a (alpha), to (b) non-illuminated area on orthogonal plane 44 in field of illumination a (alpha). In some applications, sparseness ratio may be at least 1:150 and/or less than 1:16 (e.g., at least 1:64 and/or less than 1:36).

In some applications, each structured light projector 22 projects at least 400 discrete unconnected spots 33 onto an intraoral three-dimensional surface during a scan. In some applications, each structured light projector 22 projects less than 3000 discrete unconnected spots 33 onto an intraoral surface during a scan. In order to reconstruct the three-dimensional surface from projected sparse distribution 34, correspondence between respective projected spots 33 and the spots detected by cameras 24 is determined, as further described hereinbelow with reference to FIGS. 9-19.

Figure 8A:
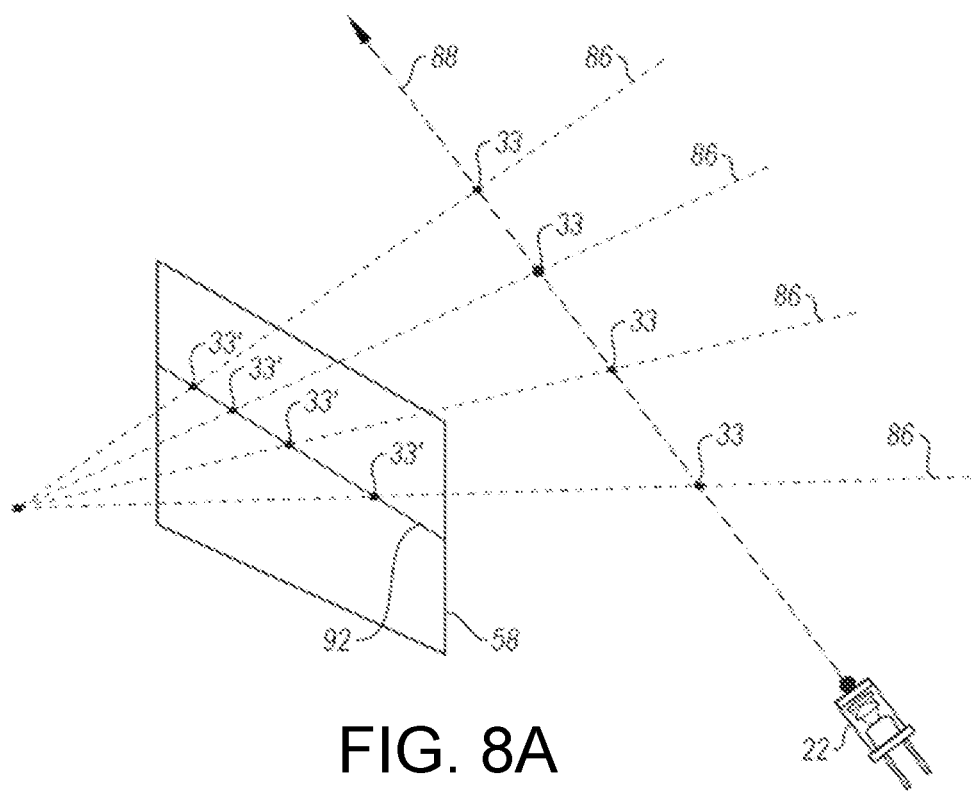
FIGS. 8A-B are schematic illustrations of a structured light projector projecting discrete unconnected spots and a camera sensor detecting spots, in accordance with embodiments of the present disclosure.
Figure 8B:
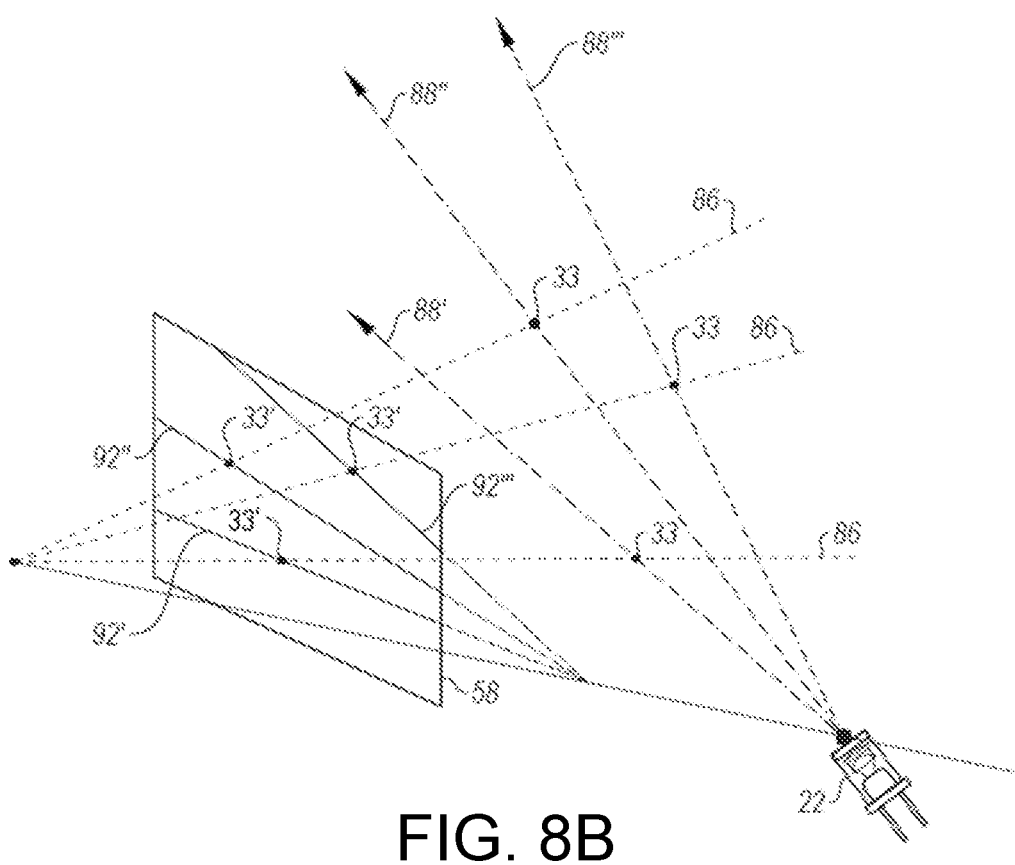

Reference is now made to FIGS. 8A-B, which are schematic illustrations of a structured light projector 22 projecting discrete unconnected spots 33 and a camera sensor 58 detecting spots 33', in accordance with some applications of the present disclosure. For some applications, a method is provided for determining correspondence between the projected spots 33 on the intraoral surface and detected spots 33' on respective camera sensors 58. Once the correspondence is determined, a three-dimensional image of the surface is reconstructed. Each camera sensor 58 has an array of pixels, for each of which there exists a corresponding camera ray 86. Similarly, for each projected spot 33 from each projector 22 there exists a corresponding projector ray 88. Each projector ray 88 corresponds to a respective path 92 of pixels on at least one of camera sensors 58. Thus, if a camera sees a spot 33' projected by a specific projector ray 88, that spot 33' will necessarily be detected by a pixel on the specific path 92 of pixels that corresponds to that specific projector ray 88. With specific reference to FIG. 8B, the correspondence between respective projector rays 88 and respective camera sensor paths 92 is shown. Projector ray 88' corresponds to camera sensor path 92', projector ray 88" corresponds to camera sensor path 92", and projector ray 88''' corresponds to camera sensor path 92'''. For example, if a specific projector ray 88 were to project a spot into a dust-filled space, a line of dust in the air would be illuminated. The line of dust as detected by camera sensor 58 would follow the same path on camera sensor 58 as the camera sensor path 92 that corresponds to the specific projector ray 88.

During a calibration process, calibration values are stored based on camera rays 86 corresponding to pixels on camera sensor 58 of each one of cameras 24, and projector rays 88 corresponding to projected spots 33 of light from each structured light projector 22. For example, calibration values may be stored for (a) a plurality of camera rays 86 corresponding to a respective plurality of pixels on camera sensor 58 of each one of cameras 24, and (b) a plurality of projector rays 88 corresponding to a respective plurality of projected spots 33 of light from each structured light projector 22.

By way of example, the following calibration process may be used. A high accuracy dot target, e.g., black dots on a white background, is illuminated from below and an image is taken of the target with all the cameras. The dot target is then moved perpendicularly toward the cameras, i.e., along the z-axis, to a target plane. The dot-centers are calculated for all the dots in all respective z-axis positions to create a three-dimensional grid of dots in space. A distortion and camera pinhole model is then used to find the pixel coordinate for each three-dimensional position of a respective dot-center, and thus a camera ray is defined for each pixel as a ray originating from the pixel whose direction is towards a corresponding dot-center in the three-dimensional grid. The camera rays corresponding to pixels in between the grid points can be interpolated. The above-described camera calibration procedure is repeated for all respective wavelengths of respective laser diodes 36, such that included in the stored calibration values are camera rays 86 corresponding to each pixel on each camera sensor 58 for each of the wavelengths.

After cameras 24 have been calibrated and all camera ray 86 values stored, structured light projectors 22 may be calibrated as follows. A flat featureless target is used and structured light projectors 22 are turned on one at a time. Each spot is located on at least one camera sensor 58. Since cameras 24 are now calibrated, the three-dimensional spot location of each spot is computed by triangulation based on images of the spot in multiple different cameras. The above-described process is repeated with the featureless target located at multiple different z-axis positions. Each projected spot on the featureless target will define a projector ray in space originating from the projector.

Figure 9:
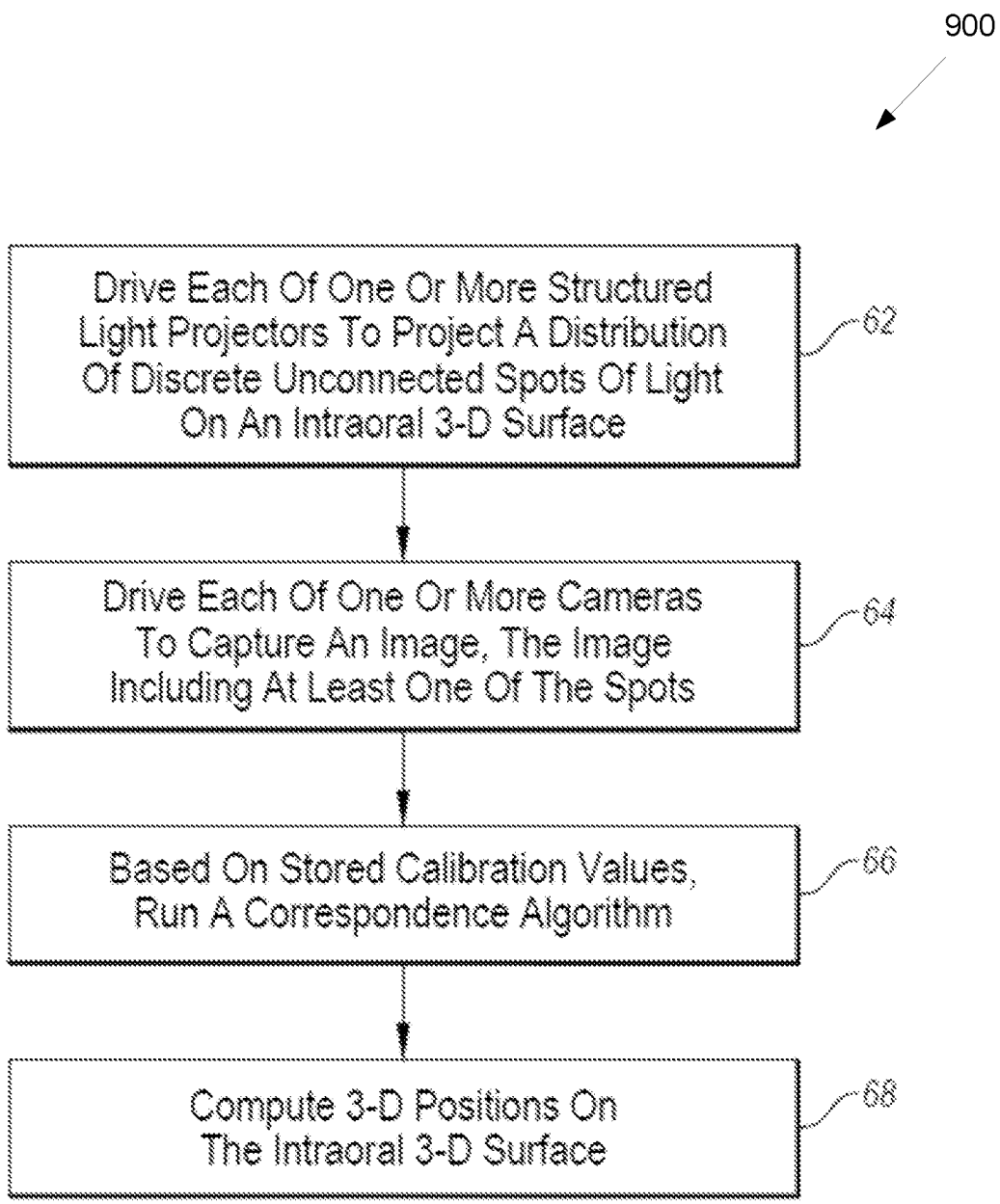
FIG. 9 is a flow chart outlining a method for determining depth values of points in an intraoral scan, in accordance with embodiments of the present disclosure.

Reference is now made to FIG. 9, which is a flow chart outlining a method 900 for determining depth values of points in an intraoral scan, in accordance with some applications of the present disclosure. Method 900 may be implemented, for example, at block 110 and 120 of method 101.

In operations 62 and 64, respectively, of method 900, each structured light projector 22 is driven to project distribution 34 of discrete unconnected spots 33 of light on an intraoral three-dimensional surface, and each camera 24 is driven to capture an image that includes at least one of spots 33. Based on the stored calibration values indicating (a) a camera ray 86 corresponding to each pixel on camera sensor 58 of each camera 24, and (b) a projector ray 88 corresponding to each projected spot 33 of light from each structured light projector 22, a correspondence algorithm is run in operation 66 using a processor 96, further described hereinbelow with reference to FIGS. 10-14. Processor 96 may be a processor of computing device 305 of FIG. 3 in embodiments, and may correspond to processing device 2020 of FIG. 20 in embodiments. Once the correspondence is solved, three-dimensional positions on the intraoral surface are computed in operation 68 and used to generate a digital three-dimensional image of the intraoral surface. Furthermore, capturing the intraoral scene using multiple cameras 24 provides a signal to noise improvement in the capture by a factor of the square root of the number of cameras.

Figure 10:
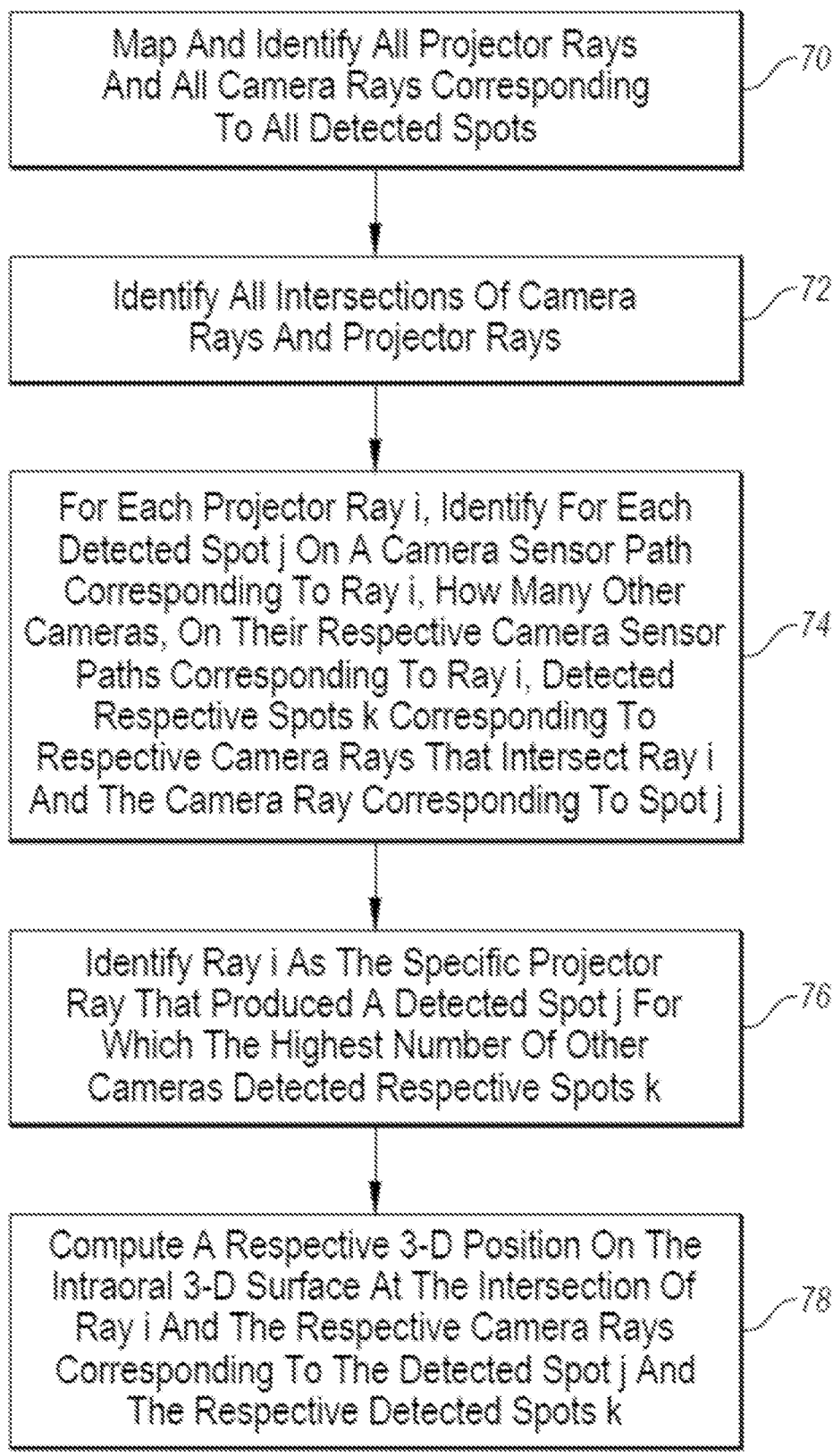
FIG. 10 is a flowchart outlining a method for carrying out a specific operation in the method of FIG. 9, in accordance with embodiments of the present disclosure.
Figure 11:
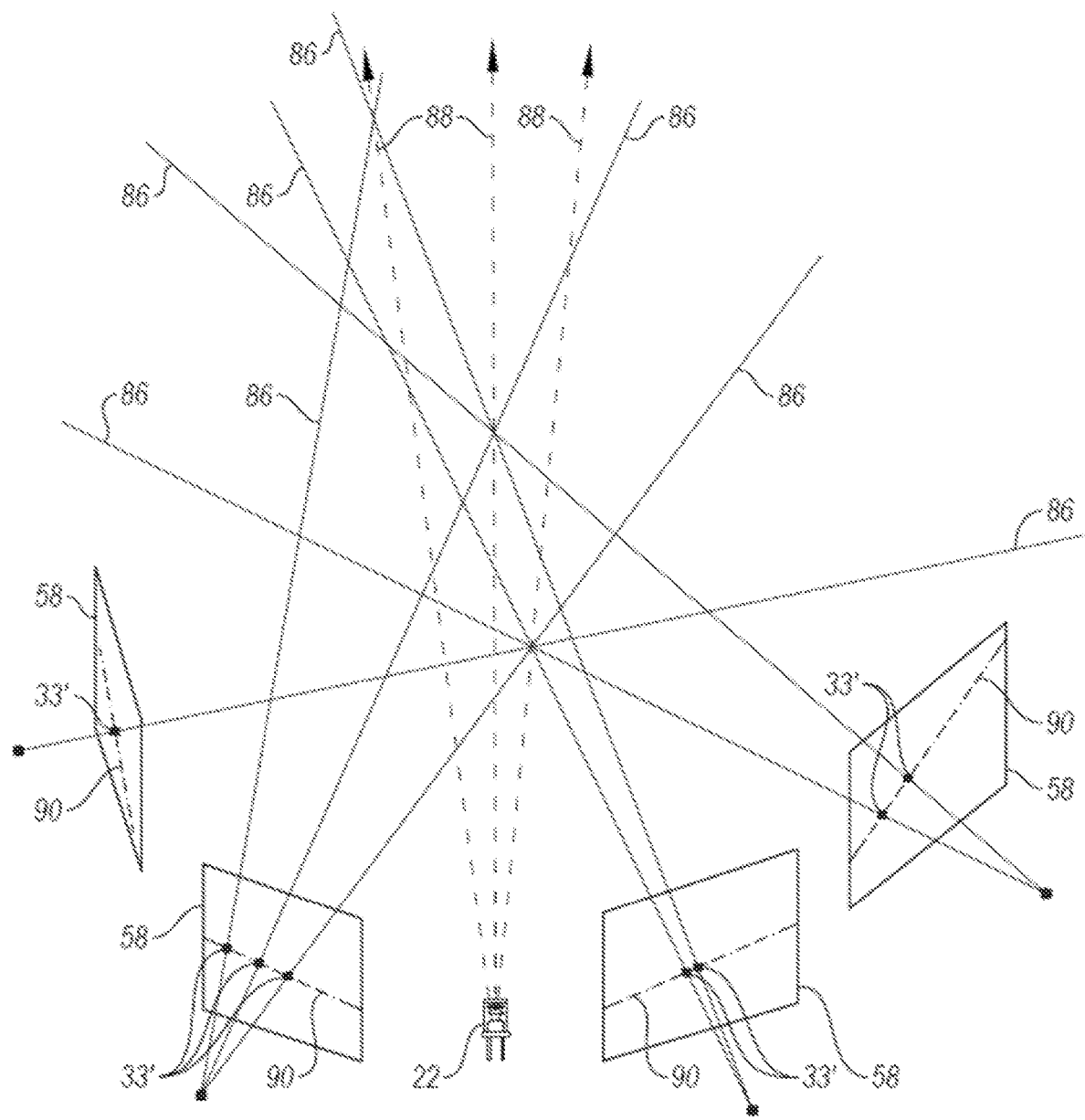
FIGS. 11, 12, 13, and 14 are schematic illustrations depicting a simplified example of the operations of FIG. 10, in accordance with embodiments of the present disclosure.
Figure 12:
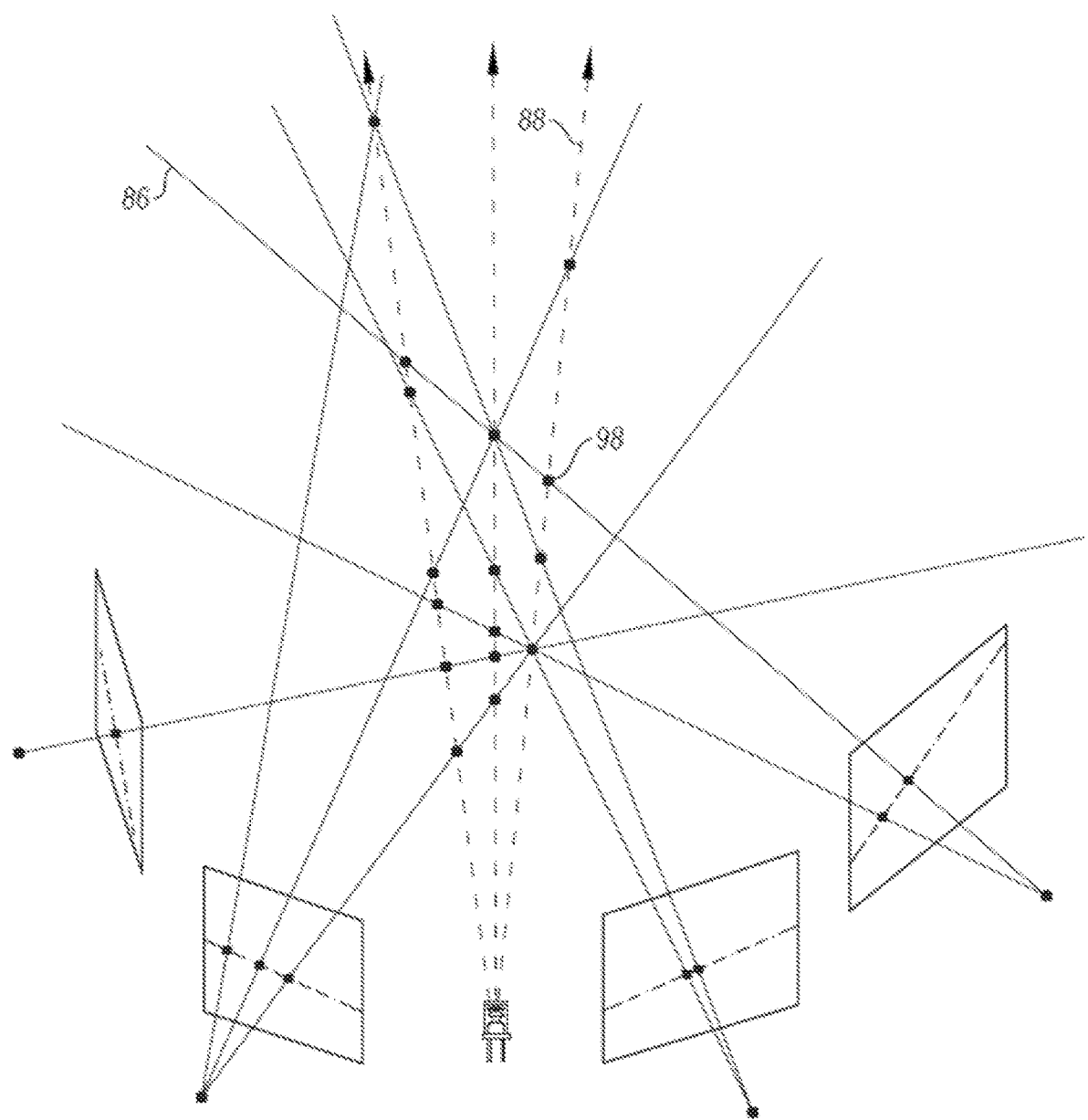

Reference is now made to FIG. 10, which is a flowchart outlining the correspondence algorithm of operation 66 in method 900, in accordance with some applications of the present disclosure. Based on the stored calibration values, all projector rays 88 and all camera rays 86 corresponding to all detected spots 33' are mapped (operation 70), and all intersections 98 (FIG. 12) of at least one camera ray 86 and at least one projector ray 88 are identified (operation 72). FIGS. 11 and 12 are schematic illustrations of a simplified example of operations 70 and 72 of FIG. 10, respectively. As shown in FIG. 11, three projector rays 88 are mapped along with eight camera rays 86 corresponding to a total of eight detected spots 33' on camera sensors 58 of cameras 24. As shown in FIG. 12, sixteen intersections 98 are identified.

Figure 13:
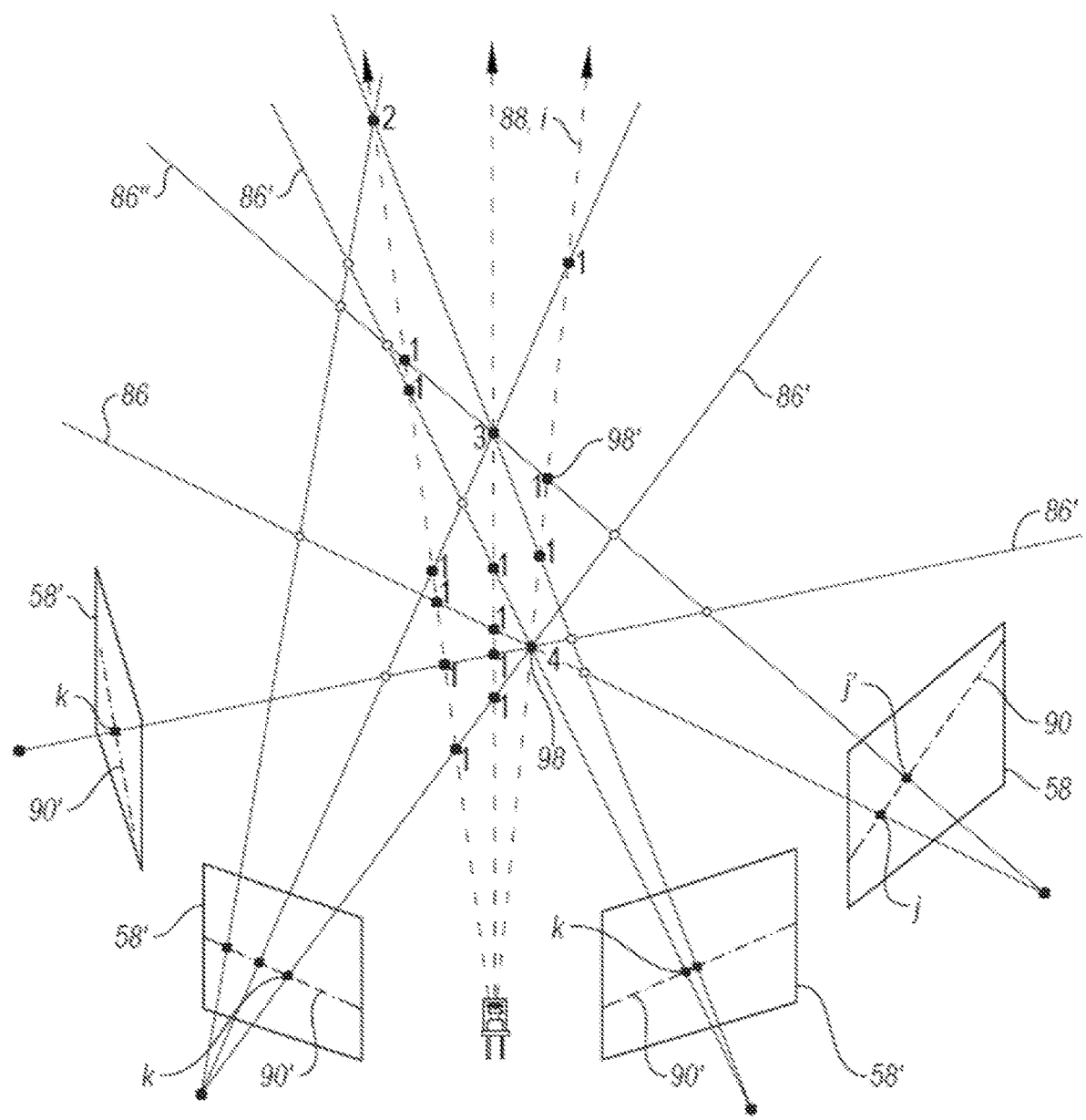

In operations 74 and 76 of method 900, processor 96 determines a correspondence between projected spots 33 and detected spots 33' so as to identify a three-dimensional location for each projected spot 33 on the surface. FIG. 13 is a schematic illustration depicting operations 74 and 76 of FIG. 10 using the simplified example described hereinabove in the immediately preceding paragraph. For a given projector ray i, processor 96 "looks" at the corresponding camera sensor path 90 on camera sensor 58 of one of cameras 24. Each detected spot j along camera sensor path 90 will have a camera ray 86 that intersects given projector ray i, at an intersection 98. Intersection 98 defines a three-dimensional point in space. Processor 96 then "looks" at camera sensor paths 90' that correspond to given projector ray i on respective camera sensors 58' of other cameras 24, and identifies how many other cameras 24, on their respective camera sensor paths 90' corresponding to given projector ray i, also detected respective spots k whose camera rays 86' intersect with that same three-dimensional point in space defined by intersection 98. The process is repeated for all detected spots j along camera sensor path 90, and the spot j for which the highest number of cameras 24 "agree," is identified as the spot 33 (FIG. 14) that is being projected onto the surface from given projector ray i. That is, projector ray i is identified as the specific projector ray 88 that produced a detected spot j for which the highest number of other cameras detected respective spots k. A three-dimensional position on the surface is thus computed for that spot 33.

Figure 14:
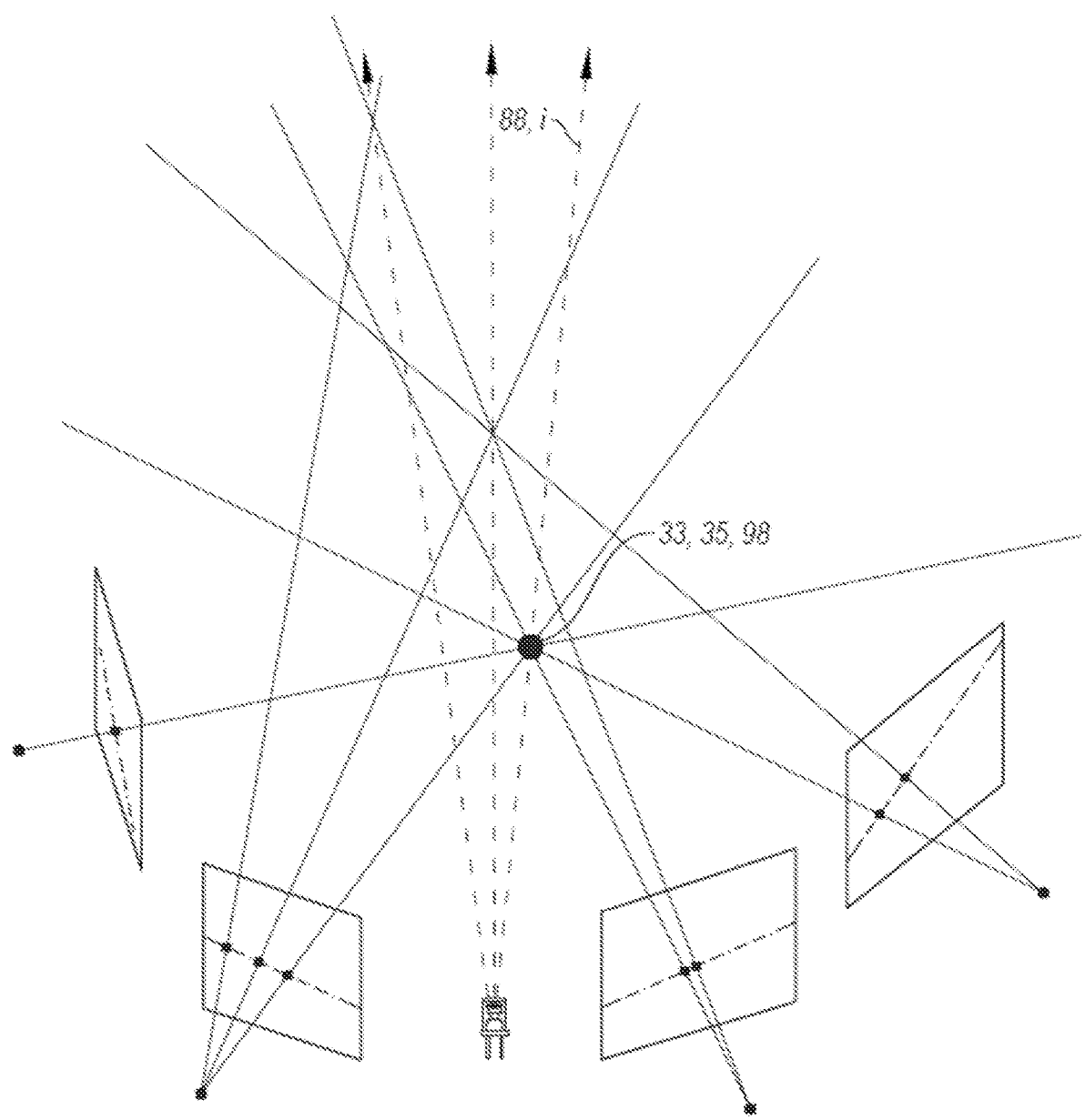

For example, as shown in FIG. 13, all four of the cameras detect respective spots, on their respective camera sensor paths corresponding to projector ray i, whose respective camera rays intersect projector ray i at intersection 98, intersection 98 being defined as the intersection of camera ray 86 corresponding to detected spot j and projector ray i. Hence, all four cameras are said to "agree" on there being a spot 33 projected by projector ray i at intersection 98. When the process is repeated for a next spot j', however, none of the other cameras detect respective spots, on their respective camera sensor paths corresponding to projector ray i, whose respective camera rays intersect projector ray i at intersection 98', intersection 98' being defined as the intersection of camera ray 86" (corresponding to detected spot j') and projector ray i. Thus, only one camera is said to "agree" on there being a spot 33 projected by projector ray i at intersection 98', while four cameras "agree" on there being a spot 33 projected by projector ray i at intersection 98. Projector ray i is therefore identified as being the specific projector ray 88 that produced detected spot j, by projecting a spot 33 onto the surface at intersection 98 (FIG. 14). As per operation 78 of FIG. 10, and as shown in FIG. 14, a three-dimensional position 35 on the intraoral surface is computed at intersection 98.

Figure 15:
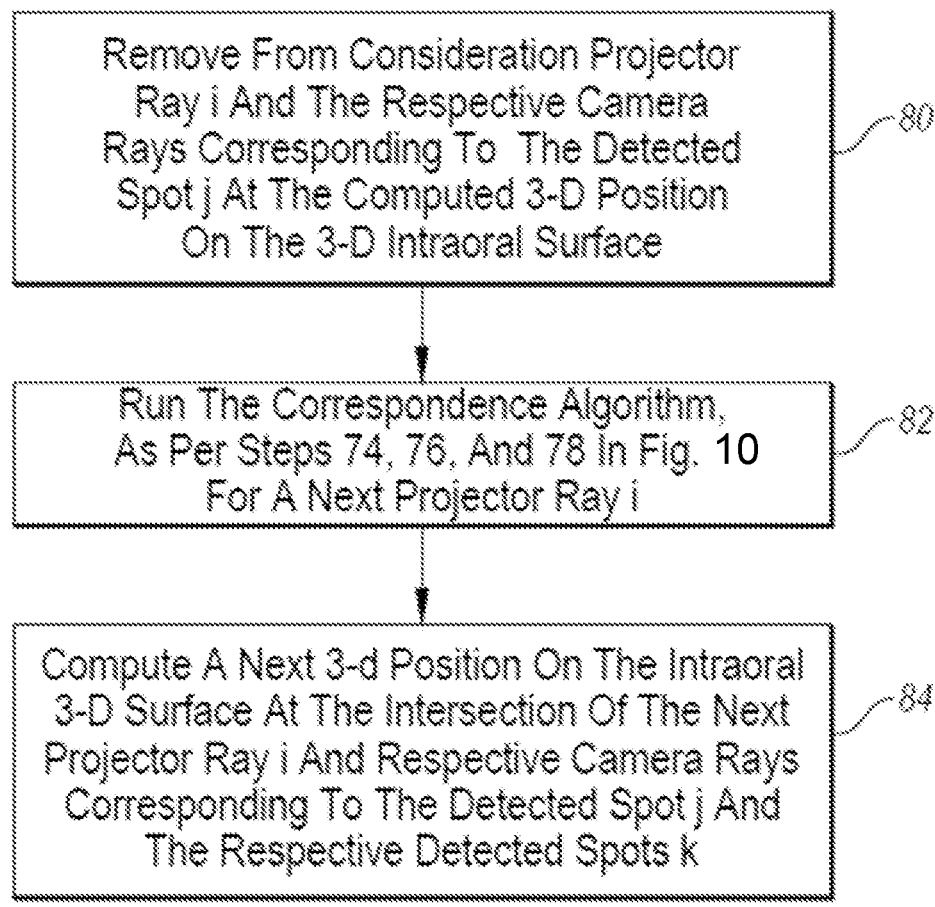
FIG. 15 is a flow chart outlining further operations in the method for generating a digital three-dimensional image, in accordance with embodiments of the present disclosure.
Figure 16:
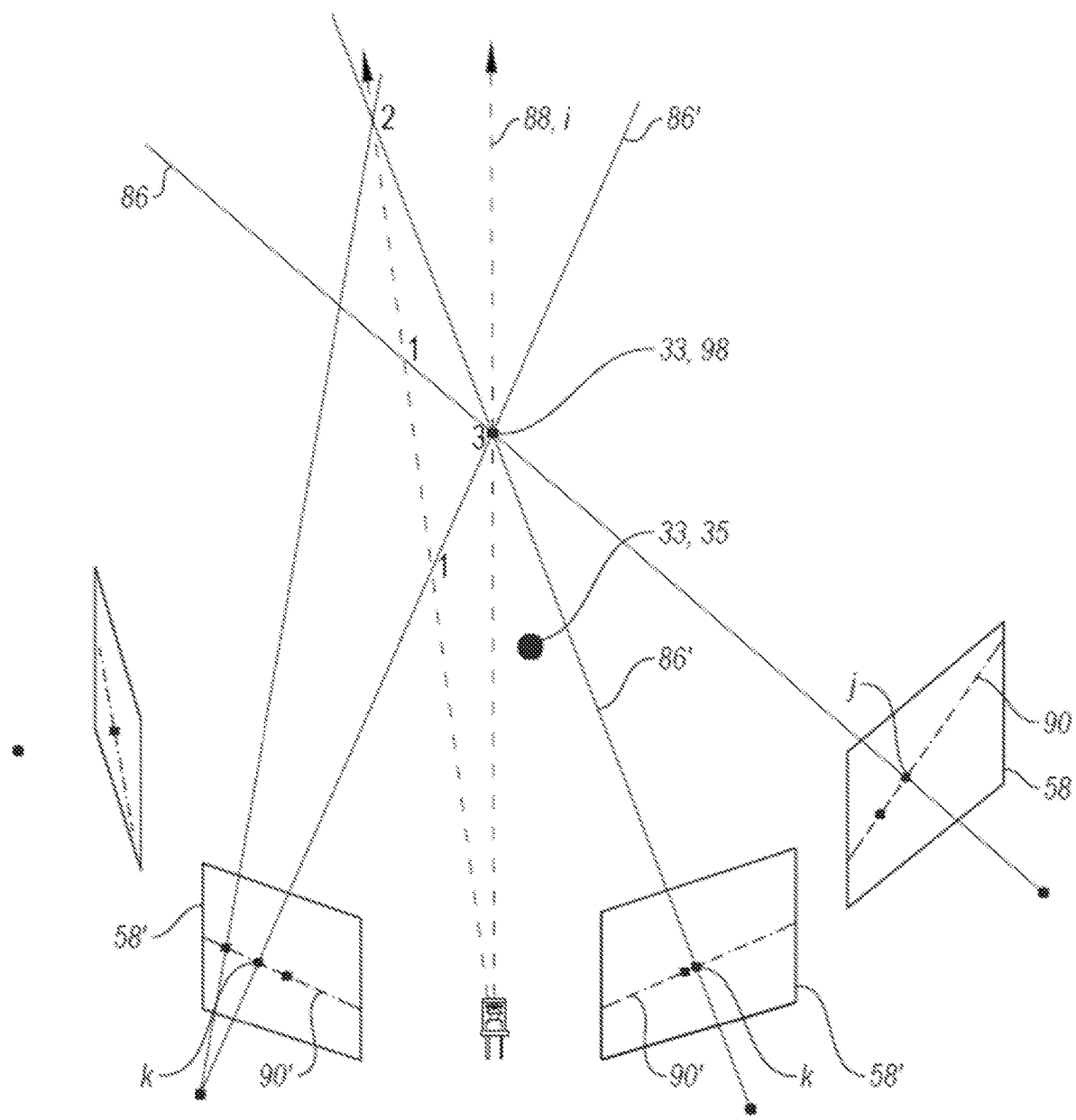
FIGS. 16, 17, 18, and 19 are schematic illustrations depicting a simplified example of the operations of FIG. 15, in accordance with embodiments of the present disclosure.
Figure 17:
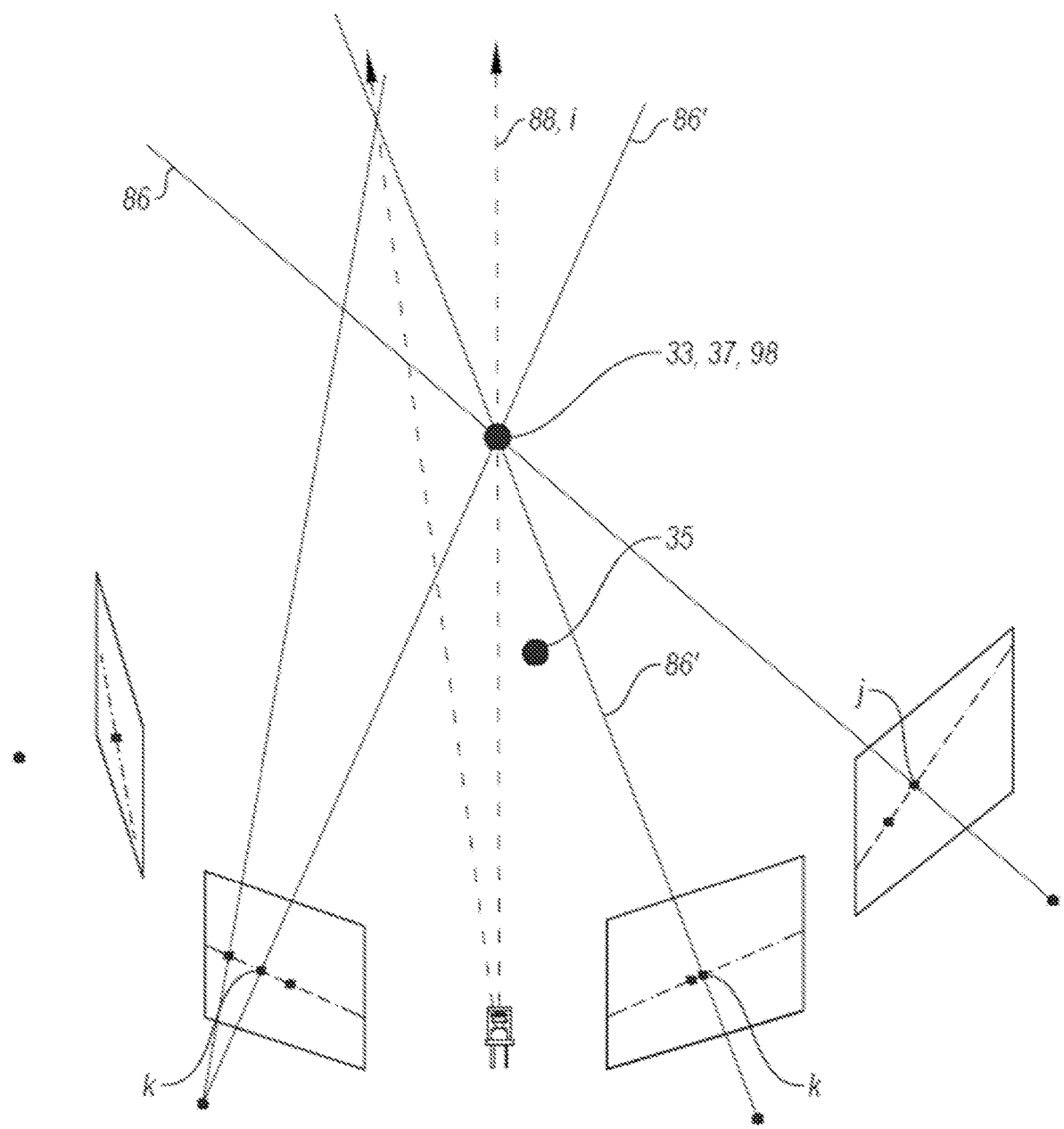

Reference is now made to FIG. 15, which is a flow chart outlining further operations in the correspondence algorithm, in accordance with some applications of the present disclosure. Once position 35 on the surface is determined, projector ray i that projected spot j, as well as all camera rays 86 and 86' corresponding to spot j and respective spots k are removed from consideration (operation 80) and the correspondence algorithm is run again for a next projector ray i (operation 82). FIG. 16 depicts the simplified example described hereinabove after the removal of the specific projector ray i that projected spot 33 at position 35. As per operation 82 in the flow chart of FIG. 15, the correspondence algorithm is then run again for a next projector ray i. As shown in FIG. 16, the remaining data show that three of the cameras "agree" on there being a spot 33 at intersection 98, intersection 98 being defined by the intersection of camera ray 86 corresponding to detected spot j and projector ray i. Thus, as shown in FIG. 17, a three-dimensional position 37 is computed at intersection 98.

Figure 18:
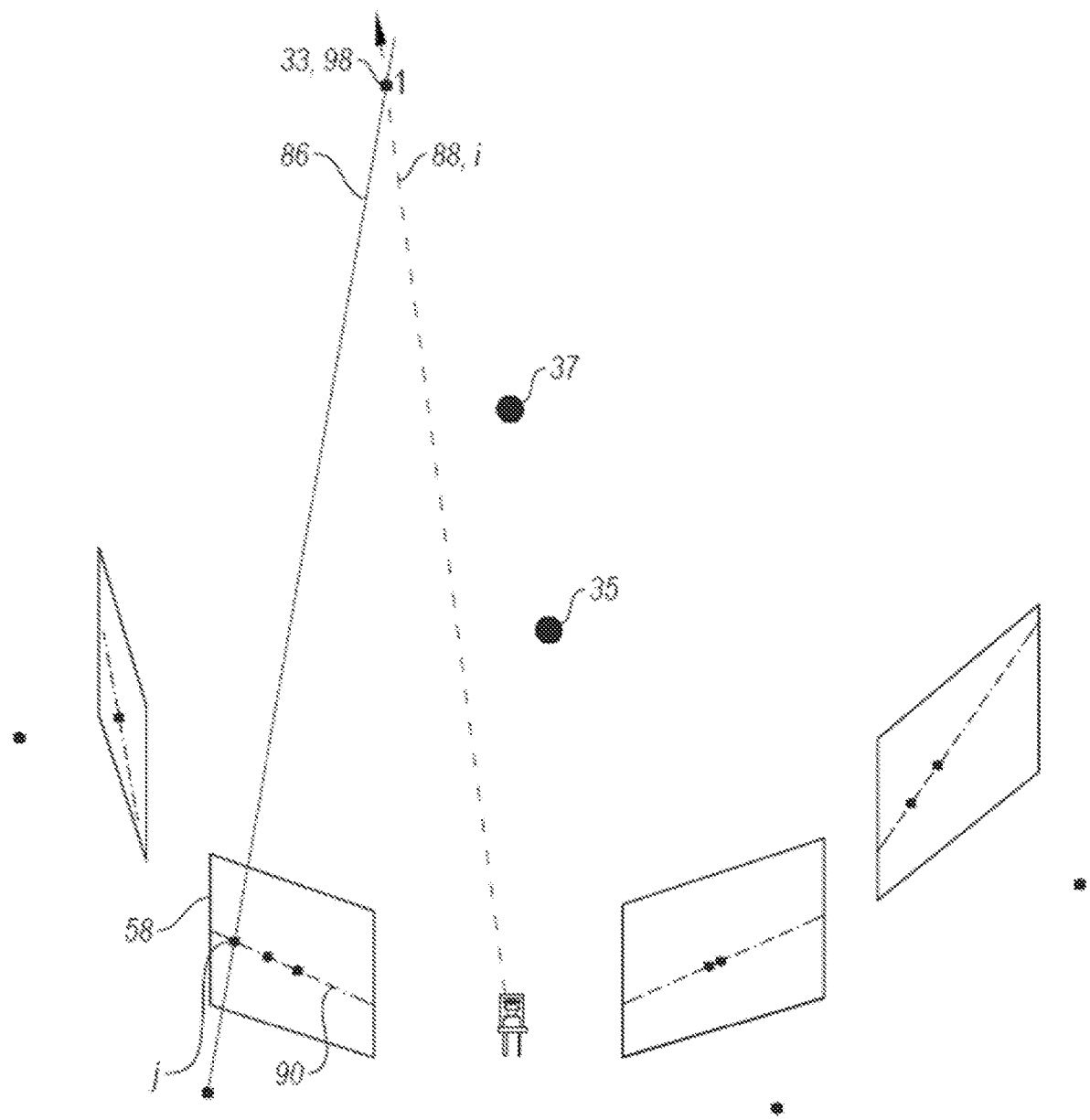
Figure 19:
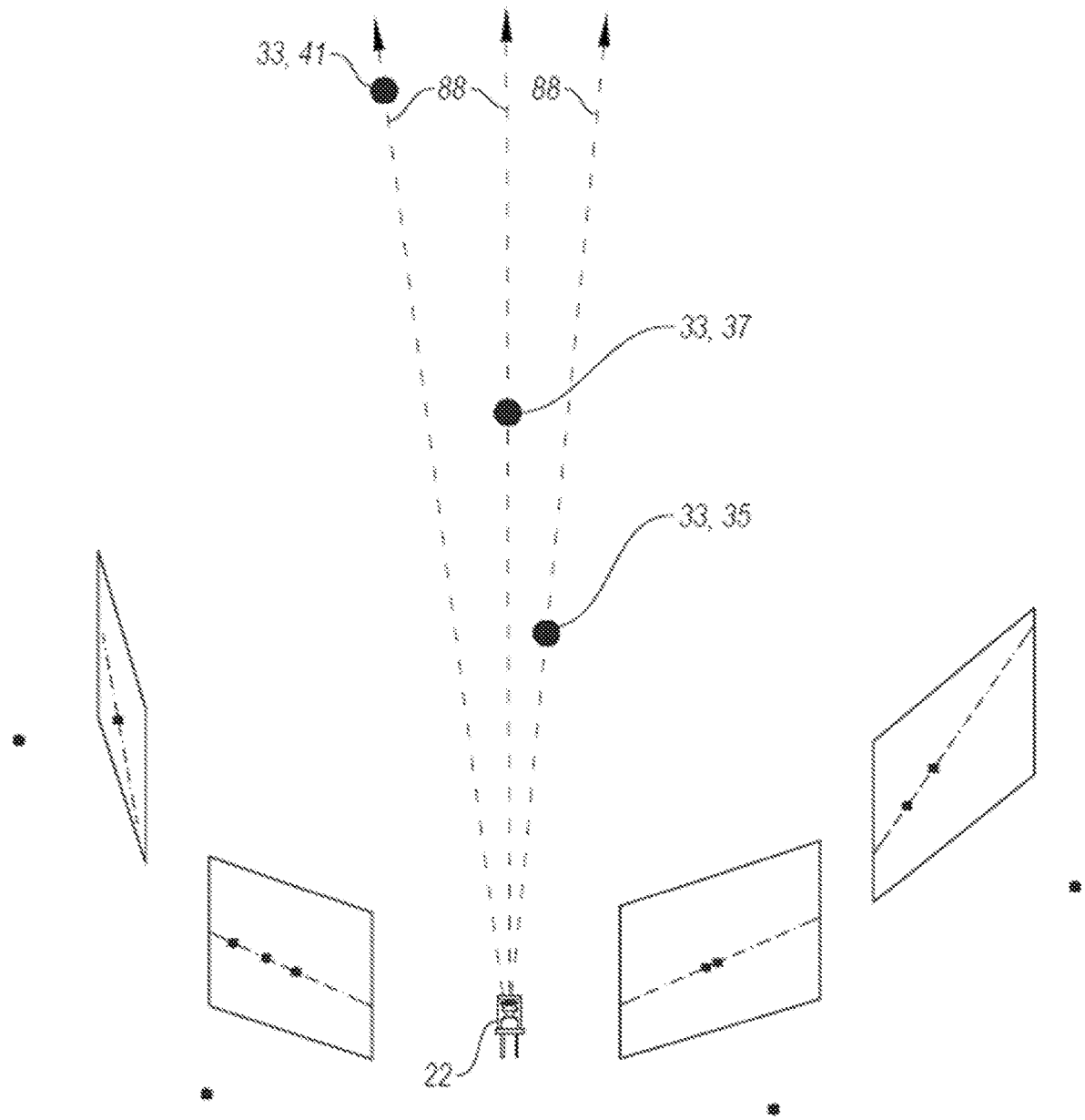

As shown in FIG. 18, once three-dimensional position 37 on the surface is determined, again projector ray i that projected spot j, as well as all camera rays 86 and 86' corresponding to spot j and respective spots k are removed from consideration. The remaining data show a spot 33 projected by projector ray i at intersection 98, and a three-dimensional position 41 on the surface is computed at intersection 98. As shown in FIG. 19, according to the simplified example, the three projected spots 33 of the three projector rays 88 of structured light projector 22 have now been located on the surface at three-dimensional positions 35, 37, and 41. In some applications, each structured light projector 22 projects 400-3000 spots 33. Once correspondence is solved for all projector rays 88, a reconstruction algorithm may be used to reconstruct a digital image of the surface using the computed three-dimensional positions of the projected spots 33.

Reference is again made to FIG. 5A. For some applications, there is at least one uniform light projector 118 coupled to rigid structure 26. Uniform light projector 118 transmits white light onto 3D surface 32, 33 being scanned. At least one camera, e.g., one of cameras 24, captures two-dimensional color images of 3D surface 32A using illumination from uniform light projector 118. Processor 96 may run a surface reconstruction algorithm that combines at least one image captured using illumination from structured light projectors 22 with a plurality of images captured using illumination from uniform light projector 118 in order to generate a digital three-dimensional image of the intraoral three-dimensional surface. Using a combination of structured light and uniform illumination enhances the overall capture of the intraoral scanner and may help reduce the number of options that processor 96 needs to consider when running the correspondence algorithm.

Figure 20:
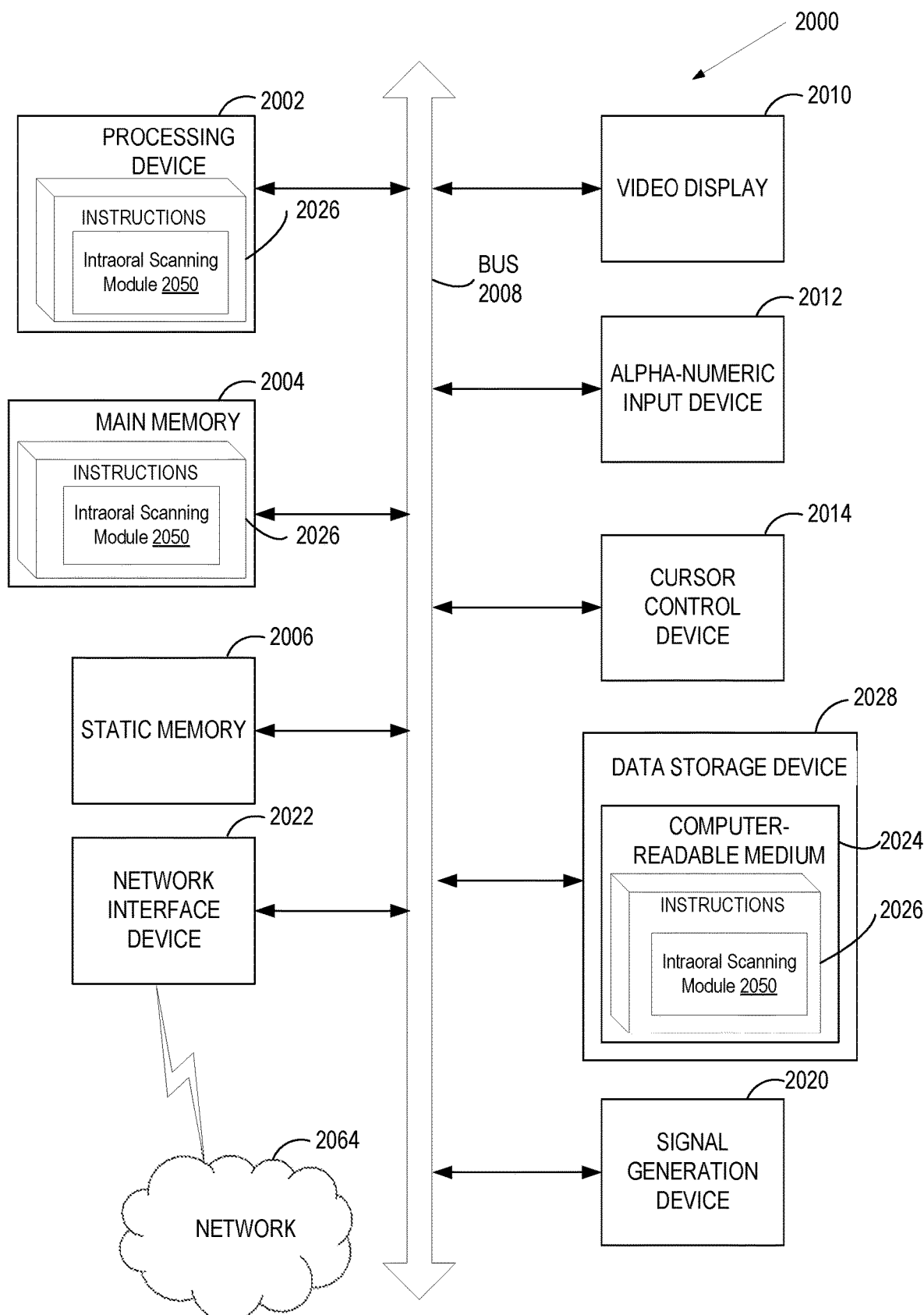
FIG. 20 illustrates a block diagram of an example computing device, in accordance with embodiments of the present disclosure.

FIG. 20 illustrates a diagrammatic representation of a machine in the example form of a computing device 2000 within which a set of instructions, for causing the machine to perform any one or more of the methodologies discussed herein, may be executed. In alternative embodiments, the machine may be connected (e.g., networked) to other machines in a Local Area Network (LAN), an intranet, an extranet, or the Internet. The machine may operate in the capacity of a server or a client machine in a client-server network environment, or as a peer machine in a peer-to-peer (or distributed) network environment. The machine may be a personal computer (PC), a tablet computer, a set-top box (STB), a Personal Digital Assistant (PDA), a cellular telephone, a web appliance, a server, a network router, switch or bridge, or any machine capable of executing a set of instructions (sequential or otherwise) that specify actions to be taken by that machine. Further, while only a single machine is illustrated, the term "machine" shall also be taken to include any collection of machines (e.g., computers) that individually or jointly execute a set (or multiple sets) of instructions to perform any one or more of the methodologies discussed herein.

The example computing device 2000 includes a processing device 2002, a main memory 2004 (e.g., read-only memory (ROM), flash memory, dynamic random access memory (DRAM) such as synchronous DRAM (SDRAM), etc.), a static memory 2006 (e.g., flash memory, static random access memory (SRAM), etc.), and a secondary memory (e.g., a data storage device 2028), which communicate with each other via a bus 2008.

Processing device 2002 represents one or more general-purpose processors such as a microprocessor, central processing unit, or the like. More particularly, the processing device 2002 may be a complex instruction set computing (CISC) microprocessor, reduced instruction set computing (RISC) microprocessor, very long instruction word (VLIW) microprocessor, processor implementing other instruction sets, or processors implementing a combination of instruction sets. Processing device 2002 may also be one or more special-purpose processing devices such as an application specific integrated circuit (ASIC), a field programmable gate array (FPGA), a digital signal processor (DSP), network processor, or the like. Processing device 2002 is configured to execute the processing logic (instructions 2026) for performing operations and operations discussed herein.

The computing device 2000 may further include a network interface device 2022 for communicating with a network 2064. The computing device 2000 also may include a video display unit 2010 (e.g., a liquid crystal display (LCD) or a cathode ray tube (CRT)), an alphanumeric input device 2012 (e.g., a keyboard), a cursor control device 2014 (e.g., a mouse), and a signal generation device 2020 (e.g., a speaker).

The data storage device 2028 may include a machine-readable storage medium (or more specifically a non-transitory computer-readable storage medium) 2024 on which is stored one or more sets of instructions 2026 embodying any one or more of the methodologies or functions described herein. Wherein a non-transitory storage medium refers to a storage medium other than a carrier wave. The instructions 2026 may also reside, completely or at least partially, within the main memory 2004 and/or within the processing device 2002 during execution thereof by the computer device 2000, the main memory 2004 and the processing device 2002 also constituting computer-readable storage media.

The computer-readable storage medium 2024 may also be used to store an intraoral scanning module 2050, which may correspond to similarly named components of FIG. 3. The computer readable storage medium 2024 may also store a software library containing methods that call an intraoral scanning module 2050, a scan registration module and/or a model generation module. While the computer-readable storage medium 2024 is shown in an example embodiment to be a single medium, the term "computer-readable storage medium" should be taken to include a single medium or multiple media (e.g., a centralized or distributed database, and/or associated caches and servers) that store the one or more sets of instructions. The term "computer-readable storage medium" shall also be taken to include any medium that is capable of storing or encoding a set of instructions for execution by the machine and that cause the machine to perform any one or more of the methodologies of the present disclosure. The term "computer-readable storage medium" shall accordingly be taken to include, but not be limited to, solid-state memories, and optical and magnetic media.

It is to be understood that the above description is intended to be illustrative, and not restrictive. Many other embodiments will be apparent upon reading and understanding the above description. Although embodiments of the present disclosure have been described with reference to specific example embodiments, it will be recognized that the disclosure is not limited to the embodiments described, but can be practiced with modification and alteration within the spirit and scope of the appended claims. Accordingly, the specification and drawings are to be regarded in an illustrative sense rather than a restrictive sense. The scope of the disclosure should, therefore, be determined with reference to the appended claims, along with the full scope of equivalents to which such claims are entitled.

What is claimed is:

1. A method comprising:
    receiving, by a processing device, a plurality of intraoral scans of a dental arch;
    determining, by the processing device, that at least one intraoral scan of the plurality of intraoral scans comprises both a buccal view of a first three-dimensional (3D) surface disposed at a first quadrant of the dental arch and having a first depth that is less than a depth threshold and a lingual view of at least a feature of a second 3D surface disposed at a second quadrant of the dental arch and having a second depth that is greater than the depth threshold, wherein there is a distance between the first 3D surface and at least the feature of the second 3D surface in the at least one intraoral scan;

stitching together the plurality of intraoral scans; and generating a virtual 3D model of the dental arch from the plurality of intraoral scans, wherein the at least one intraoral scan is used for generation of both the first 3D surface of the virtual 3D model and the second 3D surface of the virtual 3D model, and wherein a distance between the first 3D surface and the second 3D surface in the virtual 3D model is based on the distance between first 3D surface and the feature of the second 3D surface in the at least one intraoral scan.

2. The method of claim 1, wherein an intermolar width of the dental arch depicted in the virtual 3D model differs from a true intermolar width of the dental arch by no more than 20 microns.

3. The method of claim 1, wherein the dental arch comprises at least one scan body having a known 3D shape, the method further comprising:

determining that the feature of the second 3D surface depicts a portion of the scan body based on a comparison of the feature of the second 3D surface to the known 3D shape; and determining a position of the second 3D surface in the at least one intraoral scan, wherein the known 3D shape is used to improve an accuracy of the position of the second 3D surface.

4. The method of claim 1, further comprising:

determining the first depth of the first 3D surface; and determining the second depth of the feature of the second 3D surface, wherein a largest depth of a point on the first 3D surface is smaller than a smallest depth of a point on the feature of the second 3D surface.

5. The method of claim 1, wherein the first depth is about 0-30 mm, and wherein the second depth is about 40-90 mm.

6. The method of claim 4, wherein:

the at least one intraoral scan comprises a plurality of detected spots, where each detected spot of the plurality of detected spots is based on a projected spot projected by a light projector of an intraoral scanner that has been captured by one or more cameras of a plurality of cameras of the intraoral scanner;

determining the first depth of the first 3D surface in the at least one intraoral scan comprises running a correspondence algorithm that determines three-dimensional positions for detected spots using the depth threshold, wherein the depth threshold limits searching for depths that are greater than the depth threshold for the detected spots; and determining the second depth of at least the feature of the second 3D surface in the at least one intraoral scan comprises running the correspondence algorithm without the depth threshold after the correspondence algorithm has been run using the depth threshold.

7. The method of claim 4, wherein:

determining the first depth of the first 3D surface in the at least one intraoral scan comprises searching for 3D surfaces that have depths that are less than the depth threshold; and determining the second depth of at least the feature of the second 3D surface in the at least one intraoral scan comprises searching for 3D surfaces that have depths that are greater than or equal to the depth threshold, wherein the searching for the 3D surfaces that have depths that are greater than or equal to the depth threshold is performed after all 3D surfaces with depths that are less than the depth threshold have been identified.

8. The method of claim 1, wherein:

the at least one intraoral scan was generated by an intraoral scanner comprising a plurality of cameras and a plurality of light projectors;

a first combination of data associated with a first projector of the plurality of light projectors and a first camera of the plurality of cameras is used to detect the first 3D surface, wherein the first projector has a first distance from the first camera; and a second combination of data associated with the first projector and a second camera of the plurality of cameras is used to detect at least the feature of the second 3D surface, wherein the first projector has a second distance from the second camera that is greater than the first distance.

9. The method of claim 1, wherein stitching together the plurality of intraoral scans comprises:

for each pair of a plurality of pairs of overlapping intraoral scans, registering a first intraoral scan from the pair with a second intraoral scan from the pair in a common reference frame, wherein a respective error is associated with the registering of the first intraoral scan to the second intraoral scan, the respective error having a respective magnitude;

weighting the respective magnitudes of the respective errors for the plurality of pairs of overlapping intraoral scans, wherein respective magnitudes associated with pairs of overlapping intraoral scans that include the at least one intraoral scan are assigned respective first weights that are higher than respective second weights that are assigned to one or more other pairs of overlapping intraoral scans; and applying a cost function to the plurality of pairs of overlapping intraoral scans to determine a cumulative error, wherein the respective magnitudes of the respective errors as modified by the respective first weights and the respective second weights are selected to minimize the cumulative error.

10. The method of claim 1, wherein:

as a result of stitching together the plurality of intraoral scans exclusive of the at least one intraoral scan, there are a first number of links between pairs of intraoral scans that connect the first 3D surface on the first quadrant of the dental arch to the second 3D surface on the second quadrant of the dental arch;

as a result of stitching together the plurality of intraoral scans inclusive of the at least one intraoral scan, there are a second number of links between pairs of intraoral scans that connect the first 3D surface on the first quadrant of the dental arch to the second 3D surface on the second quadrant of the dental arch; and the second number of links is lower than the first number of links and causes an increased accuracy in the virtual 3D model.

11. The method of claim 1, wherein the second 3D surface is not connected to the first 3D surface in the at least one intraoral scan.

12. A system comprising:

an intraoral scanner configured to generate a plurality of intraoral scans of a dental arch; and a computing device, wherein the computing device is to:
receive the plurality of intraoral scans of the dental arch;
determine that at least one intraoral scan of the plurality of intraoral scans comprises both a buccal view of a first three-dimensional (3D) surface disposed at a first quadrant of the dental arch and having a first depth that is less than a depth threshold and a lingual view of at least a feature of a second 3D surface disposed at a second quadrant of the dental arch and having a second depth that is greater than the depth threshold, wherein there is a distance between the first 3D surface and at least the feature of the second 3D surface in the at least one intraoral scan;
stitch together the plurality of intraoral scans; and
generate a virtual 3D model of the dental arch from the plurality of intraoral scans, wherein the at least one intraoral scan is used for generation of both the first 3D surface of the virtual 3D model and the second 3D surface of the virtual 3D model, and wherein a distance between the first 3D surface and the second 3D surface in the virtual 3D model is based on the distance between first 3D surface and the feature of the second 3D surface in the at least one intraoral scan.

13. The system of claim 12, wherein an intermolar width of the dental arch depicted in the virtual 3D model differs from a true intermolar width of the dental arch by no more than 20 microns.

14. The system of claim 12, wherein the dental arch comprises at least one scan body having a known 3D shape, and wherein the computing device is further to:
determine that the feature of the second 3D surface depicts a portion of the scan body based on a comparison of the feature of the second 3D surface to the known 3D shape; and
determine a position of the second 3D surface in the at least one intraoral scan, wherein the known 3D shape is used to improve an accuracy of the position of the second 3D surface.

15. The system of claim 12, wherein the computing device is further to:
determine the first depth of the first 3D surface; and
determine the second depth of the feature of the second 3D surface, wherein a largest depth of a point on the first 3D surface is smaller than a smallest depth of a point on the feature of the second 3D surface.

16. The system of claim 12, wherein the first depth is about 0-30 mm, and wherein the second depth is about 40-90 mm.

17. The system of claim 15, wherein:
the at least one intraoral scan comprises a plurality of detected spots, where each detected spot of the plurality of detected spots is based on a projected spot projected by a light projector of an intraoral scanner that has been captured by one or more cameras of a plurality of cameras of the intraoral scanner;
determining the first depth of the first 3D surface in the at least one intraoral scan comprises running a correspondence algorithm that determines three-dimensional positions for detected spots using the depth threshold, wherein the depth threshold limits searching for depths that are greater than the depth threshold for the detected spots; and
determining the second depth of at least the feature of the second 3D surface in the at least one intraoral scan comprises running the correspondence algorithm without the depth threshold after the correspondence algorithm has been run using the depth threshold.

18. The system of claim 15, wherein:
the at least one intraoral scan comprises a plurality of detected spots, where each detected spot of the plurality of detected spots is based on a projected spot projected by one of a plurality of light projectors of an intraoral scanner that has been captured by one or more cameras of a plurality of cameras of the intraoral scanner;
determining the first depth of the first 3D surface in the at least one intraoral scan comprises identifying a first correspondence of a first spot of the plurality of detected spots detected by a first camera of the plurality of cameras to a first projected spot projected by a first light projector of the plurality of light projectors, wherein the first light projector has a first distance from the first camera; and
determining the second depth of at least the feature of the second 3D surface in the at least one intraoral scan comprises identifying a second correspondence of a second spot of the plurality of detected spots detected by the first camera or a second camera of the plurality of cameras to a second projected spot projected by a second light projector of the plurality of light projectors, wherein the second light projector has a second distance from the first camera or the second camera, wherein the second distance is greater than the first distance.

19. The system of claim 15, wherein:
the at least one intraoral scan was generated by an intraoral scanner comprising a plurality of cameras;
the first 3D surface was in a first field of view (FOV) of a first camera of the plurality of cameras and in a second FOV of a second camera of the plurality of cameras that is a first distance from the first camera;
the feature of the second 3D surface was in the first FOV of the first camera or a third FOV of a third camera of the plurality of cameras and in a fourth FOV of a fourth camera of the plurality of cameras that is a second distance from the first camera or the third camera, wherein the second distance is greater than the first distance;
determining the first depth of the first 3D surface in the at least one intraoral scan comprises triangulating a first depiction of the first 3D surface as captured by a first camera with a second depiction of the first 3D surface as captured by the second camera; and
determining the second depth of the feature of the second 3D surface in the at least one intraoral scan comprises triangulating a first depiction of the feature of the second 3D surface as captured by the first camera or the third camera with a second depiction of the feature of the second 3D surface as captured by the fourth camera.

20. The system of claim 15, wherein:
determining the first depth of the first 3D surface in the at least one intraoral scan comprises searching for 3D surfaces that have depths that are less than the depth threshold; and
determining the second depth of at least the feature of the second 3D surface in the at least one intraoral scan comprises searching for 3D surfaces that have depths that are greater than or equal to the depth threshold, wherein the searching for the 3D surfaces that have depths that are greater than or equal to the depth threshold is performed after all 3D surfaces with depths that are less than the depth threshold have been identified.

21. The system of claim 12, wherein:
the at least one intraoral scan was generated by an intraoral scanner comprising a plurality of cameras and a plurality of light projectors;
a first combination of data associated with a first projector of the plurality of light projectors and a first camera of the plurality of cameras is used to detect the first 3D surface, wherein the first projector has a first distance from the first camera; and
a second combination of data associated with the first projector and a second camera of the plurality of cameras is used to detect at least the feature of the second 3D surface, wherein the first projector has a second distance from the second camera that is greater than the first distance.

22. The system of claim 12, wherein stitching together the plurality of intraoral scans comprises:
for each pair of a plurality of pairs of overlapping intraoral scans, registering a first intraoral scan from the pair with a second intraoral scan from the pair in a common reference frame, wherein a respective error is associated with the registering of the first intraoral scan to the second intraoral scan, the respective error having a respective magnitude;
weighting the respective magnitudes of the respective errors for the plurality of pairs of overlapping intraoral scans, wherein respective magnitudes associated with pairs of overlapping intraoral scans that include the at least one intraoral scan are assigned respective first weights that are higher than respective second weights that are assigned to one or more other pairs of overlapping intraoral scans; and
applying a cost function to the plurality of pairs of overlapping intraoral scans to determine a cumulative error, wherein the respective magnitudes of the respective errors as modified by the respective first weights and the respective second weights are selected to minimize the cumulative error.

23. The system of claim 12, wherein:
as a result of stitching together the plurality of intraoral scans exclusive of the at least one intraoral scan, there are a first number of links between pairs of intraoral scans that connect the first 3D surface on the first quadrant of the dental arch to the second 3D surface on the second quadrant of the dental arch;
as a result of stitching together the plurality of intraoral scans inclusive of the at least one intraoral scan, there are a second number of links between pairs of intraoral scans that connect the first 3D surface on the first quadrant of the dental arch to the second 3D surface on the second quadrant of the dental arch; and
the second number of links is lower than the first number of links and causes an increased accuracy in the virtual 3D model.

24. The system of claim 12, wherein the second 3D surface is not connected to the first 3D surface in the at least one intraoral scan.

* * * * *